United States Patent
Rasdal et al.

(10) Patent No.: US 7,927,274 B2
(45) Date of Patent: *Apr. 19, 2011

(54) INTEGRATED RECEIVER FOR CONTINUOUS ANALYTE SENSOR

(75) Inventors: Andrew Rasdal, San Diego, CA (US); James H. Brauker, Cement City, MI (US); Paul V. Neale, San Diego, CA (US); Peter C. Simpson, Encinitas, CA (US)

(73) Assignee: DexCom, Inc., San Diego, CA (US)

( * ) Notice: Subject to any disclaimer, the term of this patent is extended or adjusted under 35 U.S.C. 154(b) by 211 days.

This patent is subject to a terminal disclaimer.

(21) Appl. No.: 12/182,083

(22) Filed: Jul. 29, 2008

(65) Prior Publication Data
US 2008/0287766 A1 Nov. 20, 2008

Related U.S. Application Data

(62) Division of application No. 10/991,966, filed on Nov. 17, 2004, now Pat. No. 7,519,408.

(60) Provisional application No. 60/523,840, filed on Nov. 19, 2003, provisional application No. 60/587,787, filed on Jul. 13, 2004, provisional application No. 60/614,683, filed on Sep. 30, 2004.

(51) Int. Cl.
*A61B 5/00* (2006.01)
(52) U.S. Cl. ........................................ 600/365; 600/347
(58) Field of Classification Search .................. 600/347, 600/365
See application file for complete search history.

(56) References Cited

U.S. PATENT DOCUMENTS

| | | | |
|---|---|---|---|
| 2,719,797 | A | 10/1955 | Rosenblatt et al. |
| 3,210,578 | A | 10/1965 | Sherer |
| 3,219,533 | A | 11/1965 | Mullins |
| 3,381,371 | A | 5/1968 | Russell |
| 3,780,727 | A | 12/1973 | King |
| 3,826,244 | A | 7/1974 | Salcman et al. |
| 3,898,984 | A | 8/1975 | Mandel et al. |

(Continued)

FOREIGN PATENT DOCUMENTS

EP 0 098 592 A2 1/1984

(Continued)

OTHER PUBLICATIONS

Aalders et al. 1991. Development of a wearable glucose sensor; studies in healthy volunteers and in diabetic patients. The International Journal of Artificial Organs 14(2):102-108.

(Continued)

*Primary Examiner* — Robert L Nasser
*Assistant Examiner* — Karen E Toth
(74) *Attorney, Agent, or Firm* — Knobbe Martens Olson & Bear LLP

(57) ABSTRACT

A system is provided for monitoring glucose in a host, including a continuous glucose sensor that produces a data stream indicative of a host's glucose concentration and an integrated receiver that receives the data stream from the continuous glucose sensor and calibrates the data stream using a single point glucose monitor that is integral with the integrated receiver. The integrated receiver obtains a glucose value from the single point glucose monitor, calibrates the sensor data stream received from the continuous glucose sensor, and displays one or both of the single point glucose measurement values and the calibrated continuous glucose sensor values on the user interface.

14 Claims, 13 Drawing Sheets

U.S. PATENT DOCUMENTS

| | | |
|---|---|---|
| 3,929,971 A | 12/1975 | Roy |
| 3,943,918 A | 3/1976 | Lewis |
| 3,957,613 A | 5/1976 | Macur |
| 3,979,274 A | 9/1976 | Newman |
| 4,052,754 A | 10/1977 | Homsy |
| 4,076,656 A | 2/1978 | White et al. |
| 4,240,889 A | 12/1980 | Yoda et al. |
| 4,253,469 A | 3/1981 | Aslan |
| 4,374,013 A | 2/1983 | Enfors |
| 4,403,984 A | 9/1983 | Ash et al. |
| 4,415,666 A | 11/1983 | D'Orazio et al. |
| 4,431,004 A | 2/1984 | Bessman et al. |
| 4,436,094 A | 3/1984 | Cerami |
| 4,442,841 A | 4/1984 | Uehara et al. |
| 4,454,295 A | 6/1984 | Wittmann et al. |
| 4,477,314 A | 10/1984 | Richter et al. |
| 4,494,950 A | 1/1985 | Fischell |
| 4,506,680 A | 3/1985 | Stokes |
| RE31,916 E | 6/1985 | Oswin et al. |
| 4,554,927 A | 11/1985 | Fussell |
| 4,577,642 A | 3/1986 | Stokes |
| 4,583,976 A | 4/1986 | Ferguson |
| RE32,361 E | 2/1987 | Duggan |
| 4,655,880 A | 4/1987 | Liu |
| 4,671,288 A | 6/1987 | Gough |
| 4,680,268 A | 7/1987 | Clark, Jr. |
| 4,703,756 A | 11/1987 | Gough et al. |
| 4,711,251 A | 12/1987 | Stokes |
| 4,721,677 A | 1/1988 | Clark |
| 4,731,726 A | 3/1988 | Allen |
| 4,750,496 A | 6/1988 | Reinhart et al. |
| 4,757,022 A | 7/1988 | Shults et al. |
| 4,759,828 A | 7/1988 | Young et al. |
| 4,781,798 A | 11/1988 | Gough |
| 4,787,398 A | 11/1988 | Garcia et al. |
| 4,805,624 A | 2/1989 | Yao et al. |
| 4,805,625 A | 2/1989 | Wyler |
| 4,831,070 A | 5/1989 | McInally et al. |
| 4,832,034 A | 5/1989 | Pizziconi |
| 4,849,458 A | 7/1989 | Reed et al. |
| 4,852,573 A | 8/1989 | Kennedy |
| 4,858,615 A | 8/1989 | Meinema |
| 4,883,057 A | 11/1989 | Broderick |
| 4,890,620 A | 1/1990 | Gough |
| 4,890,621 A | 1/1990 | Hakky |
| 4,919,141 A | 4/1990 | Zier et al. |
| 4,927,516 A | 5/1990 | Yamaguchi et al. |
| 4,944,299 A | 7/1990 | Silvian |
| 4,953,552 A | 9/1990 | DeMarzo |
| 4,974,929 A | 12/1990 | Curry |
| 4,975,636 A | 12/1990 | Desautels |
| 4,986,671 A | 1/1991 | Sun et al. |
| 4,988,341 A | 1/1991 | Columbus et al. |
| 4,992,794 A | 2/1991 | Brouwers |
| 4,994,167 A | 2/1991 | Shults et al. |
| 5,002,572 A | 3/1991 | Picha |
| 5,030,333 A | 7/1991 | Clark, Jr. |
| 5,034,112 A | 7/1991 | Murase et al. |
| 5,050,612 A | 9/1991 | Matsumura |
| 5,068,536 A | 11/1991 | Rosenthal |
| 5,077,476 A | 12/1991 | Rosenthal |
| 5,097,834 A | 3/1992 | Skrabal |
| 5,101,814 A | 4/1992 | Palti |
| 5,108,819 A | 4/1992 | Heller et al. |
| 5,137,028 A | 8/1992 | Nishimura |
| 5,140,985 A | 8/1992 | Schroeder et al. |
| 5,160,418 A | 11/1992 | Mullen |
| 5,165,407 A | 11/1992 | Wilson et al. |
| 5,190,041 A | 3/1993 | Palti |
| 5,198,771 A | 3/1993 | Fidler et al. |
| 5,208,147 A | 5/1993 | Kagenow et al. |
| 5,243,983 A | 9/1993 | Tarr et al. |
| 5,249,576 A | 10/1993 | Goldberger et al. |
| 5,262,305 A | 11/1993 | Heller et al. |
| 5,264,104 A | 11/1993 | Gregg et al. |
| 5,266,179 A | 11/1993 | Nankai et al. |
| 5,269,891 A | 12/1993 | Colin |
| 5,281,319 A | 1/1994 | Kaneko et al. |
| 5,282,848 A | 2/1994 | Schmitt |
| 5,284,140 A | 2/1994 | Allen et al. |
| 5,284,570 A | 2/1994 | Savage et al. |
| 5,287,753 A | 2/1994 | Routh et al. |
| 5,299,571 A | 4/1994 | Mastrototaro |
| 5,307,263 A | 4/1994 | Brown |
| 5,312,361 A | 5/1994 | Zadini et al. |
| 5,316,008 A | 5/1994 | Suga et al. |
| 5,322,063 A | 6/1994 | Allen et al. |
| 5,324,322 A | 6/1994 | Grill et al. |
| 5,330,634 A | 7/1994 | Wong et al. |
| 5,331,555 A | 7/1994 | Hashimoto et al. |
| 5,337,747 A | 8/1994 | Neftel |
| 5,343,869 A | 9/1994 | Pross et al. |
| 5,352,351 A | 10/1994 | White |
| 5,354,449 A | 10/1994 | Band et al. |
| 5,368,224 A | 11/1994 | Richardson et al. |
| 5,372,133 A | 12/1994 | Hogen Esch |
| 5,376,070 A | 12/1994 | Purvis et al. |
| 5,390,671 A | 2/1995 | Lord et al. |
| 5,391,250 A | 2/1995 | Cheney, II et al. |
| 5,411,647 A | 5/1995 | Johnson et al. |
| 5,411,866 A | 5/1995 | Luong |
| 5,426,032 A | 6/1995 | Phillips et al. |
| 5,429,735 A | 7/1995 | Johnson et al. |
| 5,431,160 A | 7/1995 | Wilkins |
| 5,434,412 A | 7/1995 | Sodickson et al. |
| 5,462,051 A | 10/1995 | Oka et al. |
| 5,462,064 A | 10/1995 | D'Angelo et al. |
| 5,466,356 A | 11/1995 | Schneider et al. |
| 5,469,846 A | 11/1995 | Khan |
| 5,474,552 A | 12/1995 | Palti |
| 5,476,776 A | 12/1995 | Wilkins |
| 5,482,008 A | 1/1996 | Stafford et al. |
| 5,482,473 A | 1/1996 | Lord et al. |
| 5,484,404 A | 1/1996 | Schulman et al. |
| 5,494,562 A | 2/1996 | Maley et al. |
| 5,497,772 A | 3/1996 | Schulman et al. |
| 5,502,396 A | 3/1996 | Desarzens et al. |
| 5,507,288 A | 4/1996 | Bocker et al. |
| 5,513,636 A | 5/1996 | Palti |
| 5,518,601 A | 5/1996 | Foos et al. |
| 5,531,679 A | 7/1996 | Schulman et al. |
| 5,531,878 A | 7/1996 | Vadgama et al. |
| 5,540,828 A | 7/1996 | Yacynych |
| 5,553,616 A | 9/1996 | Ham et al. |
| 5,568,806 A | 10/1996 | Cheney, II et al. |
| 5,569,186 A | 10/1996 | Lord et al. |
| 5,582,184 A | 12/1996 | Erickson et al. |
| 5,584,813 A | 12/1996 | Livingston et al. |
| 5,586,553 A | 12/1996 | Halili et al. |
| 5,589,133 A | 12/1996 | Suzuki |
| 5,611,900 A | 3/1997 | Worden |
| 5,628,890 A | 5/1997 | Carter et al. |
| 5,653,863 A | 8/1997 | Genshaw et al. |
| 5,660,163 A | 8/1997 | Schulman et al. |
| 5,676,820 A | 10/1997 | Wang et al. |
| 5,682,884 A | 11/1997 | Hill |
| 5,695,623 A | 12/1997 | Michel et al. |
| 5,696,314 A | 12/1997 | McCaffrey et al. |
| 5,711,861 A | 1/1998 | Ward et al. |
| 5,714,123 A | 2/1998 | Sohrab |
| 5,730,654 A | 3/1998 | Brown |
| 5,743,262 A | 4/1998 | Lepper, Jr. et al. |
| 5,749,832 A | 5/1998 | Vadgama et al. |
| 5,749,907 A | 5/1998 | Mann |
| 5,791,344 A | 8/1998 | Schulman et al. |
| 5,795,774 A | 8/1998 | Matsumoto et al. |
| 5,800,420 A | 9/1998 | Gross |
| 5,806,517 A | 9/1998 | Gerhardt et al. |
| 5,807,375 A | 9/1998 | Gross et al. |
| 5,814,599 A | 9/1998 | Mitragotri et al. |
| 5,820,622 A | 10/1998 | Gross et al. |
| 5,822,715 A | 10/1998 | Worthington et al. |
| 5,836,887 A | 11/1998 | Oka et al. |
| 5,836,989 A | 11/1998 | Shelton |
| 5,840,148 A | 11/1998 | Campbell et al. |
| 5,861,019 A | 1/1999 | Sun et al. |
| 5,871,514 A | 2/1999 | Wiklund et al. |

| | | | |
|---|---|---|---|
| 5,882,494 A | 3/1999 | Van Antwerp |
| 5,895,235 A | 4/1999 | Droz |
| 5,897,578 A | 4/1999 | Wiklund et al. |
| 5,899,855 A | 5/1999 | Brown |
| 5,904,708 A | 5/1999 | Goedeke |
| 5,913,998 A | 6/1999 | Butler et al. |
| 5,914,026 A | 6/1999 | Blubaugh, Jr. et al. |
| 5,919,215 A | 7/1999 | Wiklund et al. |
| 5,931,814 A | 8/1999 | Alex et al. |
| 5,933,136 A | 8/1999 | Brown |
| 5,944,661 A | 8/1999 | Swette et al. |
| 5,954,643 A | 9/1999 | Van Antwerp et al. |
| 5,954,954 A | 9/1999 | Houck et al. |
| 5,957,854 A | 9/1999 | Besson et al. |
| 5,961,451 A | 10/1999 | Reber et al. |
| 5,963,132 A | 10/1999 | Yoakum |
| 5,964,993 A | 10/1999 | Blubaugh et al. |
| 5,965,380 A | 10/1999 | Heller et al. |
| 5,971,922 A | 10/1999 | Arita et al. |
| 5,976,085 A | 11/1999 | Kimball et al. |
| 5,995,860 A | 11/1999 | Sun et al. |
| 6,001,067 A | 12/1999 | Shults et al. |
| 6,011,984 A | 1/2000 | Van Antwerp et al. |
| 6,016,448 A | 1/2000 | Busacker et al. |
| 6,027,445 A | 2/2000 | Von Bahr |
| 6,036,924 A | 3/2000 | Simons et al. |
| 6,049,727 A | 4/2000 | Crothall |
| 6,059,946 A | 5/2000 | Yukawa et al. |
| 6,081,735 A | 6/2000 | Diab et al. |
| 6,081,736 A | 6/2000 | Colvin et al. |
| 6,083,523 A | 7/2000 | Dionne et al. |
| 6,088,608 A | 7/2000 | Schulman et al. |
| 6,091,975 A | 7/2000 | Daddona et al. |
| 6,093,172 A | 7/2000 | Funderburk et al. |
| 6,107,083 A | 8/2000 | Collins et al. |
| 6,117,290 A | 9/2000 | Say |
| 6,122,536 A | 9/2000 | Sun et al. |
| 6,123,827 A | 9/2000 | Wong et al. |
| 6,135,978 A | 10/2000 | Houben et al. |
| 6,144,869 A | 11/2000 | Berner et al. |
| 6,162,611 A | 12/2000 | Heller et al. |
| 6,168,568 B1 | 1/2001 | Gavriely |
| 6,169,155 B1 | 1/2001 | Alvarez et al. |
| 6,175,752 B1 * | 1/2001 | Say et al. ............... 600/345 |
| 6,180,416 B1 | 1/2001 | Kurnik et al. |
| 6,192,891 B1 | 2/2001 | Gravel et al. |
| 6,201,980 B1 | 3/2001 | Darrow et al. |
| 6,201,993 B1 | 3/2001 | Kruse et al. |
| 6,208,894 B1 | 3/2001 | Schulman et al. |
| 6,212,416 B1 | 4/2001 | Ward et al. |
| 6,212,424 B1 | 4/2001 | Robinson |
| 6,223,083 B1 | 4/2001 | Rosar |
| 6,230,059 B1 | 5/2001 | Duffin |
| 6,233,080 B1 | 5/2001 | Brenner et al. |
| 6,233,471 B1 | 5/2001 | Berner et al. |
| 6,248,067 B1 | 6/2001 | Causey, III et al. |
| 6,256,522 B1 | 7/2001 | Schultz |
| 6,259,937 B1 | 7/2001 | Schulman et al. |
| 6,272,364 B1 | 8/2001 | Kurnik |
| 6,272,480 B1 | 8/2001 | Tresp et al. |
| 6,275,717 B1 | 8/2001 | Gross et al. |
| 6,284,478 B1 | 9/2001 | Heller et al. |
| 6,299,578 B1 | 10/2001 | Kurnik et al. |
| 6,302,855 B1 | 10/2001 | Lav et al. |
| 6,309,351 B1 | 10/2001 | Kurnik et al. |
| 6,309,884 B1 | 10/2001 | Cooper et al. |
| 6,315,738 B1 | 11/2001 | Nishikawa et al. |
| 6,326,160 B1 | 12/2001 | Dunn et al. |
| 6,329,161 B1 | 12/2001 | Heller et al. |
| 6,329,929 B1 | 12/2001 | Weijand et al. |
| 6,330,464 B1 | 12/2001 | Colvin, Jr. et al. |
| 6,343,225 B1 | 1/2002 | Clark, Jr. |
| 6,356,776 B1 | 3/2002 | Berner et al. |
| 6,366,794 B1 | 4/2002 | Moussy et al. |
| 6,370,941 B2 | 4/2002 | Nakamura |
| 6,379,301 B1 | 4/2002 | Worthington et al. |
| 6,379,317 B1 | 4/2002 | Kintzig et al. |
| 6,406,066 B1 | 6/2002 | Uegane |
| 6,416,651 B1 | 7/2002 | Millar |
| 6,424,847 B1 | 7/2002 | Mastrototaro et al. |
| 6,461,496 B1 | 10/2002 | Feldman et al. |
| 6,464,849 B1 | 10/2002 | Say et al. |
| 6,466,810 B1 | 10/2002 | Ward et al. |
| 6,471,689 B1 | 10/2002 | Joseph et al. |
| 6,475,750 B1 | 11/2002 | Han et al. |
| 6,477,392 B1 | 11/2002 | Honigs et al. |
| 6,477,395 B2 | 11/2002 | Schulman et al. |
| 6,484,046 B1 | 11/2002 | Say et al. |
| 6,510,329 B2 | 1/2003 | Heckel |
| 6,512,939 B1 | 1/2003 | Colvin et al. |
| 6,526,298 B1 | 2/2003 | Khalil et al. |
| 6,527,729 B1 | 3/2003 | Turcott |
| 6,534,711 B1 | 3/2003 | Pollack |
| 6,544,212 B2 | 4/2003 | Galley et al. |
| 6,546,268 B1 | 4/2003 | Ishikawa et al. |
| 6,546,269 B1 | 4/2003 | Kurnik |
| 6,551,496 B1 | 4/2003 | Moles et al. |
| 6,553,241 B2 | 4/2003 | Mannheimer et al. |
| 6,553,244 B2 | 4/2003 | Lesho et al. |
| 6,558,320 B1 * | 5/2003 | Causey et al. ............... 600/300 |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,565,509 B1 | 5/2003 | Say et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,579,498 B1 | 6/2003 | Eglise |
| 6,579,690 B1 | 6/2003 | Bonnecaze et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,595,919 B2 | 7/2003 | Berner et al. |
| 6,605,072 B2 | 8/2003 | Struys et al. |
| 6,607,658 B1 | 8/2003 | Heller et al. |
| 6,612,984 B1 | 9/2003 | Kerr |
| 6,613,379 B2 | 9/2003 | Ward et al. |
| 6,618,934 B1 | 9/2003 | Feldman et al. |
| 6,633,772 B2 | 10/2003 | Ford et al. |
| 6,641,533 B2 | 11/2003 | Causey et al. |
| 6,648,821 B2 | 11/2003 | Lebel et al. |
| 6,654,625 B1 | 11/2003 | Say et al. |
| 6,673,022 B1 | 1/2004 | Bobo et al. |
| 8,673,598 | 1/2004 | Sayler et al. |
| 6,694,191 B2 | 2/2004 | Starkweather et al. |
| 6,699,188 B2 | 3/2004 | Wessel |
| 6,699,383 B2 | 3/2004 | Lemire et al. |
| 6,702,857 B2 | 3/2004 | Brauker et al. |
| 6,702,972 B1 | 3/2004 | Markle |
| 6,721,587 B2 | 4/2004 | Gough |
| 6,731,976 B2 | 5/2004 | Penn et al. |
| 6,740,075 B2 | 5/2004 | Lebel et al. |
| 6,741,877 B1 | 5/2004 | Shults et al. |
| 6,743,635 B2 | 6/2004 | Neel et al. |
| 6,773,565 B2 | 8/2004 | Kunimoto et al. |
| 6,802,957 B2 | 10/2004 | Jung et al. |
| 6,809,653 B1 | 10/2004 | Mann et al. |
| 6,810,290 B2 | 10/2004 | Lebel et al. |
| 6,813,519 B2 | 11/2004 | Lebel et al. |
| 6,862,465 B2 | 3/2005 | Shults et al. |
| 6,869,413 B2 | 3/2005 | Langley et al. |
| 6,893,552 B1 | 5/2005 | Wang et al. |
| 6,895,263 B2 | 5/2005 | Shin et al. |
| 6,925,393 B1 | 8/2005 | Kalatz et al. |
| 6,931,327 B2 | 8/2005 | Goode et al. |
| 6,952,604 B2 | 10/2005 | DeNuzzio et al. |
| 6,965,791 B1 | 11/2005 | Hitchcock et al. |
| 6,998,247 B2 * | 2/2006 | Monfre et al. ............... 435/14 |
| 7,011,630 B2 | 3/2006 | Desai et al. |
| 7,025,743 B2 | 4/2006 | Mann et al. |
| 7,029,444 B2 | 4/2006 | Shin et al. |
| 7,058,437 B2 | 6/2006 | Buse et al. |
| 7,060,059 B2 | 6/2006 | Keith et al. |
| 7,074,307 B2 | 7/2006 | Simpson et al. |
| 7,081,195 B2 | 7/2006 | Simpson et al. |
| 7,098,803 B2 | 8/2006 | Mann et al. |
| 7,134,999 B2 | 11/2006 | Brauker et al. |

| Patent/Pub No. | Date | Inventor |
|---|---|---|
| 7,169,289 B2 | 1/2007 | Schulein et al. |
| 7,225,535 B2 | 6/2007 | Feldman et al. |
| 7,229,288 B2 | 6/2007 | Stuart et al. |
| 7,261,690 B2 | 8/2007 | Teller et al. |
| 7,267,665 B2 | 9/2007 | Steil et al. |
| 7,276,029 B2 | 10/2007 | Goode et al. |
| 7,278,983 B2 * | 10/2007 | Ireland et al. .................. 604/66 |
| 7,295,867 B2 | 11/2007 | Berner et al. |
| 7,354,420 B2 | 4/2008 | Steil et al. |
| 7,359,723 B2 | 4/2008 | Jones |
| 7,402,153 B2 | 7/2008 | Steil et al. |
| 7,417,164 B2 | 8/2008 | Suri |
| 7,426,408 B2 | 9/2008 | DeNuzzio et al. |
| 7,519,408 B2 * | 4/2009 | Rasdal et al. .................. 600/347 |
| 7,519,478 B2 | 4/2009 | Bartkowiak et al. |
| 7,523,004 B2 | 4/2009 | Bartkowiak et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,618,368 B2 | 11/2009 | Brown |
| 7,624,028 B1 | 11/2009 | Brown |
| 7,640,032 B2 | 12/2009 | Jones |
| 7,640,048 B2 | 12/2009 | Dobbles et al. |
| 7,657,297 B2 | 2/2010 | Simpson et al. |
| 2001/0016682 A1 | 8/2001 | Berner et al. |
| 2001/0041830 A1 | 11/2001 | Varalli et al. |
| 2001/0051768 A1 | 12/2001 | Schulman et al. |
| 2002/0019022 A1 | 2/2002 | Dunn et al. |
| 2002/0026111 A1 | 2/2002 | Ackerman |
| 2002/0042090 A1 | 4/2002 | Heller et al. |
| 2002/0042561 A1 | 4/2002 | Schulman et al. |
| 2002/0043471 A1 | 4/2002 | Ikeda et al. |
| 2002/0045808 A1 | 4/2002 | Ford et al. |
| 2002/0065453 A1 | 5/2002 | Lesho et al. |
| 2002/0068860 A1 | 6/2002 | Clark, Jr. |
| 2002/0084196 A1 | 7/2002 | Liamos et al. |
| 2002/0099282 A1 | 7/2002 | Knobbe et al. |
| 2002/0099997 A1 | 7/2002 | Piret |
| 2002/0111547 A1 | 8/2002 | Knobbe et al. |
| 2002/0119711 A1 | 8/2002 | Van Antwerp et al. |
| 2002/0155615 A1 | 10/2002 | Novikov et al. |
| 2002/0161288 A1 | 10/2002 | Shin et al. |
| 2002/0188185 A1 | 12/2002 | Sohrab |
| 2002/0198513 A1 | 12/2002 | Lebel et al. |
| 2003/0006669 A1 | 1/2003 | Pei et al. |
| 2003/0023171 A1 | 1/2003 | Sato et al. |
| 2003/0023317 A1 | 1/2003 | Brauker et al. |
| 2003/0028089 A1 | 2/2003 | Galley et al. |
| 2003/0032874 A1 | 2/2003 | Rhodes et al. |
| 2003/0050546 A1 | 3/2003 | Desai et al. |
| 2003/0070548 A1 | 4/2003 | Clausen |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0097082 A1 | 5/2003 | Purdy et al. |
| 2003/0100821 A1 | 5/2003 | Heller et al. |
| 2003/0125612 A1 | 7/2003 | Fox et al. |
| 2003/0125613 A1 | 7/2003 | Enegren et al. |
| 2003/0130616 A1 | 7/2003 | Steil et al. |
| 2003/0134347 A1 | 7/2003 | Heller et al. |
| 2003/0176183 A1 | 9/2003 | Drucker et al. |
| 2003/0187338 A1 | 10/2003 | Say et al. |
| 2003/0188427 A1 | 10/2003 | Say et al. |
| 2003/0211625 A1 | 11/2003 | Cohan |
| 2003/0212317 A1 | 11/2003 | Kovatchev et al. |
| 2003/0212346 A1 | 11/2003 | Yuzhakov et al. |
| 2003/0212347 A1 | 11/2003 | Sohrab |
| 2003/0235817 A1 | 12/2003 | Bartkowiak et al. |
| 2004/0011671 A1 | 1/2004 | Shults et al. |
| 2004/0015063 A1 | 1/2004 | DeNuzzio et al. |
| 2004/0015134 A1 | 1/2004 | Lavi et al. |
| 2004/0024327 A1 | 2/2004 | Brodnick |
| 2004/0039298 A1 | 2/2004 | Abreu |
| 2004/0045879 A1 | 3/2004 | Shults et al. |
| 2004/0068230 A1 | 4/2004 | Estes et al. |
| 2004/0074785 A1 | 4/2004 | Holker |
| 2004/0078219 A1 | 4/2004 | Kaylor |
| 2004/0106857 A1 | 6/2004 | Gough |
| 2004/0143173 A1 | 7/2004 | Reghabi et al. |
| 2004/0152187 A1 | 8/2004 | Haight et al. |
| 2004/0152622 A1 | 8/2004 | Keith et al. |
| 2004/0167801 A1 | 8/2004 | Say et al. |
| 2004/0173472 A1 | 9/2004 | Jung et al. |
| 2004/0186362 A1 | 9/2004 | Brauker et al. |
| 2004/0186365 A1 | 9/2004 | Jin et al. |
| 2004/0199059 A1 | 10/2004 | Brauker et al. |
| 2004/0254433 A1 | 12/2004 | Bandis |
| 2005/0010265 A1 | 1/2005 | Baru Fassio et al. |
| 2005/0026689 A1 | 2/2005 | Marks |
| 2005/0027180 A1 | 2/2005 | Goode et al. |
| 2005/0027181 A1 | 2/2005 | Goode et al. |
| 2005/0027182 A1 | 2/2005 | Siddiqui et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0043598 A1 | 2/2005 | Goode et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056552 A1 | 3/2005 | Simpson et al. |
| 2005/0090607 A1 | 4/2005 | Tapsak et al. |
| 2005/0096519 A1 | 5/2005 | DeNuzzio et al. |
| 2005/0101847 A1 | 5/2005 | Routt et al. |
| 2005/0112169 A1 | 5/2005 | Brauker et al. |
| 2005/0113653 A1 | 5/2005 | Fox et al. |
| 2005/0115832 A1 | 6/2005 | Simpson et al. |
| 2005/0121322 A1 | 6/2005 | Say |
| 2005/0139489 A1 | 6/2005 | Davies et al. |
| 2005/0143635 A1 | 6/2005 | Kamath et al. |
| 2005/0143675 A1 | 6/2005 | Neel et al. |
| 2005/0154271 A1 | 7/2005 | Rasdal et al. |
| 2005/0182451 A1 | 8/2005 | Griffin et al. |
| 2005/0187720 A1 | 8/2005 | Goode et al. |
| 2005/0192557 A1 | 9/2005 | Brauker et al. |
| 2005/0203360 A1 | 9/2005 | Brauker et al. |
| 2005/0211571 A1 | 9/2005 | Schulein et al. |
| 2005/0215872 A1 | 9/2005 | Berner et al. |
| 2005/0239154 A1 * | 10/2005 | Feldman et al. ................. 435/14 |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2005/0261563 A1 | 11/2005 | Zhou et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0100588 A1 | 5/2006 | Brunnberg et al. |
| 2006/0183984 A1 | 8/2006 | Dobbles et al. |
| 2006/0183985 A1 | 8/2006 | Brister et al. |
| 2006/0195029 A1 | 8/2006 | Shults et al. |
| 2006/0222566 A1 | 10/2006 | Brauker et al. |
| 2006/0258929 A1 | 11/2006 | Goode et al. |
| 2007/0016381 A1 | 1/2007 | Kamath et al. |
| 2007/0027385 A1 | 2/2007 | Brister et al. |
| 2007/0032706 A1 | 2/2007 | Kamath et al. |
| 2007/0038044 A1 | 2/2007 | Dobbles et al. |
| 2007/0049873 A1 | 3/2007 | Hansen et al. |
| 2007/0066873 A1 | 3/2007 | Kamath et al. |
| 2007/0203410 A1 | 8/2007 | Say et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |

| | | |
|---|---|---|
| 2007/0213610 A1 | 9/2007 | Say et al. |
| 2007/0235331 A1 | 10/2007 | Simpson et al. |
| 2008/0021666 A1 | 1/2008 | Goode et al. |
| 2008/0033254 A1 | 2/2008 | Kamath et al. |
| 2008/0154101 A1 | 6/2008 | Jain et al. |
| 2008/0183061 A1 | 7/2008 | Goode et al. |
| 2008/0183399 A1 | 7/2008 | Goode et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0188731 A1 | 8/2008 | Brister et al. |
| 2008/0189051 A1 | 8/2008 | Goode et al. |
| 2008/0194837 A1 | 8/2008 | Kim et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0195967 A1 | 8/2008 | Goode et al. |
| 2008/0208025 A1 | 8/2008 | Shults et al. |
| 2008/0210557 A1 | 9/2008 | Heller et al. |
| 2008/0214915 A1 | 9/2008 | Brister et al. |
| 2008/0262469 A1 | 10/2008 | Brister et al. |
| 2008/0287764 A1 | 11/2008 | Rasdal et al. |
| 2008/0287766 A1 | 11/2008 | Rasdal et al. |
| 2008/0296155 A1 | 12/2008 | Shults et al. |
| 2008/0305009 A1 | 12/2008 | Gamsey et al. |
| 2008/0305506 A1 | 12/2008 | Suri |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode et al. |
| 2009/0018418 A1 | 1/2009 | Markle et al. |
| 2009/0018426 A1 | 1/2009 | Markle et al. |
| 2009/0036758 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0061528 A1 | 3/2009 | Suri |
| 2009/0062635 A1 | 3/2009 | Brauker et al. |
| 2009/0076356 A1 | 3/2009 | Simpson |
| 2009/0076360 A1 | 3/2009 | Brister et al. |
| 2009/0076361 A1 | 3/2009 | Kamath et al. |
| 2009/0081803 A1 | 3/2009 | Gamsey et al. |
| 2009/0099434 A1 | 4/2009 | Liu et al. |
| 2009/0124877 A1 | 5/2009 | Goode, Jr. et al. |
| 2009/0124878 A1 | 5/2009 | Goode, Jr. et al. |
| 2009/0156924 A1 | 6/2009 | Shariati et al. |
| 2009/0177143 A1 | 7/2009 | Markle et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0264719 A1 | 10/2009 | Markle et al. |
| 2009/0287074 A1 | 11/2009 | Shults et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0022855 A1 | 1/2010 | Brauker et al. |
| 2010/0030053 A1 | 2/2010 | Goode, Jr. et al. |
| 2010/0030484 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036224 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0076283 A1 | 3/2010 | Simpson et al. |
| 2010/0081908 A1 | 4/2010 | Dobbles et al. |
| 2010/0161269 A1 | 6/2010 | Kamath et al. |

FOREIGN PATENT DOCUMENTS

| | | |
|---|---|---|
| EP | 0 127 958 | 12/1984 |
| EP | 0 320 109 | 6/1989 |
| EP | 0 353 328 | 2/1990 |
| EP | 0 390 390 | 10/1990 |
| EP | 0 396 788 | 11/1990 |
| EP | 0 534 074 A1 | 3/1993 |
| EP | 0 563 795 | 10/1993 |
| EP | 0 817 809 | 1/1998 |
| EP | 0 838 230 | 4/1998 |
| EP | 0 880 936 | 12/1998 |
| EP | 0 885 932 | 12/1998 |
| EP | 0 967 788 | 12/1999 |
| EP | 1 077 634 | 2/2001 |
| EP | 1 078 258 B1 | 2/2001 |
| FR | 2656423 | 6/1991 |
| FR | 2 760 962 | 9/1998 |
| GB | 1 442 303 | 7/1976 |
| GB | 2149918 | 6/1985 |
| JP | 62083649 | 4/1987 |
| JP | 62083849 | 4/1987 |
| JP | 07-083871 | 3/1995 |
| JP | 2002-189015 | 7/2002 |
| WO | WO 89/02720 | 4/1989 |
| WO | WO 90/00738 | 1/1990 |
| WO | WO 90/10861 | 9/1990 |
| WO | WO 92/13271 | 8/1992 |
| WO | WO 93/14693 | 8/1993 |
| WO | WO 94/22367 | 10/1994 |
| WO | WO 95/07109 | 3/1995 |
| WO | WO 96/14026 | 5/1996 |
| WO | WO 96/25089 | 8/1996 |
| WO | WO 96/30431 | 10/1996 |
| WO | WO 97/01986 | 1/1997 |
| WO | WO 97/06727 | 2/1997 |
| WO | WO 97/28737 | 8/1997 |
| WO | WO 98/24358 | 6/1998 |
| WO | WO 99/56613 | 4/1999 |
| WO | WO 99/48419 | 9/1999 |
| WO | WO 99/58051 | 11/1999 |
| WO | WO 99/58973 | 11/1999 |
| WO | WO 00/12720 | 3/2000 |
| WO | WO 00/19887 | 4/2000 |
| WO | WO 00/32098 | 6/2000 |
| WO | WO 00/33065 | 6/2000 |
| WO | WO 00/49941 | 8/2000 |
| WO | WO 00/59373 | 10/2000 |
| WO | WO 00/074753 | 12/2000 |
| WO | WO 01/12158 A1 | 2/2001 |
| WO | WO 01/20019 | 3/2001 |
| WO | WO 01/20334 | 3/2001 |
| WO | WO 01/34243 | 5/2001 |
| WO | WO 01/52727 A1 | 7/2001 |
| WO | WO 01/58348 A2 | 8/2001 |
| WO | WO 01/68901 | 9/2001 |
| WO | WO 01/69222 | 9/2001 |
| WO | WO 01/88524 | 11/2001 |
| WO | WO 01/88534 A2 | 11/2001 |
| WO | WO 02/24065 A1 | 3/2002 |
| WO | WO 00/78210 | 5/2002 |
| WO | WO 02/082989 | 10/2002 |
| WO | WO 02/100266 | 12/2002 |
| WO | WO 2005/011489 | 2/2005 |
| WO | WO 2006/017358 | 2/2006 |
| WO | WO 2006/105146 | 10/2006 |
| WO | WO 2008/076868 | 6/2008 |

OTHER PUBLICATIONS

Abe et al. 1992. Characterization of glucose microsensors for intracellular measurements. Anal. Chem. 64(18):2160-2163.
Abel et al. 1984. Experience with an implantable glucose sensor as a prerequisite of an artificial beta cell, Biomed. Biochim. Acta 43(5):577-584.
Alcock & Turner. 1994. Continuous Analyte Monitoring to Aid Clinical Practice. IEEE Engineering in Med. & Biol. Mag. 13:319-325.
American Heritage Dictionary, 4th Edition. 2000. Houghton Mifflin Company, p. 82.
Amin et al. 2003. Hypoglycemia prevalence in prepubertal children with type 1 diabetes on standard insulin regimen: Use of continuous glucose monitoring system. Diabetes Care 26(3):662-667.
Answers.com. "xenogenic." The American Heritage Stedman's Medical Dictionary. Houghton Mifflin Company, 2002. Answers.com Nov. 7, 2006 http://www. Answers.com/topic/xenogenic.
Atanasov et al. 1994. Biosensor for continuous glucose monitoring. Biotechnology and Bioengineering 43:262-266.
Atanasov et al. 1997. Implantation of a refillable glucose monitoring-telemetry device. Biosens Bioelectron 12:669-680.
Bailey et al. 2007. Reduction in hemoglobin A1c with real-time continuous glucose monitoring: results from a 12-week observational study. Diabetes Technology & Therapeutics 9(3):203-210.
Baker et al. 1993. Dynamic concentration challenges for biosensor characterization. Biosensors & Bioelectronics 8:433-441.
Beach et al. 1999. Subminiature implantable potentiostat and modified commercial telemetry device for remote glucose monitoring. IEEE Transactions on Instrumentation and Measurement 48(6):1239-1245.
Bessman et al., Progress toward a glucose sensor for the artificial pancreas, Proceedings of a Workshop on Ion-Selective Microelectrodes, Jun. 4-5, 1973, Boston, MA, 189-197.
Bindra et al. 1989. Pulsed amperometric detection of glucose in biological fluids at a surface-modified gold electrode. Anal Chem 61:2566-2570.
Bisenberger et al. 1995. A triple-step potential waveform at enzyme multisensors with thick-film gold electrodes for detection of glucose and sucrose. Sensors and Actuators, B 28:181-189.
Boedeker Plastics, Inc. 2009. Polyethylene Specifications Data Sheet, http://www.boedeker.com/polye_p.htm [Aug. 19, 2009 3:36:33 PM].
Boland et al. 2001. Limitations of conventional methods of self-monitoring of blood glucose. Diabetes Care 24(11):1858-1862.
Bolinder et al. 1997. Self-monitoring of blood glucose in type 1 diabetic patients: Comparison with continuous microdialysis measurements of glucose in subcutaneous adipose tissue during ordinary life conditions. Diabetes Care 20(1):64-70.
Bott, A. W. 1997. A Comparison of Cyclic Voltammetry and Cyclic Staircase Voltammetry Current Separations 16:1, 23-26.
Bott, A. 1998. Electrochemical methods for the determination of glucose. Current Separations 17(1):25-31.
Bowman, L.; Meindl, J. D. 1986. The packaging of implantable integrated sensors. IEEE Trans Biomed Eng BME33(2):248-255.
Brauker et al. Jun. 27, 1996. Local Inflammatory Response Around Diffusion Chambers Containing Xenografts Transplantation 61(12):1671-1677.
Braunwald, 2008. Biomarkers in heart failure. N. Engl. J. Med., 358: 2148-2159.
Bremer et al. 2001. Benchmark data from the literature for evaluation of new glucose sensing technologies. Diabetes Technology & Therapeutics 3(3):409-418.
Bruckel et al. 1989. In vivo measurement of subcutaneous glucose concentrations with an enzymatic glucose sensor and a wick method. Klin Wochenschr 67:491-495.
Brunstein et al. 1989. Preparation and validation of implantable electrodes for the measurement of oxygen and glucose. Biomed Biochim. Acta 48(11/12):911-917.
Cai et al. 2004. A wireless, remote query glucose biosensor based on a pH-sensitive polymer. Anal Chem 76(4):4038-4043.
Cameron et al. 1997. Micromodular Implants to provide electrical stimulation of paralyzed muscles and limbs. IEEE Transactions on Biomedical Engineering 44(9):781-790.
Campanella et al. 1993. Biosensor for direct determination of glucose and lactate in undiluted biological fluids. Biosensors & Bioelectronics 8:307-314.
Cassidy et al., Apr. 1993. Novel electrochemical device for the detection of cholesterol or glucose, Analyst, 118:415-418.
Chase et al. 2001. Continuous subcutaneous glucose monitoring in children with type 1 diabetes. Pediatrics 107:222-226.
Chen et al. 2002. Defining the period of recovery of the glucose concentration after its local perturbation by the implantation of a miniature sensor. Clin. Chem. Lab. Med. 40:786-789.
Ciba® Irgacure 2959 Photoinitiator Product Description, Ciba Specialty Chemicals Inc., Basel, Switzerland.
Claremont et al. 1986. Subcutaneous implantation of a ferrocene-mediated glucose sensor in pigs. Diabetologia 29:817-821.
Claremont et al. Jul. 1986. Potentially-implntable, ferrocene-mediated glucose sensor. J. Biomed. Eng. 8:272-274.
Clark et al., 1981. One-minute electrochemical enzymic assay for cholesterol in biological materials, Clin. Chem. 27(12):1978-1982.
Clark et al. 1987. Configurational cyclic voltammetry: increasing the specificity and reliablity of implanted electrodes, IEEE/Ninth Annual Conference of the Engineering in Medicine and Biology Society, pp. 0782-0783.
Clark et al. 1988. Long-term stability of electroenzymatic glucose sensors implanted in mice. Trans Am Soc Artif Intern Organs 34:259-265.
Clarke et al. Sep.-Oct. 1987. Evaluating Clinical Accuracy of Systems for Self-Monitoring of Blood Glucose. Diabetes Care 10(5):622-628.
CLSI. Performance metrics for continuous interstitial glucose monitoring; approved guideline, CLSI document POCT05-A. Wayne, PA: Clinical and Laboratory Standards Institute: 2008 28(33), 72 pp.
Colangelo et al. 1967. Corrosion rate measurements in vivo, Journal of Biomedical Materials Research, 1:405-414.
Colowick et al. 1976. Methods in Enzymlology, vol. XLIV, Immobilized Enzymes. New York: Academic Press.
Cox et al. 1985. Accuracy of perceiving blood glucose in IDDM. Diabetes Care 8(6):529-536.
Csoregi et al., 1994. Design, characterization, and one-point in vivo calibration of a subcutaneously implanted glucose electrode. Anal Chem. 66(19):3131-3138.
Currie et al., Novel non-intrusive trans-dermal remote wireless micro-fluidic monitoring systme applied to continuous glucose and lactate assays for casualty care and combat readiness assessment, RTO HFM Symposium, St. Pete Beach, RTO-MP-HFM-109, Aug. 1.
Danielsson et al. 1988. Enzyme thermistors, Methods in Enzymology, 137:181-197.
Dassau et al., In silico evaluation platform for artifical pancreatic β-cell development-a dynamic simulator for closed loop control with hardware-in-the-loop, Diabetes Technology & Therapeutics, 11(3):1-8, 2009.
Davis et al. 1983. Bioelectrochemical fuel cell and sensor based on a quinoprotein, alcohol dehydrogenase. Enzyme Microb. Technol., vol. 5, September, 383-388.
Deutsch et al., "Time series analysis and control of blood glucose levels in diabetic patients". Computer Methods and Programs in Biomedicine 41 (1994) 167-182.
Direct 30/30® meter (Markwell Medical) (Catalog).
Dixon et al. 2002. Characterization in vitro and in vivo of the oxygen dependence of an enzyme/polymer biosensor for monitoring brain glucose. Journal of Neuroscience Methods 119:135-142.
DuPont[1] Dimension AR® (Catalog), 1998.
Durliat et al. 1976. Spectrophotometric and electrochemical determinations of L(+)-lactate in blood by use of lactate dehydrogenase from yeast, Clin. Chem. 22(11):1802-1805.
Edwards Lifesciences. Accuracy for your and your patients. Marketing materials, 4 pp. 2002.
El Degheidy et al. 1986. Optimization of an implantable coated wire glucose sensor. J. Biomed Eng. 8: 121-129.
El-Sa'ad et al. 1990. Moisture Absorption by Epoxy Resins: the Reverse Thermal Effect. Journal of Materials Science 25:3577-3582.
Ernst et al. 2002. Reliable glucose monitoring through the use of microsystem technology. Anal. Bioanal. Chem. 373:758-761.

Fahy et al., An analysis: hyperglycemic intensive care patients need continuous glocuse monitoring—easier said than done, Journal of Diabetese Science and Technology, 2(2):201-204, Mar. 2008.

Fare et al. 1998. Functional characterization of a conducting polymer-based immunoassay system. Biosensors & Bioelectronics 13(3-4):459-470.

Feldman et al. 2003. A continuous glucose sensor based on wired enzyme technology—results from a 3-day trial in patients with type 1 diabetes. Diabetes Technol Ther 5(5):769-779.

Fischer et al. 1987. Assessment of subcutaneous glucose concentration: validation of the wick technique as a reference for implanted electrochemical sensors in normal and diabetic dogs, Diabetologia 30:940-945.

Fischer et al. 1989. Oxygen Tension at the Subcutaneous Implantation Site of Glucose Sensors. Biomed. Biochem 11/12:965-972.

Fischer et al. 1995. Hypoglycaemia-warning by means of subcutaneous electrochemical glucose sensors: an animal study, Horm. Metab. Rese. 27:53.

Freedman et al. 1991. Statistics, Second Edition, W.W. Norton & Company, p. 74.

Frohnauer et al. 2001. Graphical human insulin time-activity profiles using standardized definitions. Diabetes Technology & Therapeutics 3(3):419-429.

Gabbay et al. 2008. Optical coherence tomography-based continuous noninvasive glucose monitoring in patients with diabetes. Diab. Thechnol. & Therapeut., 10:188-193.

Ganesan et al., Gold layer-based dual crosslinking procedure of glucose oxidase with ferrocene monocarboxylic acid provides a stable biosensor, Analytical Biochemistry 343:188-191, 2005.

Ganesh et al., Evaluation of the VIA® blood chemistry monitor for glucose in healthy and diabetic volunteers, Journal of Diabetese Science and Technology, 2(2):182-193, Mar. 2008.

Garg et al. 1999. Correlation of fingerstick blood glucose measurements with GlucoWatch biographer glucose results in young subjects with type 1 diabetes. Diabetes Care 22(10):1708-1714.

Gerritsen et al. 1999. Performance of subcutaneously implanted glucose sensors for continuous monitoring. The Netherlands Journal of Medicine 54:167-179.

Gerritsen, M. 2000. Problems associated with subcutaneously implanted glucose sensors. Diabetes Care 23(2):143-145.

Gilligan et al. 1994. Evaluation of a subcutaneous glucose sensor out to 3 months in a dog model. Diabetes Care 17(8):882-887.

Godsland et al. 2001. Maximizing the Success Rate of Minimal Model Insulin Sensitivity Measurement in Humans: The Importance of Basal Glucose Levels. The Biochemical Society and the Medical Research Society, 1-9.

Gouda et al., Jul. 4, 2003. Thermal inactiviation of glucose oxidase, The Journal of Biological Chemistry, 278(27):24324-24333.

Gough et al. 2000. Immobilized glucose oxidase in implantable glucose sensor technology. Diabetes Technology & Therapeutics 2(3):377-380.

Gough et al. 2003. Frequency characterization of blood glucose dynamics. Annals of Biomedical Engineering 31:91-97.

Gross et al. 2000. Efficacy and reliability of the continuous glucose monitoring system. Diabetes Technology & Therapeutics, 2(Suppl 1):S19-26.

Gross et al. 2000. Performance evaluation of the MiniMed® continuous glucose monitoring system during patient home use. Diabetes Technology & Therapeutics 2(1):49-56.

Hall et al. 1998. Electrochemical oxidation of hydrogen peroxide at platinum electrodes. Part I: An adsorption-controlled mechanism. Electrochimica Acta, 43(5-6):579-588.

Hall et al. 1998. Electrochemical oxidation of hydrogen peroxide at platinum electrodes. Part II: Effect of potential. Electrochimica Acta 43(14-15):2015-2024.

Hall et al. 1999. Electrochemical oxidation of hydrogen peroxide at platinum electrodes. Part III: Effect of temperature. Electrochimica Acta, 44:2455-2462.

Hall et al. 1999. Electrochemical oxidation of hydrogen peroxide at platinum electrodes. Part IV: Phosphate buffer dependence. Electrochimica Acta, 44:4573-4582.

Hall et al. 2000. Electrochemical oxidation of hydrogen peroxide at platinum electrodes. Part V: Inhibition by chloride. Electrochimica Acta, 45:3573-3579.

Hamilton Syringe Selection Guide. 2006. Syringe Selection. www.hamiltoncompany.com.

Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," Diabetes C.

Heise et al. 2003. Hypoglycemia warning signal and glucose sensors: Requirements and concepts. Diabetes Technology & Therapeutics 5:563-571.

Heller, A. 2003. Plugging metal connectors into enzymes. Nat Biotechnol 21:631-2.

Hitchman, M. L. 1978. Measurement of Dissolved Oxygen. In Elving et al. (Eds.). Chemical Analysis, vol. 49, Chap. 3, pp. 34-49, 59-123. New York: John Wiley & Sons.

Hoel, Paul G. 1976. Elementary Statistics, Fourth Edition. John Wiley & Sons, Inc. pp. 113-114.

Hrapovic et al. 2003 Picoamperometric detection of glucose at ultrasmall platinum-based biosensors: preparation and characterization. Anal Chem 75:3308-3315.

http://www.merriam-webster.com/dictionary, definition for "aberrant," Aug. 19, 2008, p. 1.

Huang et al. A 0.5mV passive telemetry IC for biomedical applications. Swiss Federal Institute of Technology. 4 pp.

Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum E.

Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Compl.

Jablecki et al. 2000. Simulations of the frequency response of implantable glucose sensors. Analytical Chemistry 72:1853-1859.

Jaremko et al. 1998. Advances toward the implantable artificial pancreas for treatment of diabetes. Diabetes Care 21(3):444-450.

Jensen et al. 1997. Fast wave forms for pulsed electrochemical detection of glucose by incorporation of reductive desorption of oxidation products. Analytical Chemistry 69(9):1776-1781.

Jeong et al. 2003. In vivo calibration of the subcutaneous amperometric glucose sensors using a non-enzyme electrode. Biosensors and Bioelectronics 19:313-319.

Jeutter, D. C. 1982. A transcutaneous implanted battery recharging and biotelemeter power switching system. IEEE Trans Biomed Eng 29:314-321.

Jeutter et al. 1993. Design of a radio-linked implantable cochlear prosthesis using surface acoustic wave devices. IEEE Transactions on ultrasonics, ferroelectrics and frequency control 40(5):469-477.

Johnson (1991). "Reproducible electrodeposition of biomolecules for the fabrication of miniature electroenzymatic biosensors," Sensors and Actuators B, 5:85-89.

Joung et al. 1998. An energy transmission system for an artificial heart using leakage inductance compensation of transcutaneous transformer. IEEE Transactions on Power Electronics 13(6):1013-1022.

Jovanovic, L. 2000. The role of continuous glucose monitoring in gestational diabetes mellitus. Diabetes Technology & Therapeutics, 2 Suppl 1, S67-71.

Kacaniklic May-Jun. 1994. Electroanalysis, 6(5-6):381-390.

Kang et al. 2003. In vitro and short-term in vivo characteristics of a Kel-F thin film modified glucose sensor. Anal Sci 19:1481-1486.

Kaufman. 2000. Role of the continuous glucose monitoring system in pediatric patients. Diabetes Technology & Therapeutics 2(1):S-49-S-52.

Kaufman et al. 2001. A pilot study of the continuous glucose monitoring system. Diabetes Care 24(12):2030-2034.

Keedy et al. 1991. Determination of urate in undiluted whole blood by enzyme electrode. Biosensors & Bioelectronics, 6: 491-499.

Kerner et al. 1988. A potentially implantable enzyme electrode for amperometric measurement of glucose, Horm Metab Res Suppl. 20:8-13.

Klueh et al. 2003. Use of Vascular Endothelia Cell Growth Factor Gene Transfer to Enhance Implantable Sensor Function in Vivo, Biosensor Function and Vegf-Gene Transfer, pp. 1072-1086.

Ko, Wen H. 1985. Implantable Sensors for Closed-Loop Prosthetic Systems, Futura Pub. Co., Inc., Mt. Kisco, NY, Chapter 15:197-210.

Kondo et al. 1982. A miniature glucose sensor, implantable in the blood stream. Diabetes Care. 5(3):218-221.

Koschinsky et al. 2001. Sensors for glucose monitoring: Technical and clinical aspects. Diabetes Metab. Res. Rev. 17:113-123.

Kost et al. 1985. Glucose-sensitive membranes containing glucose oxidase: activitiy, swelling, and permeability studies, Journal of Biomedical Materials Research 19:1117-1133.

Koudelka et al. 1989. In vivo response of microfabricated glucose sensors to glycemia changes in normal rats. Biomed Biochim Acta 48(11-12):953-956.

Koudelka et al. 1991. In-vivo behaviour of hypodermically implanted microfabricated glucose sensors. Biosensors & Bioelectronics 6:31-36.

Kovatchev et al. Aug. 2004. Evaluating the accuracy of continuous glucose-monitoring sensors: continuous glucose-error grid analysis illustrated by TheraSense Freestyle Navigator data. Diabetes Care 27(8):1922-1928.

Kraver et al. 2001. A mixed-signal sensor interface microinstrument. Sensors and Actuators A 91:266-277.

Krouwer, J. S. 2002. Setting performance goals and evaluating total analytical error for diagnostic assays. Clinical Chemistry 48(6):919-927.

Kruger et al. 2000. Psychological motivation and patient education: A role for continuous glucose monitoring. Diabetes Technology & Therapeutics, 2(Suppl 1):S93-97.

Kulys et al., 1994. Carbon-paste biosensors array for long-term glucose measurement, Biosensors& Beioelectronics, 9:491-500.

Kunjan et al., Automated blood sampling and glocuse sensing in critical care settings, Journal of Diabetes Science and Technology 2(3):194-200, Mar. 2008.

Kurtz et al. 2005. Recommendations for blood pressure measurement in humans and experimental animals, Part 2: Blood pressure measurement in experimental animals, A statement for professionals from the subcommittee of professional and public education of the American Heart Association Council on High Blood Pressure Research.

LaCourse et al. 1993. Optimization of waveforms for pulsed amperometric detection of carbohydrates based on pulsed voltammetry. Analytical Chemistry 65:50-52.

Ladd et al., Structure Determination by X-ray Crystallography, 3rd ed. Plenum, 1996, Ch. 1, pp. xxi-xxiv and 1-58.

Lehmann et al. May 1994. Retrospective valication of a physiological model of glucose-iunsulin interaaction in tyhpe 1 diabetes mellitus, Med. Eng. Phys. 16:193-202.

Lewandowski et al. 1988. Evaluation of a miniature blood glucose sensor. Trans Am Soc Artif Intern Organs 34:255-258.

Leypoldt et al. 1984. Model of a two-substrate enzyme electrode for glucose. Anal. Chem. 56:2896-2904.

Linke et al. 1994. Amperometric biosensor for in vivo glucose sensing based on glucose oxidase immobilized in a redox hydrogel. Biosensors & Bioelectronics 9:151-158.

Lowe, 1984. Biosensors, Trends in Biotechnology, 2(3):59-65.

Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.

Lyandres et al. (2008). Progress toward an in vivo surface-enhanced raman spectroscopy glucose sensor. Diabetes Technology & Therapeutics, 10(4): 257-265.

Lynn, P. A. 1971. Recursive digital filters for biological signals. Med. & Biol. Engng. 9:37-43.

Makale et al. 2003. Tissue window chamber system for validation of implanted oxygen sensors. Am. J. Physiol. Heart Circ. Physiol. 284:H2288-2294.

Malin et al. 1999. Noninvasive Prediction of Glucose by Near-Infrared Diffuse Reflectance Spectroscopy. Clinical Chemistry 45:9, 1651-1658.

Mancy et al. 1962. A galvanic cell oxygen analyzer. Journal of Electroanalytical Chemistry 4:65-92.

Maran et al. 2002. Continuous subcutaneous glucose monitoring in diabetic patients: A multicenter analysis. Diabetes Care 25(2):347-352.

Marena et al. 1993. The artifical endocrine pancreas in clinical practice and research. Panminerva Medica 35(2):67-74.

Mascini et al. 1989. Glucose electrochemical probe with extended linearity for whole blood. J Pharm Biomed Anal 7(12): 1507-1512.

Mastrototaro, J. J. 2000. The MiniMed continuous glucose monitoring system. Diabetes Technol Ther 2(Suppl 1):S13-8.

Mastrototaro et al. 2003. Reproducibility of the continuous glucose monitoring system matches previous reports and the intended use of the product. Diabetes Care 26:256; author reply p. 257.

Matsuki. 1994. Energy transfer system utilizing amorphous wires for implantable medical devices. IEEE Transactions on Magnetics 31(2):1276-1282.

Matsumoto et al. 1998. A micro-planar amperometeric glucose sensor unsusceptible to interference species. Sensors and Actuators B 49:68-72.

Matthews et al. 1988. An amperometric needle-type glucose sensor testing in rats and man. Diabetic Medicine 5:248-252.

McCartney et al. 2001. Near-infrared fluorescence lifetime assay for serum glucose based on allophycocyanin-labeled concanavalin A. Anal Biochem 292:216-221.

McGrath et al. 1995. The use of differential measurements with a glucose biosensor for interference compensation during glucose determinations by flow injection analysis. Biosens Bioelectron 10:937-943.

Memoli et al. 2002. A comparison between different immobilised glucoseoxidase-based electrodes. J Pharm Biomed Anal 29:1045-1052.

Merriam-Webster Online Dictionary. Definition of "acceleration". http://www.merriam-webster.com/dictionary/Acceleration Jan. 11, 2010.

Merriam-Webster Online Dictionary. Definition of "system". http://www.merriam-webster.com/dictionary/System Jan. 11, 2010.

Merriam-Webster Online Dictionary. The term "nominal." http://www.m-w.com/dictionary/nominal.

Metzger et al. Jul. 2002. Reproducibility of glucose measurements using the glucose sensor. Diabetes Care 25(6):1185-1191.

Meyerhoff et al. 1992. On line continuous monitoring of subcutaneous tissue glucose in men by combining portable glucosensor with microdialysis. Diabetologia 35:1087-1092.

Miller et al. 1993. Development of an autotuned transcutaneous energy transfer system ASAIO Journal 39:M706-M710.

Moatti-Sirat et al., Reduction of acetaminophen interference in glucose sensors by a composite Nafion membrane: demonstration in rats and man, Diabetologia 37(6):610-616, Jun. 1994.

Morff et al. 1990. Microfabrication of reproducible, economical, electroenzymatic glucose sensors, Annual International Conference of the IEEE Engineering in Medicine and Biology Society, 12(2):0483-0484.

Mosbach et al. 1975. Determination of heat changes in the proximity of immobilized enzymes with an enzyme termistor and its use for the assay of metobolites, Biochim. Biophys. Acta. (Enzymology), 403:256-265.

Motonaka et al. 1993. Determination of cholesteral and cholesteral ester with novel enzyme microsensors, Anal. Chem. 65:3258-3261.

Moussy et al. 1994. A miniaturized Nafion-based glucose sensor: in vitro and in vivo evaluation in dogs. Int. J. Artif. Organs 17(2):88-94.

Muslu. 1991. Trickling filter performance. Apllied Biochemistry and Biotechnology 37:211-224.

Nafion® 117 Solution Product Description, Product No. 70160, Sigma-Aldrich Corp., St. Louis, MO.

Neuburger et al. 1987. Pulsed amperometric detection of carbohydrates at gold electrodes with a two-step potential waveform. Anal. Chem. 59:150-154.

Ohara et al. 1994. "Wired" enzyme electrodes for amperometric determination of glucose or lactate in the presence of interfering substances. Anal Chem 66:2451-2457.

Okuda et al. 1971. Mutarotase effect on micro determinations of D-glucose and its anomers with β-D-glucose oxidase. Anal Biochem 43:312-315.

Oxford English Dictionary Online. Definition of "impending". http://www.askoxford.com/results/?view=dev dict&field-12668446 Impending&branch= Jan. 11, 2010.

Palmisano et al. 2000. Simultaneous monitoring of glucose and lactate by an interference and cross-talk free dual electrode amperometric biosensor based on electropolymerized thin films. Biosensors & Bioelectronics 15:531-539.

Panteleon et al. 2003. The role of the independent variable to glucose sensor calibration. Diabetes Technology & Therapeutics 5(3):401-410.

Parker et al. 1999. A model-based algorithm for blood glucose control in type I diabetic patients. IEEE Trans. Biomed. Eng. 46(2):148-157.

Patel et al. 2003. Amperometric glucose sensors based on ferrocene containing polymeric electron transfer systems—a preliminary report. Biosens Bioelectron 18:1073-6.

Peacock et al. 2008. Cardiac troponin and outcome in acute heart failure. N. Engl. J. Med., 358: 2117-2126.

Pfeiffer, E.F. 1990. The glucose sensor: the missing link in diabetes therapy, Horm Metab Res Suppl. 24:154-164.

Pfeiffer et al. 1992. On line continuous monitoring of subcutaneous tissue glucose is feasible by combining portable glucosensor with microdialysis. Horm. Metab. Res. 25:121-124.

Phillps. 1995. A high capacity transcutaneous energy transmission system. ASAIO Journal 41:M259-M262.

Pichert et al. 2000. Issues for the coming age of continuous glucose monitoring Diabetes Educ 26(6):969-980.

Pickup et al. 1989. Potentially-implantable, amperometric glucose sensors with mediated electron transfer: improving the operating stability. Biosensors 4:109-119.

Pickup et al. 1993. Responses and Calibration of Amperometric Glucose Sensors Implanted in the Subcutaneous Tissue of Man. ACTA Diabetol, pp. 143-148.

Pickup et al. 1993. Developing glucose sensors for in vivo use. Elsevier Science Publishers Ltd (UK), TIBTECH vol. 11: 285-291.

Pinner et al., Cross-linking of cellulose acetate by ionizing radiation, Nature, vol. 184, 1303-1304, Oct. 24, 1959.

Pitzer et al. 2001. Detection of hypoglycemia with the GlucoWatch biographer. Diabetes Care 24(5):881-885.

Poirier et al. 1998. Clinical and statistical evaluation of self-monitoring blood glucose meters. Diabetes Care 21(11):1919-1924.

Poitout et al. 1994. Development of a glucose sensor for glucose monitoring in man: the disposable implant concept. Clinical Materials 15:241-246.

Postlethwaite et al. 1996. Interdigitated array electrode as an alternative to the rotated ring-disk electrode for determination of the reaction products of dioxygen reduction. Analytical Chemistry 68:2951-2958.

Quinn et al. 1995. Kinetics of glucose delivery to subcutaneous tissue in rats measured with 0.3-mm amperometric microsensors. The American Physiological Society E155-E161.

Quinn et al. 1997. Biocompatible, glucose-permeable hydrogel for in situ coating of implantable biosensors. Biomaterials 18:1665-1670.

Rabah et al., 1991. Electrochemical wear of graphite anodes during electrolysis of brine, Carbon, 29(2):165-171.

Reach et al. 1986. A Method for Evaluating in vivo the Functional Characteristics of Glucose Sensors. Biosensors 2:211-220.

Reach, G. 2001. Which threshold to detect hypoglycemia? Value of receiver-operator curve analysis to find a compromise between sensitivity and specificity. Diabetes Care 24(5):803-804.

Reach, Gerard. 2001. Letters to the Editor Re: Diabetes Technology & Therapeutics, 2000;2:49-56. Diabetes Technology & Therapeutics 3(1):129-130.

Rebrin et al. 1992. Subcutaenous glucose monitoring by means of electrochemical sensors: fiction or reality? J. Biomed. Eng. 14:33-40.

Rebrin et al. 1999. Subcutaneous glucose predicts plasma glucose independent of insulin: Implications for continuous monitoring. Am. J. Physiol. 277:E561-71.

Reusch. 2004. Chemical Reactivity. Organometallic Compounds. Virtual Textbook of Organic Chem. pp. 1-16, http://www.cem.msu.edu/—reusch/VirtualText/orgmetal.htm.

Rhodes et al. 1994. Prediction of pocket-portable and implantable glucose enzyme electrode performance from combined species permeability and digital simulation analysis. Analytical Chemistry 66(9):1520-1529.

Rivers et al., Central venous oxygen saturation monitoring in the critically ill patient, Current Opinion in Critical Care, 7:204-211, 2001.

Sakakida et al. 1992. Development of Ferrocene-Mediated Needle-Type Glucose Sensor as a Measure of True Subcutaneous Tissue Glucose Concentrations. Artif. Organs Today 2(2):145-158.

Salardi et al. 2002. The glucose area under the profiles obtained with continuous glucose monitoring system relationships with HbA1c in pediatric type 1 diabetic patients. Diabetes Care 25(10):1840-1844.

San Diego Plastics, Inc. 2009. Polyethylene Data Sheet, http://www.sdplastics.com/polyeth.html.

Sansen et al. 1990. A smart sensor for the voltammetric measurement of oxygen or glucose concentrations. Sensors and Actuators B 1:298-302.

Schmidt et al. 1992. Calibration of a wearable glucose sensor. The International Journal of Artificial Organs 15(1):55-61.

Schmidt et al. 1993. Glucose concentration in subcutaneous extracellular space. Diabetes Care 16(5):695-700.

Schmidtke et al. 1998. Accuracy of the one-point in vivo calibration of "wired" glucose oxidase electrodes implanted in jugular veins of rats in periods of rapid rise and decline of the glucose concentration. Anal Chem 70:2149-2155.

Schmidtke et al., Measurement and modeling of the transient difference between blood and subcutaneous glucose concentrations in the rat after injection of insulin. Proc Natl Acad Sci U S A 1998, 95, 294-299.

Schoemaker et al. 2003. The SCGM1 system: Subcutaneous continuous glucose monitoring based on microdialysis technique. Diabetes Technology & Therapeutics 5(4):599-608.

Schoonen et al. 1990 Development of a potentially wearable glucose sensor for patients with diabetes mellitus: design and in-vitro evaluation. Biosensors & Bioelectronics 5:37-46.

Service et al. 1987. Measurements of glucose control. Diabetes Care, 10: 225-237.

Service, R. F. 2002. Can sensors make a home in the body? Science 297:962-3.

Sharkawy et al. 1996. Engineering the tissue which encapsulates subcutaneous implants. I. Diffusion properties, J Biomed Mater Res, 37:401-412.

Shichiri et al. 1983. Glycaemic Control in Pancreatectomized Dogs with a Wearable Artificial Endocrine Pancreas. Diabetologia 24:179-184.

Skyler, J. S. 2000. The economic burden of diabetes and the benefits of improved glycemic control: The potential role of a continuous glucose monitoring system. Diabetes Technology & Therapeutics 2 Suppl 1:S7-12.

Slater-Maclean et al. 2008. Accuracy of glycemic measurements in the critically ill. Diab. Thechnol. & Therapeut., 10:169-177.

Smith et al. 1998. An externally powered, multichannel, implantable stimulator-telemeter for control of paralyzed muscle. IEEE Transactions on Biomedical Engineering 45(4):463-475.

Sokolov et al. 1995. Metrological opportunities of the dynamic mode of operating an enzyme amperometric biosensor. Med. Eng. Phys. 17(6):471-476.

Sparacino et al., 2008. Continuous glucose monitoring time series and hypo/hyperglycemia prevention: requirements, methods, open problems, Current Diabetes Reviews, 4:181-192.

Sproule et al. 2002. Fuzzy pharmacology: Theory and applications. Trends in Pharmacological Sciences, 23(9):412-417.

Sriyudthsak et al. 1996. Enzyme-epoxy membrane based glucose analyzing system and medical applications. Biosens Bioelectron 11:735-742.

Steil et al. 2003. Determination of plasma glucose during rapid glucose excursions with a subcutaneous glucose sensor. Diabetes Technology & Therapeutics 5(1):27-31.

Stern et al., 1957. Electrochemical polarization: 1. A theoretical analysis of the shape of polarization curves, Journal of the Electrochemical Society, 104(1):56-63.

Street et al. 1988. A note on computing robust regression estimates via iteratively reweighted least squares. The American Statistician 42(2):152-154.

Sumino T. et al. 1998. Preliminary study of continuous glucose monitoring with a microdialysis technique. Proceedings of the IEEE, 20(4):1775-1778.

Takegami et al. 1992. Pervaporation of ethanol water mixtures using novel hydrophobic membranes containing polydimethylsiloxane, Journal of Membrance Science, 75(93-105).

Tamura, T. et al. 2000. Preliminary study of continuous glucose monitoring with a microdialysis technique and a null method—a numerical analysis. Frontiers Med. Biol. Engng. 10(2):147-156.

Tanenberg et al. 2000. Continuous glucose monitoring system: a new approach to the diagnosis of diabetic gastroparesis. Diabetes Technology & Therapeutics, 2 Suppl 1:S73-80.

Tatsuma et al. 1991. Oxidase/peroxidase bilayer-modified electrodes as sensors for lactate, pyruvate, cholesteral and uric acid, Analytica Chimica Acta, 242:85-89.

Thomé et al. 1995.—Abstract—Can the decrease in subcutaneous glucose concentration precede the decrease in blood glucose level? Proposition for a push-pull kinetics hypothesis, Horm. Metab. Res. 27:53.

Thomé-Duret et al. 1996. Modification of the sensitivity of glucose sensor implanted into subcutaneous tissue. Diabetes Metabolism, 22:174-178.

Thome-Duret et al. 1996. Use of a subcutaneous glucose sensor to detect decreases in glucose concentration prior to observation in blood, Anal. Chem. 68:3822-3826.

Thome-Duret et al. 1998. Continuous glucose monitoring in the free-moving rat. Metabolism, 47:799-803.

Tierney et al. 2000. The GlucoWatch® biographer: A frequent, automatic and noninvasive glucose monitor. Ann. Med. 32:632-641.

Torjman et al., Glucose monitoring in acute care: technologies on the horizon, Journal of Deabetes Science and Technology, 2(2):178-181, Mar. 2008.

Trecroci, D. 2002. A Glimpse into the Future—Continuous Monitoring of Glucose with a Microfiber. Diabetes Interview 42-43.

Tse and Gough. 1987. Time-Dependent Inactivation of Immobilized Glucose Oxidase and Catalase. Biotechnol. Bioeng. 29:705-713.

Turner et al. 1987. Carbon Monoxide: Acceptor Oxidoreductase from Pseudomonas Thermocarboxydovorans Strain C2 and its use in a Carbon Monoxide Sensor. Analytica Chimica Acta, 163: 161-174.

Unger et al. 2004. Glucose control in the hospitalized patient. Emerg Med 36(9):12-18.

Updike et al. 1967. The enzyme electrode. Nature, 214:986-988.

Updike et al. 1988. Laboratory Evaluation of New Reusable Blood Glucose Sensor. Diabetes Care, 11:801-807.

Updike et al. 1994. Enzymatic glucose sensor: Improved long-term performance in vitro and in vivo. Asaio Journal, 40(2):157-163.

Updike et al. 2000. A subcutaneous glucose sensor with improved longevity, dynamic range, and stability of calibration. Diabetes Care 23(2):208-214.

Utah Medical Products Inc., Blood Pressure Tranducers product specifications. 6 pp. 2003-2006, 2003.

Vadgama, P. Nov. 1981. Enzyme electrodes as practical biosensors. Journal of Medical Engineering & Technology 5(6):293-298.

Vadgama. 1988. Diffusion limited enzyme electrodes. Nato ASI Series: Series C, Math and Phys. Sci. 226:359-377.

Valdes et al. 2000. In vitro and in vivo degradation of glucose oxidase enzyme used for an implantable glucose biosensor. Diabetes Technol. Ther. 2:367-376.

Van den Berghe 2004. Tight blood glucose control with insulin in "real-life" intensive care. Mayo Clin Proc 79(8):977-978.

Velho et al. 1989. In vitro and in vivo stability of electrode potentials in needle-type glucose sensors. Influence of needle material. Diabetes 38:164-171.

Wang et al. 1994. Highly Selective Membrane-Free, Mediator-Free Glucose Biosensor. Anal. Chem. 66:3600-3603.

Wang et al. 1997. Improved ruggedness for membrane-based amperometric sensors using a pulsed amperometric method. Anal Chem 69:4482-4489.

Ward et al. 2000. Understanding Spontaneous Output Fluctuations of an Amperometric Glucose Sensor: Effect of Inhalation Anesthesia and e of a Nonenzyme Containing Electrode. ASAIO Journal 540-546.

Ward et al. 2002. A new amperometric glucose microsensor: In vitro and short-term in vivo evaluation. Biosensors & Bioelectronics, 17:181-189.

Wikipedia 2006. "Intravenous therapy," http://en.wikipedia.org/wiki/Intravenous_therapy, Aug. 15, 2006, 6 pp.

Wiley Electrical and Electronics Engineering Dictionary. 2004. John Wiley & Sons, Inc. pp. 141, 142, 548, 549.

Wilkins et al. 1988. The coated wire electrode glucose sensor, Horm Metab Res Suppl., 20:50-55.

Wilson et al. 2000. Enzyme-based biosensors for in vivo measurements. Chem. Rev., 100:2693-2704.

Wood, W. et al. Mar. 1990. Hermetic Sealing with Epoxy. Mechanical Engineering 1-3.

Woodward. 1982. How Fibroblasts and Giant Cells Encapsulate Implants: Considerations in Design of Glucose Sensor. Diabetes Care 5:278-281.

Worsley et al., Measurement of glucose in blood with a phenylboronic acid optical sensor, Journal of Diabetes Science and Technology, 2(2):213-220, Mar. 2008.

Wright et al., Bioelectrochemical dehalogenations via direct electrochemistry of poly(ethylene oxide)—modified myoglobin, Electrochemistry Communications 1 (1999) 603-611.

Wu et al. 1999. In situ electrochemical oxygen generation with an immunoisolation device. Annals New York Academy of Sciences, pp. 105-125.

Yamasaki, Yoshimitsu. Sep. 1984. The development of a needle-type glucose sensor for wearable artificial endocrine pancreas. Medical Journal of Osaka University 35(1-2):25-34.

Yamasaki et al. 1989. Direct measurement of whole blood glucose by a needle-type sensor. Clinica Chimica Acta. 93:93-98.

Yang et al. 1998. Development of needle-type glucose sensor with high selectivity. Science and Actuators B 46:249-256.

Yang, et al. 2004. A Comparison of Physical Properties and Fuel Cell Performance of Nafion and Zirconium Phosphate/Nafion Composite Membranes. Journal of Membrane Science 237:145-161.

Ye et al. 1993. High Current Density 'Wired' Quinoprotein Glucose Dehydrogenase Electrode. Anal. Chem. 65:238-241.

Zamzow et al. 1990. Development and evaluation of a wearable blood glucose monitor, ASAIO Transactions; 36(3): pp. M588-M591.

Zavalkoff et al. 2002. Evaluation of conventional blood glucose monitoring as an indicator of integrated glucose values using a continuous subcutaneous sensor. Diabetes Care 25(9):1603-1606.

Zethelius et al. 2008. Use of multiple biomarkers to improve the prediction of death from cardiovascular causes. N. Engl. J. Med., 358: 2107-2116.

Zhang et al (1993). Electrochemical oxidation of H2O2 on Pt and Pt+Ir electrodes in physiological buffer and its applicability to H2O2-based biosensors. J. Electroanal. Chem., 345:253-271.

Zhang et al. 1993. In vitro and in vivo evaluation of oxygen effects on a glucose oxidase based implantable glucose sensor. Analytica Chimica Acta, 281:513-520.

Zhang et al. 1994. Elimination of the acetaminophen interference in an implantable glucose sensor. Analytical Chemistry 66(7):1183-1188.

Zhu et al. (1994). "Fabrication and characterization of glucose sensors based on a microarray H2O2 electrode." Biosensors & Bioelectronics, 9: 295-300.

Ziaie et al. 1997. A single-channel implantable microstimulator for functional neuromuscular stimulation. IEEE Transactions on Biomedical Engineering 44(10):909-920.

Office Action dated Jul. 30, 2009 in U.S. Appl. No. 12/102,654.
Office Action dated Mar. 10, 2010 in U.S. Appl. No. 12/102,654.
Office Action dated Nov. 9, 2009 in U.S. Appl. No. 11/038,340.
Office Action dated May 17, 2007 in U.S. Appl. No. 11/077,759.
Office Action dated Dec. 29, 2009 in U.S. Appl. No. 11/077,739.
Office Action dated Mar. 1, 2010 in U.S. Appl. No. 11/077,739.

Office Action dated Feb. 3, 2010 in U.S. Appl. No. 11/077,765.
Office Action dated Jan. 5, 2010 in U.S. Appl. No. 11/078,232.
Office Action dated Dec. 31, 2009 in U.S. Appl. No. 11/077,714.
Office Action dated Jan. 27, 2010 in U.S. Appl. No. 11/077,714.
Office Action dated Sep. 2, 2009 in U.S. Appl. No. 11/078,072.
Office Action dated Feb. 18, 2010 in U.S. Appl. No. 11/078,072.
Office Action dated Jan. 21, 2010 in U.S. Appl. No. 11/157,365.
Office Action dated Aug. 25, 2009 in U.S. Appl. No. 11/334,876.
Office Action dated Oct. 29, 2009 in U.S. Appl. No. 11/360,819.
Office Action dated Apr. 7, 2010 in U.S. Appl. No. 11/360,819.
Office Action dated Feb. 23, 2010 in U.S. Appl. No. 12/113,508.
Armour et al. Dec. 1990. Application of Chronic Intravascular Blood Glucose Sensor in Dogs. Diabetes 39:1519-1526.
Aussedat et al. 1997. A user-friendly method for calibrating a subcutaneous glucose sensor-based hypoglycaemic alarm. Biosensors & Bioelectronics 12(11):1061-1071.
Bellucci et al. Jan. 1986. Electrochemical behaviour of graphite-epoxy composite materials (GECM) in aqueous salt solutions, Journal of Applied Electrochemistry, 16(1):15-22.
Biermann et al. 2008. How would patients behave if they were continually informed of their blood glucose levels? A simulation study using a "virtual" patient. Diab. Thechnol. & Therapeut., 10:178-187.
Bindra et al. 1991. Design and in Vitro Studies of a Needle-Type Glucose Senso for Subcutaneous Monitoring. Anal. Chem 63:1692-96.
Bland et al. 1986. Statistical methods for assessing agreement between two methods of clinical measurement. Lancet 1:307-310.
Bobbioni-Harsch et al. 1993. Lifespan of subcutaneous glucose sensors and their performances during dynamic glycaemia changes in rats, J. Biomed. Eng. 15:457-463.
Brooks et al. "Development of an on-line glucose sensor for fermentation monitoring," Biosensors, 3:45-56 (1987/88).
Candas et al (1994). "An adaptive plasma glucose controller basedon a nonlinear insulin/glucose model." IEEE Transactions on Biomedical Engineering, 41(2): 116-124.
Choleau et al. 2002. Calibration of a subcutaneous amperometric glucose sensor implanted for 7 days in diabetic patients. Part 2. Superiority of the one-point calibration method. Biosensors and Bioelectronics 17:647-654.
Csöregi et al. 1994. Amperometric microbiosensors for detection of hydrogen peroxide and glucose based on peroxidase-modified carbon fibers. Electroanalysis 6:925-933.
Davies, et al. 1992. Polymer membranes in clinical sensor applications. I. An overview of membrane function, Biomaterials, 13(14):971-978.
El-Khatib et al. 2007. Adaptive closed-loop control provides blood-glucose regulation using dual subcutaneous insulin and glucagon infusion in diabetic swine, Journal of Diabetes Science and Technology, 1(2):181-192.
Fabietti et al. 2007. Clinical validation of a new control-oriented model of insulin and glucose dynamcs in subjects with type 1 diabetes, Diabetes Technology & Therapeutics, 9(4):327-338.
Frost et al. 2002. Implantable chemical sensors for real-time clinical monitoring: Progress and challenges. Current Opinion in Chemical Biology 6:633-641.
Guerci et al., Clinical performance of CGMS in type 1 diabetic patents treated by continuous subcutaneous insulin infusion using insulin analogs, Diabetes Care, 26:582-589, 2003.
Heller, A. 1992. Electrical Connection of Enzyme Redox Centers to Electrodes. J. Phys. Chem. 96:3579-3587.
Hicks, 1985. In Situ Monitoring, Clinical Chemistry, 31(12):1931-1935.
Hu, et al. 1993. A needle-type enzyme-based lactate sensor for in vivo monitoring, Analytica Chimica Acta, 281:503-511.
Johnson et al. 1992. In vivo evaluation of an electroenzymatic glucose sensor implanted in subcutaneous tissue. Biosensors & Bioelectronics, 7:709-714.
Kamath et al. Calibration of a continuous glucose monitor: effect of glucose rate of change, Eighth Annual Diabetes Technology Meeting, Nov. 13-15, 2008, p. A88.
Kawagoe et al. 1991. Enzyme-modified organic conducting salt microelectrode, Anal. Chem. 63:2961-2965.

Kerner et al. "The function of a hydrogen peroxide-detecting electroenzymatic glucose electrode is markedly impaired in human sub-cutaneous tissue and plasma," Biosensors & Bioelectronics, 8:473-482 (1993).
Kurnik et al. 1999. Application of the mixtures of experts algorithm for signal processing in a noninvasive glucose monitoring system. Sensors and Actuators B, 60:19-26.
Lohn et al., A knowledge-based system for real-time validation of calibrations and measurements, Chemometrics and Intelligent Laboratory Systems, 1999 46, 57-66.
Maidan et al. 1992. Elimination of Electrooxidizable Interferent-Produced Currents in Amperometric Biosensors, Analytical Chemistry, 64:2889-2896.
Mastrototaro et al. "An electroenzymatic glucose sensor fabricated on a flexible substrate," Sensors and Actuators B, 5:139-44 (1991).
Mazze et al. 2008. Characterizing glucose exposure for individuals with normal glucose tolerance using continuous glucose monitoring and ambulatory glucose profile analysis. Diab. Thechnol. & Therapeut., 10:149-159.
McKean, et al. Jul. 7, 1988. A Telemetry Instrumentation System for Chronically Implanted Glucose and Oxygen Sensors. Transactions on Biomedical Engineering 35:526-532.
Moatti-Sirat et al. 1992. Evaluating in vitro and in vivo the interference of ascorbate and acetaminophen on glucose detection by a needle-type glucose sensor, Biosensors & Bioelectronics 7:345-352.
Murphy, et al. 1992. Polymer membranes in clinical sensor applications. II. The design and fabrication of permselective hydrogels for electrochemical devices, Biomaterials, 13(14):979-990.
Ohara, et al. Dec. 1993. Glucose electrodes based on cross-linked bis(2,2'-bipyridine)chloroosmium(+/2+) complexed poly(1-vinylimidazole) films, Analytical Chemistry, 65:3512-3517.
Pickup et al. "Implantable glucose sensors: choosing the appropriate sensor strategy," Biosensors, 3:335-346 (1987/88).
Pishko et al. "Amperometric glucose microelectrodes prepared through immobilization of glucose oxidase in redox hydrogels," Anal. Chem., 63:2268-72 (1991).
Poitout et al. 1993. A glucose monitoring system for on line estimation in man of blood glucose concentration using a miniaturized glucose sensor implanted in the subcutaneous tissue and a wearable control unit. Diabetologia 36:658-663.
Poitout, et al. 1991. In Vitro and in Vivo Evaluation in Dogs of a Miniaturized Glucose Sensor, ASAIO Transactions, 37:M298-M300.
Prabhu et al. 1981. Electrochemical studies of hydrogen peroxide at a platinum disc electrode, Electrochimica Acta 26(6):725-729.
Reach et al. 1992. Can continuous glucose monitoring be used for the treatment of diabetes? Analytical Chemistry 64(5):381-386.
Rigla et al. 2008. Real-time continuous glucose monitoring together with telemedical assitance improves glycemic control and glucose stability in pump-treated patients. Diab. Thechnol. & Therapeut., 10:194-199.
Rinken et al. 1998. Calibration of glucose biosensors by using pre-steady state kinetic data. Biosensors & Bioelectronics, 13:801-807.
Sakakida et al. 1993. Ferrocene-Mediated Needle Type Glucose Sensor Covered with Newly Designed Biocompatible Membran, Sensors and Actuators B 13-14:319-322.
Service et al. 1970. Mean amplitude of glycemic excursions, a measure of diabetic instability. Diabetes, 19: 644-655.
Shaw et al. "In vitro testing of a simply constructed, highly stable glucose sensor suitable for implantation in diabetic patients," Biosensors & Bioelectronics, 6:401-406 (1991).
Shichiri et al., 1989. Membrane Design for Extending the Long-Life of an Implantable Glucose Sensor. Diab. Nutr. Metab. 2:309-313.
Shults et al. 1994. A telemetry-instrumentation system for monitoring multiple subcutaneously implanted glucose sensors. IEEE Transactions on Biomedical Engineering 41(10):937-942.
Sokol et al. 1980, Immobilized-enzyme rate-determination method for glucose analysis, Clin. Chem. 26(1):89-92.
Sternberg et al. 1988. Study and Development of Multilayer Needle-type Enzyme-based Glucose Microsensors. Biosensors 4:27-40.
Thompson et al., In Vivo Probes: Problems and Perspectives, Department of Chemistry, University of Toronto, Canada, pp. 255-261, 1986.

Turner and Pickup, "Diabetes mellitus: biosensors for research and management," Biosensors, 1:85-115 (1985).
Updike et al. 1979. Continuous glucose monitor based on an immobilized enzyme electrode detector. J Lab Clin Med, 93(4):518-527.
Updike et al. 1982. Implanting the glucose enzyme electrode: Problems, progress, and alternative solutions. Diabetes Care, 5(3):207-212.
Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons, pp. 117-137.
Velho et al. 1989. Strategies for calibrating a subcutaneous glucose sensor. Biomed Biochim Acta 48(11/12):957-964.
von Woedtke et al. 1989. In situ calibration of implanted electrochemical glucose sensors. Biomed Biochim. Acta 48(11/12):943-952.
Ward et al. 1999. Assessment of chronically implanted subcutaneous glucose sensors in dogs: The effect of surrounding fluid masses. ASAIO Journal, 45:555-561.
Ward et al. 2000. Rise in background current over time in a subcutaneous glucose sensor in the rabbit: Relevance to calibration and accuracy. Biosensors & Bioelectronics, 15:53-61.
Yang et al (1996). "A glucose biosensor based on an oxygen electrode: In-vitro performances in a model buffer solution and in blood plasma," Biomedical Instrumentation & Technology, 30:55-61.
Zhu et al. 2002. Planar amperometric glucose sensor based on glucose oxidase immobilized by chitosan film on prussian blue layer. Sensors, 2:127-136.
European Search Report for App. No. 98908875.2 dated Apr. 29, 2004.
IPRP for PCT/US04/38724 filed Nov. 17, 2004.
ISR and WO for PCT/US04/38724 filed Nov. 17, 2004.
Official Communication in EP App. No. 05723951.9, dated Nov. 21, 2007.
Office Action dated Sep. 30, 2002 in U.S. App. No. 09/636,369.
Office Action dated Oct. 20, 2004 in U.S. Appl. No. 10/632,537.
Office Action dated Dec. 21, 2004 in U.S. Appl. No. 10/632,537.
Office Action dated Jan. 11, 2005 in U.S. Appl. No. 10/896,772.
Office Action dated Jul. 19, 2005 in U.S. Appl. No. 10/896,772.
Office Action dated Dec. 14, 2005 in U.S. Appl. No. 10/896,772.
Office Action dated Jan. 27, 2006 in U.S. Appl. No. 11/007,635.
Office Action dated May 22, 2006 in U.S. Appl. No. 10/896,772.
Office Action dated Oct. 4, 2006 in U.S. Appl. No. 11/334,876.
Office Action dated Oct. 5, 2006 in U.S. Appl. No. 10/633,329.
Office Action dated Oct. 11, 2006 in U.S. Appl. No. 11/077,714.
Office Action dated Nov. 27, 2006 in U.S. Appl. No. 10/789,359.
Office Action dated Feb. 12, 2007 in U.S. Appl. No. 10/633,404.
Office Action dated Mar. 26, 2007 in U.S. Appl. No. 10/633,329.
Office Action dated Apr. 10, 2007 in U.S. Appl. 11/077,714.
Office Action dated Jun. 1, 2007 in U.S. Appl. No. 11/077,740.
Office Action dated Jul. 27, 2007 in U.S. Appl. No. 11/077,714.
Office Action dated Jul. 30, 2007 in U.S. Appl. No. 10/633,329.
Office Action dated Sep. 25, 2007 in U.S. Appl. No. 11/334,876.
Office Action dated Nov. 1, 2007 in U.S. Appl. No. 11/077,740.
Office Action dated Nov. 28, 2007 in U.S. Appl. No. 10/991,966.
Office Action dated Dec. 31, 2007 in U.S. Appl. No. 11/077,765.
Office Action dated Jan. 10, 2008 in U.S. Appl. No. 11/077,714.
Office Action dated Jan. 15, 2008 in U.S. Appl. No. 11/034,344.
Office Action dated Feb. 4, 2008 in U.S. Appl. No. 10/633,329.
Office Action dated Feb. 7, 2008 in U.S. Appl. No. 11/077,740.
Office Action dated Mar. 20, 2008 in U.S. Appl. No. 10/789,359.
Office Action dated Mar. 31, 2008 in U.S. Appl. No. 11/077,759.
Office Action dated May 2, 2008 in U.S. Appl. No. 11/334,876.
Office Action dated May 5, 2008 in U.S. Appl. No. 11/078,232.
Office Action dated May 16, 2008 in U.S. Appl. No. 11/077,765.
Office Action dated May 29, 2008 in U.S. Appl. No. 95/001,039.
Office Action mailed Jun. 5, 2008 in U.S. Appl. No. 10/838,909.
Office Action dated Jun. 12, 2008 in U.S. Appl. No. 10/633,329.
Office Action dated Jun. 17, 2008 in U.S. Appl. No. 11/038,340.
Office Action dated Jun. 17, 2008 in U.S. Appl. No. 95/001,038.
Office Action dated Jun. 24, 2008 n U.S. Appl. No. 11/007,920.
Office Action dated Jun. 26, 2008 in U.S. Appl. No. 11/157,365.
Office Action dated Jun. 30, 2008 in U.S. Appl. No. 11/360,252.
Office Action dated Jul. 10, 2008 in U.S. Appl. No. 11/077,759.
Office Action dated Jul. 15, 2008 in U.S. Appl. No. 10/633,367.
Office Action dated Jul. 22, 2008 in U.S. Appl. No. 10/991,966.
Office Action dated Jul. 25, 2008 in U.S. Appl. No. 11/077,740.
Office Action dated Aug. 11, 2008 in U.S. Appl. No. 11/360,819.
Office Action dated Aug. 26, 2008 in U.S. Appl. No. 11/334,876.
Office Action dated Sep. 16, 2008 in U.S. Appl. No. 11/077,714.
Office Action dated Sep. 19, 2008 in U.S. Appl. No. 11/077,765.
Office Action dated Oct. 3, 2008 in U.S. Appl. No. 10/789,359.
Office Action dated Nov. 12, 2008 in U.S. Appl. No. 11/078,232.
Office Action dated Nov. 28, 2008 in U.S. Appl. No. 11/333,837.
Office Action dated Dec. 18, 2008 in U.S. Appl. No. 10/633,329.
Office Action dated Dec. 23, 2008 in U.S. Appl. No. 12/102,745.
Office Action dated Dec. 26, 2008 in U.S. Appl. No. 11/360,819.
Office Action dated Jan. 5, 2009 in U.S. Appl. No. 11/038,340.
Office Action dated Jan. 7, 2009 in U.S. Appl. No. 11/157,365.
Office Action dated Jan. 23, 2009 in U.S. Appl. No. 11/077,765.
Office Action dated Jan. 29, 2009, in U.S. Appl. No. 11/360,252.
Office Action dated Mar. 5, 2009 in U.S. Appl. No. 11/078,232.
Office Action mailed Mar. 16, 2009 in U.S. Appl. No. 10/838,909.
Office Action dated Apr. 16, 2009 in U.S. Appl. No. 11/077,714.
Office Action dated Apr. 28, 2009 in U.S. Appl. No. 11/077,740.
Office Action dated May 19, 2009 in U.S. Appl. No. 11/038,340.
Office Action dated May 26, 2009 in U.S. Appl. No. 11/077,759.
Office Action dated Jun. 11, 2009 in U.S. Appl. No. 10/633,329.
Office Action dated Jun. 11, 2009 in U.S. Appl. No. 10/633,367.
Office Action dated Jun. 23, 2009 in U.S. Appl. No. 10/648,849.
Office Action dated Jun. 29, 2009 in U.S. Appl. No. 11/333,837.
Office Action dated Jul. 7, 2009 in U.S. Appl. No. 12/102,729.
Office Action dated Jul. 21, 2009 in U.S. Appl. No. 11/077,739.
Office Action dated Jul. 21, 2009 in U.S. Appl. No. 11/078,232.
Office Action dated Jul. 21, 2009 in U.S. Appl. No. 11/157,365.
Office Action dated Jul. 23, 2009, in U.S. Appl. No. 11/360,252.
Adilman, Glenn, Videogames: Knowing the Score, Creative Computing, V9, p. 224(5), Dec. 1983, Dialog: File 148, Acc#01891055.
Diabetes Educational Video Game Recognized by Software Publishers Association, Press Release, Novo Nordisk, Mar. 14, 1994.
Freiberger, Paul, Video Game Takes on Diabetes Superhero 'Captain Novolin' Offers Treatment Tips, San Francisco Examiner, Jun. 26, 1992, Fourth Edition, Business Sec. B1.
Jaffari et al., Recent advances in amperometric glucose biosensors for in vivo monitoring, Physiol. Meas. 16 (1995) 1-15.
Mazzola et al., Video Diabetes: A Teaching Tool for Children with Insulin-Dependent Diabetes, Proceedings—7th Annual Symposium on Computer Applications in Medical Care; Washington, D.C.; Dialog:, (Oct. 1983), File 8, Acc#01624462.
Nintendo Healthcare, Wired, Dec. 1993.
Raya Systems Pioneers Healthy Video Games, PlayRight, Nov. 1993 (pp. 14-15).
Office Action dated Feb. 2, 2010 in U.S. Appl. No. 11/038,340.
Office Action dated Jun. 7, 2010 in U.S. Appl. No. 11/038,340.
Office Action dated Jul. 7, 2010 in U.S. Appl. No. 12/098,359.
Office Action dated May 28, 2010 in U.S. Appl. No. 95/001,038.
Office Action dated Apr. 27, 2010 in U.S. Appl. No. 10/633,329.
Office Action dated Jun. 28, 2010 in U.S. Appl. No. 12/182,073.
Office Action dated Jun. 25, 2010 in U.S. Appl. No. 12/536,852.
Office Action dated Jun. 3, 2010 in U.S. Appl. No. 12/264,160.
Office Action dated Apr. 27, 2010 in U.S. Appl. No. 11/078,232.
Office Action dated Jun. 10, 2010 in U.S. Appl. No. 11/078,072.
Office Action dated Apr. 12, 2010 in U.S. Appl. No. 11/333,837.
Office Action dated Jul. 2, 2010 in U.S. Appl. No. 11/333,837.
Office Action dated Jun. 24, 2010 in U.S. Appl. No. 12/113,724.
Abel et al. Biosensors for in vivo glucose measurement: can we cross the experimental stage. Biosens Bioelectron 2002, 17, 1059-1070.
Baker et al. 1996. Dynamic delay and maximal dynamic error in continuous biosensors. Anal Chem, 68:1292-1297.
Bani Amer, M. M. 2002. An accurate amperometric glucose sensor based glucometer with eliminated cross-sensitivity. J Med Eng Technol, 26(5):208-213.
Bard et al. 1980. Electrochemical Methods. John Wiley & Sons, pp. 173-175.

Bland et al, 1990. A note on the use of the intraclass correlation coefficient in the evaluation of agreement between two methods of measurement. *Comput. Biol. Med.*, 20(5):337-340.

Bode et al. 1999. Continuous glucose monitoring used to adjust diabetes therapy improves glycosylated hemoglobin: a pilot study. *Diabetes Research and Clinical Practice*, 46:183-190.

Bode et al. 2000. Using the continuous glucose monitoring system to improve the management of type 1 diabetes. *Diabetes Technology & Therapeutics*, 2 Suppl 1, S43-48.

Bode, B. W. 2000. Clinical utility of the continuous glucose monitoring system. *Diabetes Technol Ther*, 2 Suppl 1, S35-41.

Bolinder et al. 1992. Microdialysis measurement of the absolute glucose concentration in subcutaneous adipose tissue allowing glucose monitoring in diabetic patients. *Diabetologia*, 35.1177-1180.

Bremer et al. 1999. Is blood glucose predictable from previous values? A solicitation for data. *Diabetes*, 48:445-451.

Cass et al. "Ferrocene-mediated enzyme electrodes for amperometric determination of glucose," Anal. Chem., 36:667-71 (1984).

Chia et al. Glucose sensors: toward closed loop insulin delivery. Endocrinol Metab Clin North Am 2004, 33, 175-95, xi.

Choleau et al. 2002. Calibration of a subcutaneous amperometric glucose sensor implanted for 7 days in diabetic patients. Part 2. Superiority of the one-point calibration method. *Biosensors and Bioelectronics*, 17:647-654.

Garg, S.; Schwartz, S.; Edelman, S. Improved Glucose Excursions Using an Implantable Real-Time Continuous Glucose Sensor in Adults with Type I Diabetes. Diabetes Care 2004, 27, 734-738.

Gilligan et al. Feasibility of continuous long-term glucose monitoring from a subcutaneous glucose sensor in humans. Diabetes Technol Ther 2004, 6, 378-386.

Heller, A. "Electrical wiring of redox enzymes," Acc. Chem. Res., 23:128-134 (1990).

Heller, A. Implanted electrochemical glucose sensors for the management of diabetes. Annu Rev Biomed Eng 1999, 1, 153-175.

Hunter et al. Minimally Invasive Glucose Sensor and Insulin Delivery System. MIT Home Automation and Healthcare Consortium 2000.

Kerner, W. 2001. Implantable glucose sensors: Present status and future developments. *Exp. Clin. Endocrinol. Diabetes*, 109 Suppl 2, S341-346.

Koschinsky et al. 1998. New approach to technical and clinical evaluation of devices for self-monitoring of blood glucose. Diabetes Care 11(8): 619-619.

Lerner et al. 1984. An implantable electrochemical glucose sensor. *Ann. N. Y. Acad. Sci.*, 428:263-278.

Lynch et al. 2001. Estimation-based model predictive control of blood glucose in type I diabetics: A simulation study. *Proceedings of the IEEE 27th Annual Northeast Bioengineering Conference*, pp. 79-80.

March, W. F. Dealing with the delay. Diabetes Technol Ther 2002, 4, 49-50.

Martin, R. F. 2000. General Deming regression for estimating systematic bias and its confidence interval in method-comparison studies. *Clinical Chemistry*, 46(1):100-104.

Monsod et al. 2002. Do sensor glucose levels accurately predict plasma glucose concentrations during hypoglycemia and hyperinsulinemia? *Diabetes Care*, 25(5):889-893.

Pickup et al. "In vivo molecular sensing in diabetes mellitus: an implantable glucose sensor with direct electron transfer," Diabetologia, 32:213-217 (1989).

Rebrin et al. "Automated feedback control of subcutaneous glucose concentration in diabetic dogs," Diabetologia, 32:573-76 (1989).

Sansen et al. 1985. "Glucose sensor with telemetry system." In Ko, W. H. (Ed.). Implantable Sensors for Closed Loop Prosthetic Systems. Chap. 12, pp. 167-175, Mount Kisco, NY: Futura Publishing Co.

Selam, J. L. Management of diabetes with glucose sensors and implantable insulin pumps. From the dream of the 60s to the realities of the 90s. ASAIO J 1997, 43, 137-142.

Shichiri et al. 1986. Telemetry glucose monitoring device with needle-type glucose sensor: A useful tool for blood glucose monitoring in diabetic individuals. *Diabetes Care*, 9(3):298-301.

Shichiri et al. Wearable artificial endocrine pancreas with needle-type glucose sensor. Lancet 1982, 2, 1129-1131.

Shichiri et al. Needle-type Glucose Sensor for Wearable Artificial Endocrine Pancreas. Book Implantable Sensors 1985, 197-210.

Sternberg et al. 1996. Does fall in tissue glucose precede fall in blood glucose? *Diabetologia*, 39:609-612.

Tierney et al. 2000. Effect of acetaminophen on the accuracy of glucose measurements obtained with the GlucoWatch biographer. Diabetes Technol Ther 2:199-207.

Tilbury et al. 2000. Receiver operating characteristic analysis for intelligent medical systems—A new approach for finding confidence intervals. *IEEE Transactions on Biomedical Engineering*, 47(7):952-963.

Trajanoski et al. 1998. Neural predictive controller for insulin delivery using the subcutaneous route. *IEEE Transactions on Biomedical Engineering*, 45(9):1122-1134.

Wagner et al. 1998. Continuous amperometric monitoring of glucose in a brittle diabetic chimpanzee with a miniature subcutaneous electrode. Proc. Natl. Acad. Sci. A, 95:6379-6382.

Wientjes, K. J. C. Development of a glucose sensor for diabetic patients. 2000.

Wilkins et al. 1995. Integrated implantable device for long-term glucose monitoring. Biosens. Bioelectron., 10:485-494.

Wilkins et al. Glucose monitoring: state of the art and future possibilities. Med Eng Phys 1995, 18, 273-288.

Wilson et al. 1992. Progress toward the development of an implantable sensor for glucose. Clin. Chem., 38(9):1613-1617.

US 7,530,950, 05/2009, Brister et al. (withdrawn)

\* cited by examiner

2

INTEGRATED RECEIVER FOR CONTINUOUS ANALYTE SENSOR

RELATED APPLICATION

This application is a division of U.S. application Ser. No. 10/991,966, filed Nov. 17, 2004, which claims the benefit of priority under 35 U.S.C. §119(e) to U.S. Provisional Application No. 60/523,840, filed Nov. 19, 2003, U.S. Provisional Application 60/587,787, filed Jul. 13, 2004, and U.S. Provisional Application No. 60/614,683, filed Sep. 30, 2004, each of which is incorporated by reference herein in its entirety, and each of which is hereby made a part of this specification.

FIELD OF THE INVENTION

The present invention relates generally to systems and methods for monitoring glucose in a host. Particularly, a device for continuous glucose sensing is provided with an integrated receiver for single point glucose measurement and subsequent calibration of the continuous glucose sensor within the device.

BACKGROUND OF THE INVENTION

A variety of continual and continuous glucose sensors have been developed for detecting and/or quantifying analytes in a biological fluid sample, for example, glucose sensors that continually or continuously measure glucose concentration in a host. Typically, these glucose sensors require a reference glucose measurement with which to calibrate the sensor-measured glucose values. Additionally, long-term implantable glucose sensors typically request regular updates of calibration, for example new reference glucose values every day, week, or month. Accordingly, a user has typically been required to keep track of and even stay close to (for example, carry) a device associated with the continuous glucose sensor that receives and processes data from the continuous glucose sensor. Additionally, a user has typically been required to carry a separate device that provides a reference glucose value for calibration of the continuous glucose sensor. Many times additional hardware, such as cables, test strips, and other auxiliary devices are necessary to connect, test, and otherwise use the devices. Therefore, the use of a continuous device can be cumbersome, particularly when the user is away from home.

Furthermore, continuous sensors have conventionally been calibrated using a reference glucose monitor that uses different measurement technology than that of the continuous sensor, which can increase the error within the calibrated sensor values. For example, an implantable glucose sensor that contains a membrane containing glucose oxidase is typically calibrated using self-monitoring blood glucose (SMBG) test strip-based measurement values. Unfortunately, such SMBG tests have an error of ±20% and additionally cannot be calibrated by the user. Furthermore, because the reference measurement device (for example, SMBG) is independent from the continuous glucose sensor, the possibility of accuracy in reporting time of SMGB can be prone to human error.

SUMMARY OF THE INVENTION

A continuous glucose sensor that includes simpler or fewer components than prior art sensors, that is user friendly, that exhibits reduced error within the calibrated sensor values, and/or is less prone to human error is desirable.

Accordingly, in a first embodiment, a device for monitoring glucose concentration in a biological sample of a host is provided, the device comprising a continuous glucose sensor that produces a data stream indicative of a host's glucose concentration; an integrated receiver that receives the data stream from the continuous glucose sensor, wherein the integrated receiver comprises a microprocessor comprising programming to process the data stream received from glucose sensor; and a single point glucose monitor adapted to receive a biological sample from the host and measure the concentration of glucose in the sample; wherein the microprocessor further comprises programming to calibrate the data stream using the glucose concentration measured by the single point glucose monitor.

In an aspect of the first embodiment, the continuous glucose sensor comprises a sensing membrane comprising an enzyme; and an electrochemical cell that measures the glucose concentration.

In an aspect of the first embodiment, the single point glucose monitor comprises a sensing membrane comprising an enzyme; and an electrochemical cell that measures a concentration of glucose in the sample.

In an aspect of the first embodiment, the integrated receiver further comprises a user interface for displaying glucose concentration data from at least one of the continuous glucose sensor and the single point glucose monitor.

In a second embodiment, a method for calibrating a continuous glucose sensor in an integrated receiver is provided, the method comprising continually receiving a data stream in the integrated receiver from a continuous glucose sensor; measuring a glucose concentration of a biological sample using a single point glucose monitor integral with the integrated receiver; and calibrating the data stream within the integrated receiver using the glucose concentration measured by the single point glucose monitor.

In an aspect of the second embodiment, the method further comprises the step of displaying the glucose concentration measured by the single point glucose monitor.

In an aspect of the second embodiment, the method further comprises the step of displaying a calibrated data stream.

In a third embodiment, a device for calibrating continuous glucose sensor data is provided, the device comprising a single point glucose monitor adapted to measure a glucose concentration in a biological sample; a receiver for receiving a data stream from a continuous glucose sensor; a microprocessor comprising programming to calibrate the data stream from the continuous glucose sensor using the glucose concentration measured from the single point glucose monitor.

In an aspect of the third embodiment, the continuous glucose sensor comprises a sensing membrane comprising an enzyme; and an electrochemical cell that measures the glucose concentration.

In an aspect of the third embodiment, the single point glucose monitor comprises a sensing membrane comprising an enzyme; and an electrochemical cell that measures the glucose concentration in the biological sample.

In an aspect of the third embodiment, the device further comprises a user interface adapted to display glucose data from at least one of the continuous glucose sensor and the single point glucose monitor.

In an aspect of the third embodiment, the glucose monitor comprises a sensing region comprising a sensing membrane and at least two electrodes, wherein the sensing region is located within the integrated receiver.

In an aspect of the third embodiment, the integrated receiver comprises a removable cartridge, and wherein the sensing region is located within the removable cartridge.

In an aspect of the third embodiment, the integrated receiver comprises a housing, and wherein the glucose monitor comprises a sensing region movably mounted to the integrated receiver housing.

In an aspect of the third embodiment, the device further comprises a stylus movably mounted to the integrated receiver housing, and wherein the sensing region is located on the stylus.

In an aspect of the third embodiment, the device further comprises a receiving chamber located within the integrated receiver housing, and wherein the stylus is received within the receiving chamber for storage.

In an aspect of the third embodiment, the device further comprises a sterile solution chamber located at an end of the receiving chamber such that the sensing region is operably associated with the sterile solution chamber when the stylus is received within the receiving chamber for storage.

In an aspect of the third embodiment, the device further comprises a sterile solution port configured for refilling the sterile solution chamber with a sterile solution.

In an aspect of the third embodiment, the device further comprises a dispensing chamber located in the integrated receiver housing, the dispensing chamber adapted to dispense at least one disposable bioprotective film onto the sensing region.

In an aspect of the third embodiment, the device further comprises a storage chamber located in the integrated receiver housing, the storage chamber adapted to store the disposable bioprotective film.

In an aspect of the third embodiment, the device further comprises a shuttle mechanism located on the integrated receiver housing, the shuttle mechanism adapted to load the disposable bioprotective film into the dispensing chamber.

In an aspect of the third embodiment, the device further comprises at least one bioprotective film that is adapted to stretch or stick onto the sensing region to protect the sensing region from damage, clogging, or contamination from a biological fluid.

In an aspect of the third embodiment, the bioprotective film further comprises a sensing membrane comprising an enzyme.

In an aspect of the third embodiment, the sensing region comprises a sensing membrane and at least two electrodes, wherein the sensing membrane is disposed over the electrodes adapted for measuring a glucose concentration in a biological sample.

In an aspect of the third embodiment, the single point glucose monitor comprises a sensor port that houses a sensing region adapted for measuring a glucose concentration in the biological sample.

In an aspect of the third embodiment, the device further comprises a disposable capillary tube, wherein the capillary tube is configured to create a capillary action capable of drawing a liquid biological sample from a first end of the tube to a second end of the tube.

In an aspect of the third embodiment, the capillary tube comprises a filter configured to permit passage of glucose, but to filter or block passage of an undesired species or a contaminating species in the biological sample.

In an aspect of the third embodiment, the capillary tube further comprises a vent configured to allow displaced air within the capillary tube to escape therefrom.

In an aspect of the third embodiment, n the sensor port comprises a cover adapted for protecting the sensing region.

In an aspect of the third embodiment, the disposable capillary tube comprises a sensing membrane, wherein the sensing membrane comprises a resistance domain, an enzyme domain, an interference domain, and an electrolyte domain.

In an aspect of the third embodiment, the single point glucose monitor and the receiver are detachably connected to each other.

In an aspect of the third embodiment, the single point glucose monitor and the receiver each comprise at least one contact adapted for operable connection when detachably connected to each other.

In an aspect of the third embodiment, the microprocessor is located within the receiver.

In an aspect of the third embodiment, the device further comprises a microprocessor located within the single point glucose monitor, wherein the microprocessor is adapted for communication between the single point glucose monitor and the receiver when the single point glucose monitor contact and the receiver contact are operably connected.

In a fourth embodiment, a device for monitoring a glucose concentration in a biological sample in a host is provided, the device comprising a continuous glucose sensor configured to produce a data stream indicative of a glucose concentration in a biological sample of a host, wherein the glucose sensor comprises a sensing membrane comprising a catalyst, wherein the membrane is operably associated with at least two electrodes that are operably connected to an electrical circuit adapted for continuous glucose sensing; a single point glucose monitor configured to produce a glucose concentration measurement from a biological sample obtained from a host, wherein the glucose monitor comprises a sensing membrane comprising a catalyst, wherein the membrane is operably associated with at least two electrodes that are operably connected to an electrical circuit adapted for measuring the glucose concentration in the biological sample; a receiver integral with the single point glucose monitor adapted to receive a data stream from the continuous glucose sensor; and a microprocessor integral with the single point glucose monitor that comprises programming to calibrate the data stream from the continuous glucose sensor using the glucose concentration measurement from the single point glucose monitor.

DETAILED DESCRIPTION OF THE PREFERRED EMBODIMENT

Figure 1:
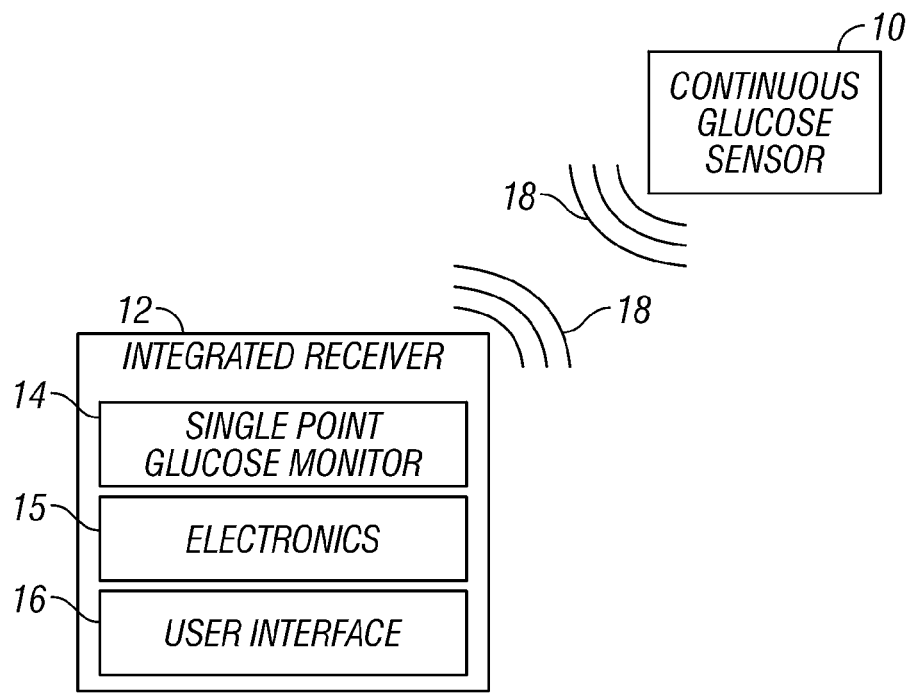
FIG. 1 is a block diagram that illustrates an integrated receiver in one embodiment in wireless communication with a continuous glucose sensor.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

DEFINITIONS

In order to facilitate an understanding of the preferred embodiments, a number of terms are defined below.

The term "continuous glucose sensor," as used herein, is a broad term and are used in its ordinary sense, including, without limitation, a device that continuously or continually measures glucose concentration, for example, at time intervals ranging from fractions of a second up to, for example, 1, 2, or 5 minutes, or longer. It should be understood that continuous glucose sensors can continually or continuously measure glucose concentration without requiring user initiation and/or interaction for each measurement, such as described with reference to U.S. Pat. No. 6,001,067, for example.

The phrase "continuous glucose sensing," as used herein, is a broad term and is used in its ordinary sense, including, without limitation, the period in which monitoring of plasma glucose concentration is continuously or continually performed, for example, at time intervals ranging from fractions of a second up to, for example, 1, 2, or 5 minutes, or longer.

The term "single point glucose monitor," as used herein, is a broad term and is used in its ordinary sense, including, without limitation, a device that can be used to measure a glucose concentration within a host at a single point in time, for example, some embodiments utilize a small volume in vitro glucose monitor that includes an enzyme membrane such as described with reference to U.S. Pat. No. 4,994,167 and U.S. Pat. No. 4,757,022. It should be understood that single point glucose monitors can measure multiple samples (for example, blood or interstitial fluid); however only one sample is measured at a time and typically requires some user initiation and/or interaction.

The term "capillary action," as used herein, is a broad term and is used in its ordinary sense, including, without limitation, the phenomenon of a liquid, such as water or blood, spontaneously creeping up a thin tube or fiber due to adhesive or cohesive forces or surface tension.

The term "biological sample," as used herein, is a broad term and is used in its ordinary sense, including, without limitation, sample of a host body, for example blood, interstitial fluid, spinal fluid, saliva, urine, tears, sweat, or the like.

The term "host," as used herein, is a broad term and is used in its ordinary sense, including, without limitation, mammals such as humans.

The term "biointerface membrane," as used herein, is a broad term and is used in its ordinary sense, including, without limitation, a permeable or semi-permeable membrane that can include two or more domains and is typically constructed of materials of a few microns thickness or more, which can be placed over the sensing region to keep host cells (for example, macrophages) from gaining proximity to, and thereby damaging the sensing membrane or forming a barrier cell layer and interfering with the transport of glucose across the tissue-device interface.

The term "sensing membrane," as used herein, is a broad term and is used in its ordinary sense, including, without limitation, a permeable or semi-permeable membrane that can be comprised of two or more domains and is typically constructed of materials of a few microns thickness or more, which are permeable to oxygen and are optionally permeable to glucose. In one example, the sensing membrane comprises an immobilized glucose oxidase enzyme, which enables an electrochemical reaction to occur to measure a concentration of glucose.

The term "domain," as used herein is a broad term and is used in its ordinary sense, including, without limitation, regions of a membrane that can be layers, uniform or non-uniform gradients (for example, anisotropic), functional aspects of a material, or provided as portions of the membrane.

As used herein, the term "copolymer," as used herein, is a broad term and is used in its ordinary sense, including, without limitation, polymers having two or more different repeat units and includes copolymers, terpolymers, tetrapolymers, etc.

The term "sensing region," as used herein, is a broad term and is used in its ordinary sense, including, without limitation, the region of a monitoring device responsible for the detection of glucose. In one embodiment, the sensing region generally comprises a non-conductive body, a working electrode (anode), a reference electrode and a counter electrode (cathode) passing through and secured within the body forming an electrochemically reactive surface at one location on the body and an electronic connection at another location on the body, and a sensing membrane affixed to the body and covering the electrochemically reactive surface. During general operation of the sensor a biological sample (for example, blood or interstitial fluid) or a portion thereof contacts (for example, directly or after passage through one or more domains of the sensing membrane) an enzyme (for example, glucose oxidase); the reaction of the biological sample (or portion thereof) results in the formation of reaction products that allow a determination of the glucose level in the biological sample.

The term "electrochemically reactive surface," as used herein, is a broad term and is used in its ordinary sense, including, without limitation, the surface of an electrode where an electrochemical reaction takes place. In the case of an electrochemical glucose sensor, hydrogen peroxide produced by an enzyme catalyzed reaction of the glucose being detected reacts at a working electrode creating a measurable electronic current (for example, detection of glucose utilizing glucose oxidase produces $H_2O_2$ as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species (for example, $O_2$) is reduced at the electrode surface in order to balance the current being generated by the working electrode.

The term "electrochemical cell," as used herein, is a broad term and is used in its ordinary sense, including, without limitation, a device in which chemical energy is converted to electrical energy. Such a cell typically consists of two or more electrodes held apart from each other and in contact with an electrolyte solution. Connection of the electrodes to a source of direct electric current renders one of them negatively charged and the other positively charged. Positive ions in the electrolyte migrate to the negative electrode (cathode) and there combine with one or more electrons, losing part or all of their charge and becoming new ions having lower charge or neutral atoms or molecules; at the same time, negative ions migrate to the positive electrode (anode) and transfer one or more electrons to it, also becoming new ions or neutral particles. The overall effect of the two processes is the transfer of electrons from the negative ions to the positive ions, a chemical reaction.

The term "proximal" as used herein, is a broad term and is used in its ordinary sense, including, without limitation, near to a point of reference such as an origin or a point of attachment. For example, in some embodiments of a sensing membrane that covers an electrochemically reactive surface, the electrolyte domain is located more proximal to the electrochemically reactive surface than the interference domain.

The term "distal" as used herein, is a broad term and is used in its ordinary sense, including, without limitation, spaced relatively far from a point of reference, such as an origin or a point of attachment. For example, in some embodiments of a sensing membrane that covers an electrochemically reactive surface, a resistance domain is located more distal to the electrochemically reactive surfaces than the enzyme domain.

The term "substantially" as used herein, is a broad term and is used in its ordinary sense, including, without limitation, being largely but not necessarily wholly that which is specified.

The terms "microprocessor" and "processor," as used herein, are broad terms and are used in their ordinary sense, including, without limitation, a computer system or state machine designed to perform arithmetic and logic operations using logic circuitry that responds to and processes the basic instructions that drive a computer.

The term "EEPROM," as used herein, is a broad term and is used in its ordinary sense, including, without limitation, electrically erasable programmable read-only memory, which is user-modifiable read-only memory (ROM) that can be erased and reprogrammed (for example, written to) repeatedly through the application of higher than normal electrical voltage.

The term "SRAM," as used herein, is a broad term and is used in its ordinary sense, including, without limitation, static random access memory (RAM) that retains data bits in its memory as long as power is being supplied.

The term "A/D Converter," as used herein, is a broad term and is used in its ordinary sense, including, without limitation, hardware and/or software that converts analog electrical signals into corresponding digital signals.

The term "RF transceiver," as used herein, is a broad term and is used in its ordinary sense, including, without limitation, a radio frequency transmitter and/or receiver for transmitting and/or receiving signals.

The terms "raw data stream" and "data stream," as used herein, are broad terms and are used in their ordinary sense, including, without limitation, an analog or digital signal directly related to the measured glucose from the glucose sensor. In one example, the raw data stream is digital data in "counts" converted by an A/D converter from an analog signal (for example, voltage or amps) representative of a glucose concentration. The terms broadly encompass a plurality of time spaced data points from a substantially continuous glucose sensor, which comprises individual measurements taken at time intervals ranging from fractions of a second up to, for example, 1, 2, or 5 minutes or longer.

The term "counts," as used herein, is a broad term and is used in its ordinary sense, including, without limitation, a unit of measurement of a digital signal. In one example, a raw data stream measured in counts is directly related to a voltage (for example, converted by an A/D converter), which is directly related to current from the working electrode. In another example, counter electrode voltage measured in counts is directly related to a voltage.

The term "electronic circuitry," as used herein, is a broad term and is used in its ordinary sense, including, without limitation, the components (for example, hardware and/or software) of a device configured to process data. In the case of a glucose-measuring device, the data includes biological information obtained by a sensor regarding a particular glucose in a biological fluid, thereby providing data regarding the amount of that glucose in the fluid. U.S. Pat. Nos. 4,757,022, 5,497,772 and 4,787,398, which are hereby incorporated by reference, describe suitable electronic circuits that can be utilized with devices of the preferred embodiments.

The term "potentiostat," as used herein, is a broad term and is used in its ordinary sense, including, but not limited to, an electrical system that applies a potential between the working and reference electrodes of a two- or three-electrode cell at a preset value and measures the current flow through the working electrode. The potentiostat forces whatever current is necessary to flow between the working and reference (2 electrode) or counter (3 electrode) electrodes to keep the desired potential, as long as the needed cell voltage and current do not exceed the compliance limits of the potentiostat.

The term "electrical potential," as used herein, is a broad term and is used in its ordinary sense, including, without limitation, the electrical potential difference between two points in a circuit which is the cause of the flow of a current.

The terms "operably connected" and "operably linked," as used herein, are broad terms and are used in their ordinary sense, including, without limitation, one or more components being linked to another component(s) in a manner that allows transmission of signals between the components. For example, one or more electrodes can be used to detect the amount of glucose in a sample and convert that information into a signal. The signal can then be transmitted to an electronic circuit. In this case, the electrode is "operably linked" to the electronic circuit. These terms are broad enough to include wireless connectivity.

The term "linear regression," as used herein, is a broad term and is used in its ordinary sense, including, without limitation, finding a line in which a set of data has a minimal measurement from that line. Byproducts of this algorithm include a slope, a y-intercept, and an R-Squared value that determine how well the measurement data fits the line.

The term "non-linear regression," as used herein, is a broad term and is used in its ordinary sense, including, without limitation, fitting a set of data to describe the relationship between a response variable and one or more explanatory variables in a non-linear fashion.

Overview

FIG. 1 is a perspective view of a device in one embodiment including a continuous glucose sensor and an integrated receiver that has a single point glucose monitor thereon. The continuous glucose sensor 10 continuously measures glucose concentration in a host to provide a data stream representative of the host's glucose concentration, such as described in more detail below with reference to FIGS. 2 and 3. In general, the integrated receiver 12 includes a single point glucose monitor 14, electronic circuitry that processes data from the continuous glucose sensor 10 and the single point glucose monitor 14, and a user interface 16 that displays glucose data to a user, all of which are described in more detail with reference to FIGS. 4 to 10. Wireless transmissions 18 allow communication between the glucose sensor 10 and the integrated receiver 12, for example, so that the integrated receiver 12 can receive a data stream from the continuous glucose sensor 10.

Continuous Glucose Sensor

The preferred embodiments provide a continuous glucose sensor that measures a concentration of glucose or a substance indicative of the concentration or presence of the glucose. In some embodiments, the glucose sensor is an invasive, minimally-invasive, or non-invasive device, for example a subcutaneous, transdermal, or intravascular device. In some embodiments, the device can analyze a plurality of intermittent biological samples. The glucose sensor can use any method of glucose-measurement, including enzymatic, chemical, physical, electrochemical, spectrophotometric, polarimetric, calorimetric, radiometric, or the like. In alternative embodiments, the sensor can be any sensor capable of determining the level of an analyte in the body, for example oxygen, lactase, hormones, cholesterol, medicaments, viruses, or the like.

The glucose sensor uses any known method to provide an output signal indicative of the concentration of the glucose. The output signal is typically a raw data stream that is used to provide a useful value of the measured glucose concentration to a patient or doctor, for example.

One exemplary embodiment is described in detail below, which utilizes an implantable glucose sensor. However, it should be understood that the devices and methods described herein can be applied to any device capable of continually or continuously detecting a concentration of analyte of interest and providing an output signal that represents the concentration of that analyte.

Figure 2A:
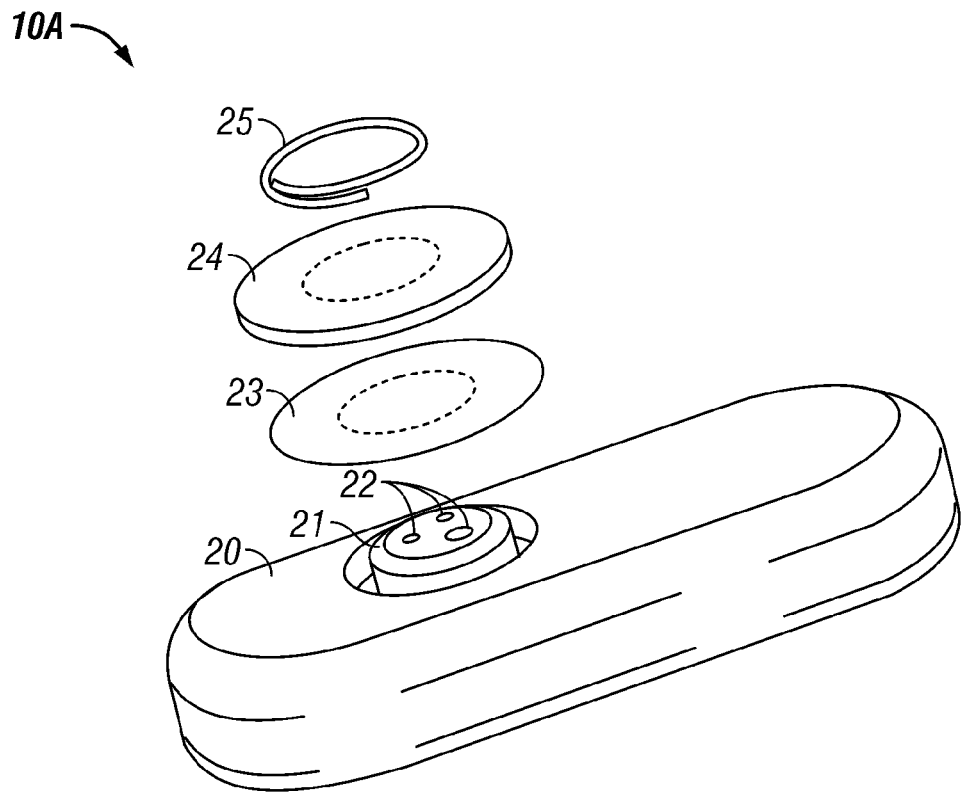
FIG. 2A is an exploded perspective view of one exemplary embodiment of a continuous glucose sensor.
Figure 3:
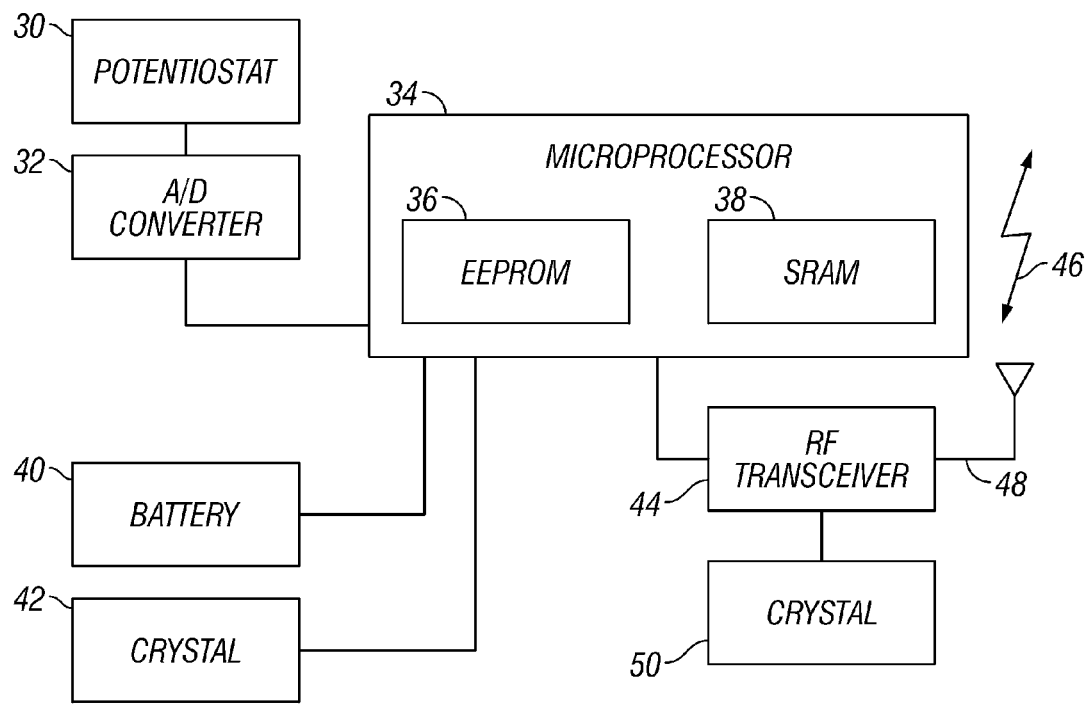
FIG. 3 is a block diagram that illustrates the continuous glucose sensor electronics in one embodiment.

FIG. 2A is an exploded perspective view of one exemplary embodiment of a continuous glucose sensor 10a. In this embodiment, the sensor is preferably wholly implanted into the subcutaneous tissue of a host, such as described in co-pending patent application Ser. No. 10/885,476 filed Jul. 6, 2004 and entitled "SYSTEMS AND METHODS FOR MANUFACTURE OF AN ANALYTE-MEASURING DEVICE INCLUDING A MEMBRANE SYSTEM"; co-pending U.S. patent application Ser. No. 10/838,912 filed May 3, 2004 and entitled, "IMPLANTABLE ANALYTE SENSOR"; U.S. patent application Ser. No. 10/789,359 filed Feb. 26, 2004 and entitled, "INTEGRATED DELIVERY DEVICE FOR A CONTINUOUS GLUCOSE SENSOR"; U.S. application Ser. No. 10/646,333 filed Aug. 22, 2003 entitled, "OPTIMIZED SENSOR GEOMETRY FOR AN IMPLANTABLE GLUCOSE SENSOR"; U.S. application Ser. No. 10/633,367 filed Aug. 1, 2003 entitled, "SYSTEM AND METHODS FOR PROCESSING ANALYTE SENSOR DATA"; and U.S. Pat. No. 6,001,067 issued Dec. 14, 1999 and entitled "DEVICE AND METHOD FOR DETERMINING ANALYTE LEVELS", each of which are incorporated herein by reference in their entirety. In this exemplary embodiment, a body 20 and a sensing region 21 house the electrodes 22 and sensor electronics (FIG. 3). The three electrodes 22 are operably connected to the sensor electronics (FIG. 3) and are covered by a sensing membrane 23 and a biointerface membrane 24, which are attached by a clip 25.

In one embodiment, the three electrodes 22 include a platinum working electrode, a platinum counter electrode, and a silver/silver chloride reference electrode. The top ends of the electrodes are in contact with an electrolyte phase (not shown), which is a free-flowing fluid phase disposed between the sensing membrane 23 and the electrodes 22. The sensing membrane 23 includes an enzyme, for example, glucose oxidase, and covers the electrolyte phase. The biointerface membrane 24 covers the sensing membrane 23 and serves, at least in part, to protect the sensor 10a from external forces that can result in environmental stress cracking of the sensing membrane 23. Copending U.S. patent application Ser. No. 10/647,065, entitled, "POROUS MEMBRANES FOR USE WITH IMPLANTABLE DEVICES," describes a biointerface membrane that can be used in conjunction with the preferred embodiments, and is incorporated herein by reference in its entirety.

In one embodiment, the biointerface membrane 24 generally includes a cell disruptive domain most distal from the electrochemically reactive surfaces and a cell impermeable domain less distal from the electrochemically reactive surfaces than the cell disruptive domain. The cell disruptive domain is preferably designed to support tissue ingrowth, disrupt contractile forces typically found in a foreign body response, encourage vascularity within the membrane, and disrupt the formation of a barrier cell layer. The cell impermeable domain is preferably resistant to cellular attachment, impermeable to cells, and composed of a biostable material.

In one embodiment, the sensing membrane 23 generally provides one or more of the following functions: 1) protection of the exposed electrode surface from the biological environment, 2) diffusion resistance (limitation) of the analyte, 3) a catalyst for enabling an enzymatic reaction, 4) limitation or blocking of interfering species, and 5) hydrophilicity at the electrochemically reactive surfaces of the sensor interface, such as described in co-pending U.S. patent application Ser. No. 10/838,912, filed May 3, 2004 and entitled "IMPLANTABLE ANALYTE SENSOR," which is incorporated herein by reference in its entirety. Accordingly, the sensing membrane 23 preferably includes a plurality of domains or layers, for example, an electrolyte domain, an interference domain, an enzyme domain (for example, glucose oxidase), a resistance domain, and can additionally include an oxygen domain (not shown), and/or a bioprotective domain (not shown), such as described in more detail in the above-cited U.S. patent application Ser. No. 10/838,912. However, it is understood that a sensing membrane modified for other devices, for example, by including fewer or additional domains is within the scope of the preferred embodiments.

In some embodiments, the domains of the biointerface and sensing membranes are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers. Co-pending U.S. patent application Ser. No. 10/838,912, which is incorporated herein by reference in its entirety, describes biointerface and sensing membrane configurations and materials that can be applied to the preferred embodiments.

In the illustrated embodiment, the counter electrode is provided to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction:

$$\text{Glucose} + O_2 \rightarrow \text{Gluconate} + H_2O_2$$

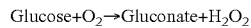

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2e^-$), and one oxygen molecule ($O_2$).

In one embodiment, a potentiostat is employed to monitor the electrochemical reaction at the electrochemical cell. The potentiostat applies a constant potential to the working and reference electrodes to determine a current value. The current that is produced at the working electrode (and flows through the circuitry to the counter electrode) is substantially proportional to the amount of $H_2O_2$ that diffuses to the working electrode. Accordingly, a raw signal can be produced that is representative of the concentration of glucose in the user's body, and therefore can be utilized to estimate a meaningful glucose value, such as described herein.

Figure 2B:
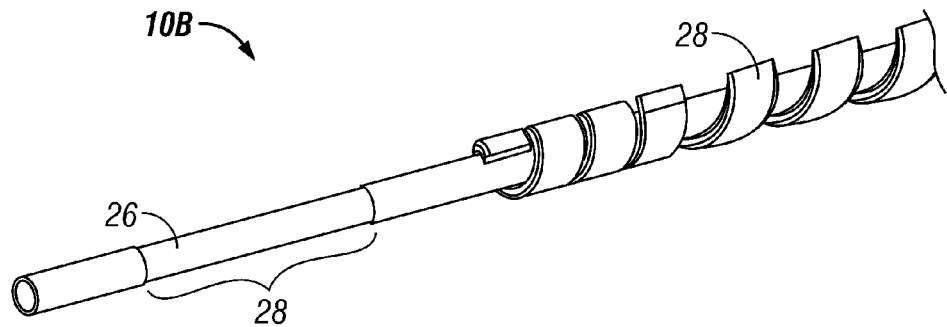
FIG. 2B is an expanded view of an alternative exemplary embodiment of a continuous glucose sensor, illustrating the in vivo portion of the sensor.

FIG. 2B is an expanded view of an alternative exemplary embodiment of a continuous glucose sensor, illustrating the in vivo portion of the sensor. U.S. Provisional Application 60/587,787, filed Jul. 13, 2004 and U.S. Provisional Application 60/614,683, filed Sep. 30, 2004, describe systems and methods suitable for the transcutaneous sensor of the illustrated embodiment; however, one skilled in the art appreciates a variety of transcutaneous sensors that can benefit from the integrated receiver of the preferred embodiments.

In this embodiment, the in vivo portion of the sensor 10b is the portion adapted for insertion under the host's skin, while an ex vivo portion of the sensor 10b is the portion that remains above the host's skin after sensor insertion and operably connects to an electronics unit (not shown). The sensor 10b two or more electrodes: a working electrode 26 and at least one additional electrode 28, which can function as a counter and/or reference electrode, hereinafter referred to as the reference electrode. Each electrode is formed from a fine wire, with a diameter in the range of 0.001 to 0.010 inches, for example, and can be formed from plated wire or bulk material.

In one embodiment, the working electrode 26 comprises a wire formed from a conductive material, such as platinum, palladium, graphite, gold, carbon, conductive polymer, or the like. The working electrode 26 is configured and arranged to measure the concentration of an analyte. The working electrode 20 is covered with an insulating material, for example a non-conductive polymer. Dip-coating, spray-coating, or other coating or deposition techniques can be used to deposit the insulating material on the working electrode, for example. In one preferred embodiment, the insulating material comprises Parylene, which can be an advantageous conformal coating for its strength, lubricity, and electrical insulation properties, however, a variety of other insulating materials can be used, for example, fluorinated polymers, polyethyleneterephthalate, polyurethane, polyimide, or the like.

The reference electrode 28, which can function as a reference electrode alone, or as a dual reference and counter electrode, is formed from silver, Silver/Silver chloride, or the like. In one embodiment, the reference electrode 28 is formed from a flat wire with rounded edges in order to decrease sharp edges and increase host comfort. Preferably, the reference electrode 28 is juxtapositioned and/or twisted with or around the working electrode 26; however other configurations are also possible. In some embodiments, the reference electrode 28 is helically wound around the working electrode 26 (see FIG. 2B). The assembly of wires is then optionally coated together with an insulating material, similar to that described above, in order to provide an insulating attachment. Some portion of the coated assembly structure is then stripped, for example using an excimer laser, chemical etching, or the like, to expose the necessary electroactive surfaces. In one implementation, a window 28 is formed on the insulating material to expose an electroactive surface of the working electrode and at least some edges of the sensor are stripped to expose sections of electroactive surface on the reference electrode. Other methods and configurations for exposing electroactive surfaces are also possible, for example by exposing the surfaces of the working electrode 26 between the coils of the reference electrode 28. In some alternative embodiments, additional electrodes can be included within the assembly, for example, a three-electrode system (working, reference, and counter electrodes) and/or including an additional working electrode (which can be used to generate oxygen, configured as a baseline subtracting electrode, or configured for measuring additional analytes, for example).

A sensing membrane (not shown) is deposited over the electroactive surfaces of the sensor 10b (working electrode and optionally reference electrode) and includes a plurality of domains or layers, such as described above, with reference to FIG. 2A. The sensing membrane can be deposited on the exposed electroactive surfaces using known thin film techniques (for example, spraying, electro-depositing, dipping, or the like). In one exemplary embodiment, each domain is deposited by dipping the sensor into a solution and drawing out the sensor at a speed that provides the appropriate domain thickness. In general, the membrane system can be disposed over (deposited on) the electroactive surfaces using methods appreciated by one skilled in the art.

In the illustrated embodiment, the sensor glucose oxidase electrochemical sensor, wherein the working electrode 26 measures the hydrogen peroxide produced by an enzyme catalyzed reaction of the analyte being detected and creates a measurable electronic current (for example, detection of glucose utilizing glucose oxidase produces $H_2O_2$ peroxide as a by product, $H_2O_2$ reacts with the surface of the working electrode producing two protons ($2H^+$), two electrons ($2e^-$) and one molecule of oxygen ($O_2$) which produces the electronic current being detected), such as described in more detail above and as is appreciated by one skilled in the art.

FIG. 3 is a block diagram that illustrates the continuous glucose sensor electronics in one embodiment. In this embodiment, a potentiostat 30 is shown, which is operably connected to electrodes 24a (FIG. 2) or 24b (FIG. 3) to obtain a current value, and includes a resistor (not shown) that translates the current into voltage. An A/D converter 32 digitizes the analog signal into "counts" for processing. Accordingly, the resulting raw data stream in counts is directly related to the current measured by the potentiostat 30.

A microprocessor 34 is the central control unit that houses EEPROM 36 and SRAM 38, and controls the processing of the sensor electronics. Certain alternative embodiments can utilize a computer system other than a microprocessor to process data as described herein. In other alternative embodiments, an application-specific integrated circuit (ASIC) can be used for some or all the sensor's central processing. The EEPROM 36 provides semi-permanent storage of data, for example, storing data such as sensor identifier (ID) and programming to process data streams (for example, programming for data smoothing and/or replacement of signal artifacts such as described in copending U.S. patent application entitled, "SYSTEMS AND METHODS FOR REPLACING SIGNAL ARTIFACTS IN A GLUCOSE SENSOR DATA STREAM," filed Aug. 22, 2003). The SRAM 38 can be used for the system's cache memory, for example for temporarily storing recent sensor data. In some alternative embodiments, memory storage components comparable to EEPROM and SRAM can be used instead of or in addition to the preferred hardware, such as dynamic RAM, non-static RAM, rewritable ROMs, flash memory, or the like.

A battery 40 is operably connected to the microprocessor 34 and provides the necessary power for the sensor 10. In one embodiment, the battery is a Lithium Manganese Dioxide battery, however any appropriately sized and powered battery can be used (for example, AAA, Nickel-cadmium, Zinc-carbon, Alkaline, Lithium, Nickel-metal hydride, Lithium-ion, Zinc-air, Zinc-mercury oxide, Silver-zinc, and/or hermetically-sealed). In some embodiments the battery is rechargeable. In some embodiments, a plurality of batteries can be used to power the system. A Quartz Crystal 42 is operably connected to the microprocessor 34 and maintains system time for the computer system as a whole.

An RF Transceiver 44 is operably connected to the microprocessor 34 and transmits the sensor data from the sensor 10 to a receiver (see FIGS. 4 to 8) within a wireless transmission 46 via antenna 48. Although an RF transceiver is shown here, some other embodiments can include a wired rather than wireless connection to the receiver. In yet other embodiments, the receiver can be transcutaneously powered via an inductive coupling, for example. A second quartz crystal 50 provides the system time for synchronizing the data transmissions from the RF transceiver. The transceiver 44 can be substituted with a transmitter in other embodiments. In some alternative embodiments other mechanisms such as optical, infrared radiation (IR), ultrasonic, or the like can be used to transmit and/or receive data.

In one alternative embodiment, the continuous glucose sensor comprises a transcutaneous sensor such as described in U.S. Pat. No. 6,565,509 to Say et al. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al. In another alternative embodiment, the continuous glucose sensor comprises a refillable subcutaneous sensor such as described with reference to U.S. Pat. No. 6,512,939 to Colvin et al. In another alternative embodiment, the continuous glucose sensor comprises an intravascular sensor such as described with reference to U.S. Pat. No. 6,477,395 to Schulman et al. In another alternative embodiment, the continuous glucose sensor comprises an intravascular sensor such as described with reference to U.S. Pat. No. 6,424,847 to Mastrototaro et al. All of the above patents are incorporated in their entirety herein by reference.

Although a few exemplary embodiments of continuous glucose sensors are illustrated and described herein, it should be understood that the disclosed embodiments are applicable to a variety of continuous glucose sensor configurations.

Integrated Receiver

Figure 8:
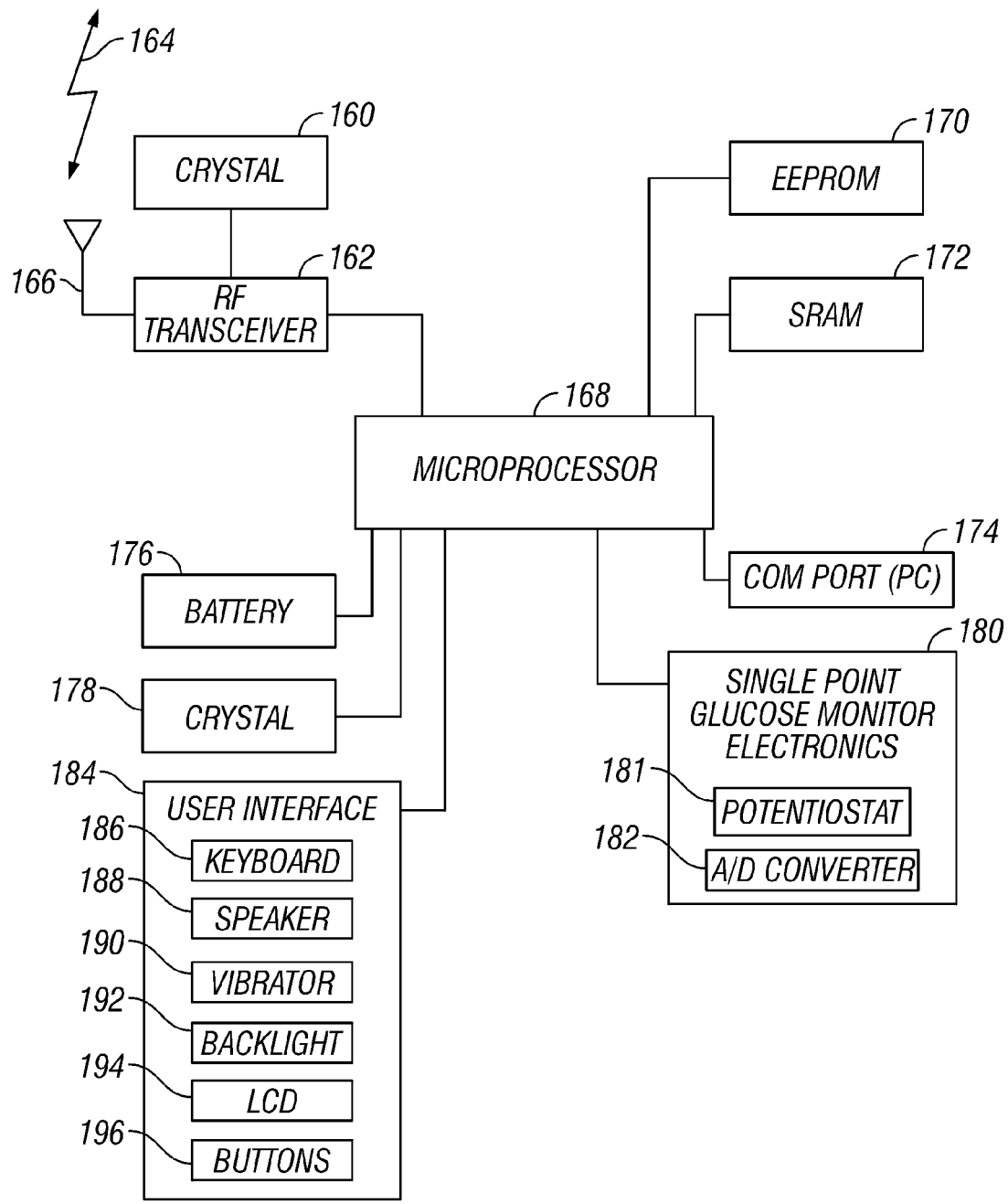
FIG. 8 is a block diagram that illustrates integrated receiver electronics in one embodiment.
Figure 9:
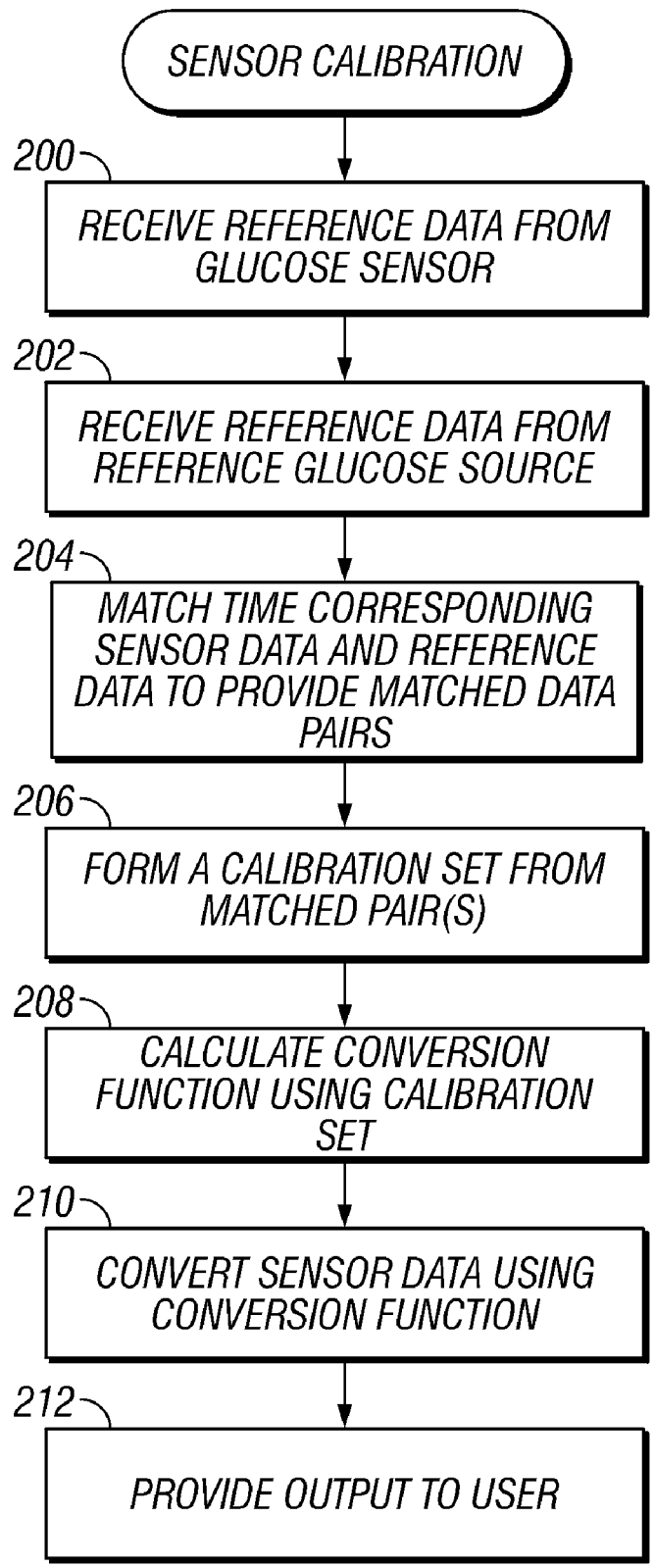
FIG. 9 is a flow chart that illustrates the process of initial calibration of the continuous glucose sensor and data output of the integrated receiver in one embodiment.
Figure 10:
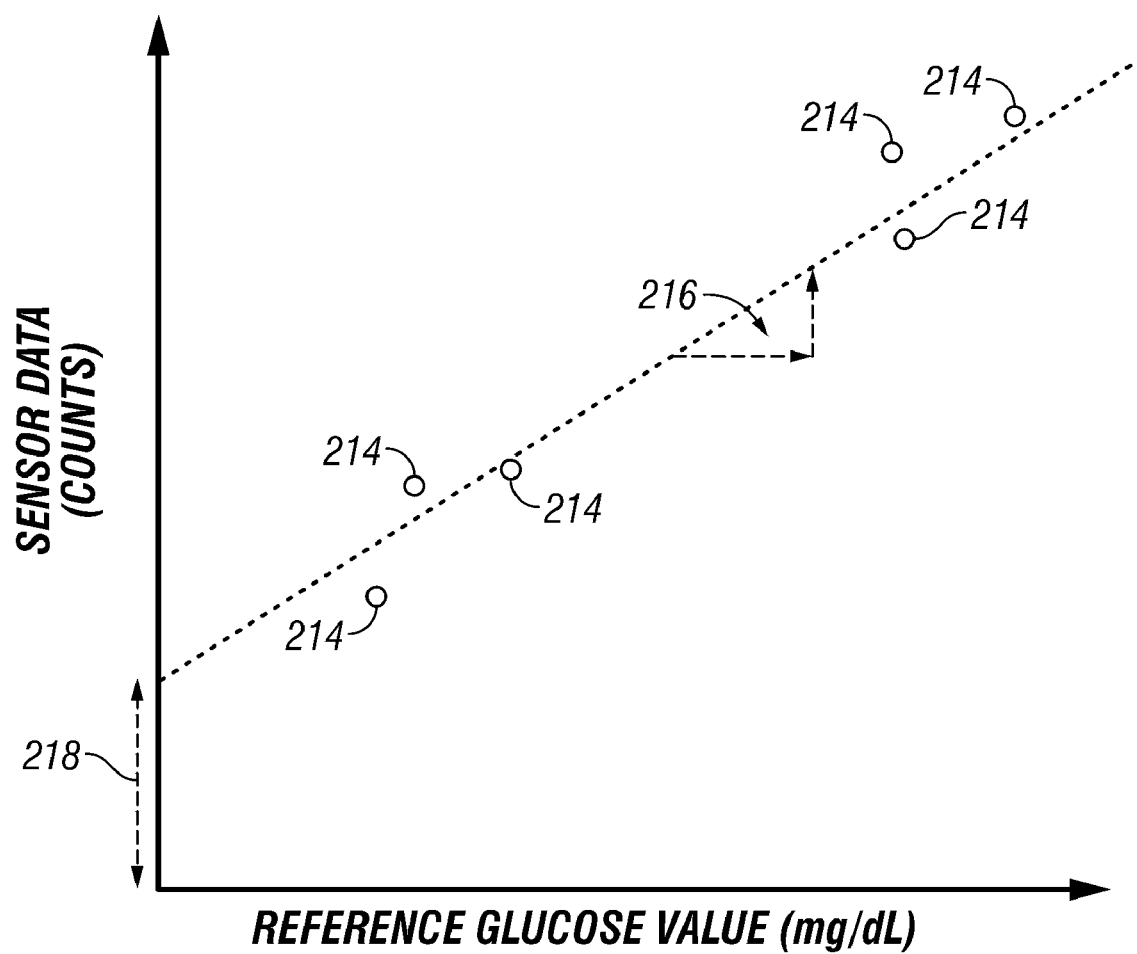
FIG. 10 is a graph that illustrates one exemplary embodiment of a regression performed on a calibration set to create a conversion function.

The integrated receiver provides an integrated housing that includes a single point glucose monitor, electronics (for example, hardware and software) useful to receive and process data from the continuous glucose sensor and the single point glucose monitor, and a user interface that displays processed data to a user (for example, patient or doctor). FIGS. 4 to 7 illustrate preferred embodiments of the integrated receiver with a single point glucose monitor. FIGS. 8 to 10 illustrate some preferred electronics and data processing within the integrated receiver that are applicable to all embodiments of the integrated receiver (for example, FIGS. 4 to 7). Because the single point glucose monitor is integrated into the continuous sensor's receiver housing, there is no need for a separate glucose monitor to provide reference values for calibration or the like.

In the illustrated embodiments, the single point glucose monitor includes a meter for measuring glucose within a biological sample including a sensing region that has a sensing membrane impregnated with an enzyme, similar to the sensing membrane described with reference to FIG. 2, and such as described with reference to FIGS. 4 to 7. However, in alternative embodiments, the single point glucose monitor can use other measurement techniques such as optical, for example.

Figure 4A:
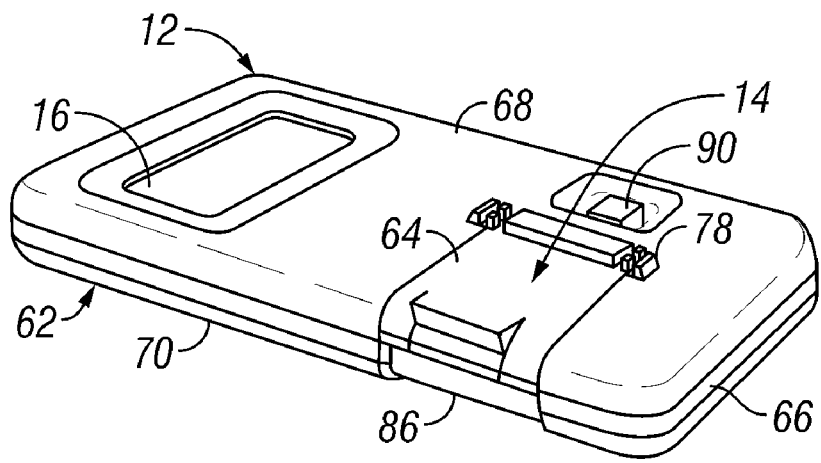
FIG. 4A is a perspective view of an integrated receiver in one embodiment showing a single point glucose monitor in its closed position.
Figure 4B:
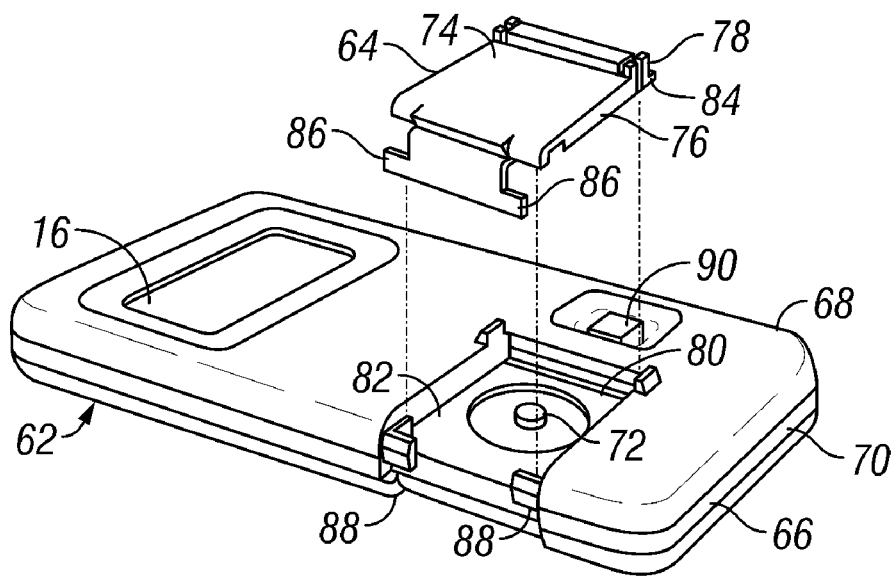
FIG. 4B is an exploded perspective view of the integrated receiver of FIG. 4A showing the single point glucose monitor with a cover removed.

FIG. 4A is a perspective view of an integrated receiver in one embodiment showing a single point glucose monitor in its closed position. FIG. 4B is an exploded perspective view of the integrated receiver, showing the single point glucose monitor with the cover removed to reveal the receptacle inside. The integrated receiver 12 provides a housing that integrates a single point glucose monitor 14 and electronics (FIG. 8) useful to receive, process and display data on the user interface 16. The single point glucose monitor permits rapid and accurate measurement of the amount of a particular substance (for example, glucose) in a biological fluid.

The integrated receiver 12 includes a main housing 62 and a cartridge 64 that is removably mounted on the housing 62, which permits the cartridge 64 to be disposable and replaceable as needed. The housing 62 includes a case 66 having an upper portion 68 and a lower portion 70. The upper portion 68 and lower portion 70 are connected together by any particular fastening means such as several screws (not shown).

The main housing 62 also includes electronic circuitry operably connected to at least two electrodes (not shown). The electrodes are preferably mounted within a sensing region 72 that supports the electrodes as they extend upwardly therein. A sensing membrane (not shown) overlays the electrodes on the sensing region 72 and is operably associated with the electrodes when the cartridge is removably mounted on the housing. The cartridge 64 also includes means for protecting the sensing membrane when not in use. The protection means is preferably a cover 74 that is movably mounted on a body portion 76 of the cartridge 64. Alternatively, the cover 74 can be mounted on the case 66. In the illustrated embodiment, a hinge assembly 78 movably mounts the cover 74 on the body portion 76.

Generally, the cover 74 has a first position such as shown in FIG. 4A in which it protects the membrane, and a second position. Access to the sensing membrane is preferable in order to conveniently place the biological fluid sample on the sensing membrane for analysis.

The housing 62 preferably defines a well 80 having a bottom 82. In practice, the biological fluid sample is placed on the sensing region 72 in the well 80 for analysis. Generally, the well 80 defines an opening of less than 4 millimeters in diameter and less than 2 millimeters in depth. As a result, the well has a volume of less than about 0.1 to 0.2 cubic centimeters. These dimensions substantially minimize the size of the biological fluid sample necessary for analysis down to the sample sizes as small as about five microliters. Because the size of the sample can be particularly small, compensation for temperature changes during analysis that was often necessary with previous devices can be avoided.

The protection means of the cartridge 64 preferably also includes means for sealing the well 80 and hence the sensing region including the sensing membrane, which is disposed at the bottom of the well 80, from the ambient surroundings.

A retaining means is also provided for releasably retaining the cartridge 64 and its body portion 76 on the housing 62. The retaining means preferably includes a detent 84 on the cartridge 64, which is received in a recess defined by the upper portion 68 of the case 66. The retaining means also preferably includes at least one, preferably two wings 86 on the body portion 76 of the cartridge 64 which are received in one or more slots 88 on the case 66. The slots 88 are generally perpendicular to the cover 74 so that opening the cover will not disengage the wings 86 from the slots 88.

The sensing region 72, in which the electrodes are disposed, is preferably generally annular in design with the interior portion thereof filled with an electrically nonconductive support material such as a hardened polyepoxide-containing resin. The electrically nonconductive support material and the top (electrochemically reactive) surfaces of the electrodes define a sensing membrane contact surface. Namely, the sensing membrane can be stretched over the contact surface to more effectively place the membrane in operative association with the electrodes (not shown). In an alternative embodiment of the sensing region 72, the electrodes can be deposited onto a ceramic surface, and an electrically nonconductive material can be applied as a coating over the electrodes to form an insulating barrier. A portion of each electrode, however, is not coated to form a membrane contact surface so that a membrane can be applied over the electrodes in operative contact therewith.

Generally, the sensing membrane can be constructed substantially similar to the sensing membrane described with reference to FIG. 2. For example, the sensing membrane includes a resistance domain most distal from the electrochemically reactive surfaces, an enzyme domain less distal from the electrochemically reactive surfaces than the resistance domain, an interference domain less distal from the electrochemically reactive surfaces than the enzyme domain, and an electrolyte domain adjacent to the electrochemically reactive surfaces. However, it is understood that the sensing membrane can be modified for other devices, for example, by including fewer or additional domains. Furthermore, design considerations for the sensing membrane of the single point glucose monitor can differ from that of the continuous glucose sensor due to oxygen availability, for example.

In some embodiments, the domains of the sensing membrane are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers.

The cover 74 is preferably provided with a closure means (not shown) such as one or more latches that engage the body portion 76. Generally, the force necessary to disengage the closure means from the body portion should be less than that necessary to disengage the wings 86 from the slots 88. In this manner, an operator can easily open the cover 74 without accidentally disengaging the cartridge 64 from the main housing 62.

The sensing region 72, including the electrodes and sensing membrane, contacts the body fluid sample for analysis. The sensing region 72 is operably associated with the electronic circuitry (see FIG. 8) that analyzes the current from the reaction of the components in the body fluid with the electrodes. The electronic circuitry is in turn operably associated with the user interface 16 (for example, such as a liquid crystal display) to indicate glucose concentration.

In one embodiment, the electrode configuration includes a three-electrode electrochemical cell, which in combination with the chemical reactions occurring in the sensing membrane and on the electrochemically reactive surfaces, makes possible consistent electrode behavior and, in particular, performance of a reference electrode that is stable with time. However, in alternative embodiments, wherein the electrode configuration includes a two-electrode electrochemical cell with a reference cathodic, chloride ions will be lost from the reference electrode that eventually leads to unstable electrode behavior. According to the preferred embodiments, permanent stable reference electrode behavior is achieved when the hydrogen peroxide produced in the membrane oxidizes the silver metal to silver oxide which is then converted to silver chloride by chloride ion. Advantages include ease of manufacturing of the electrode, self-forming and self-maintaining electrode behavior, and long-term reference electrode stability.

In general, the glucose measurement technique of the integrated receiver 12 is similar to that described with reference to FIGS. 2 and 3, above, however the electronics are adapted for single point measurement. The electronics associated with the integrated receiver 12 are described in more detail below with reference to FIG. 8. Generally, glucose from a biological sample produces a current flow at a working electrode, with equal current provided by a counter electrode in a reference circuit. The current is converted in an analog section by a current to voltage converter to a voltage, which is inverted, level-shifted, and delivered to an A/D converter in the microprocessor (see FIG. 8). As part of the calibration, the microprocessor can set the analog gain via its control port. The A/D converter is preferably activated at one-second intervals. The microprocessor looks at the converter output with any number of pattern recognition algorithms known to those skilled in the art until a glucose peak is identified. A timer is then activated for about 30 seconds at the end of which time the difference between the first and last electrode current values is calculated. This difference is then divided by the value stored in the memory during instrument calibration and is then multiplied by the calibration glucose concentration. The result includes a calibrated glucose concentration value that is meaningful to a user, and useful in calibrating the data stream from the continuous glucose sensor 10, for example.

The single point glucose monitor described with reference to FIGS. 4A and 4B can be calibrated by the user as described in more detail with reference to U.S. Pat. Nos. 4,994,167 and 4,757,022, both of which are incorporated herein in their entirety. The ability to calibrate the glucose monitor is particularly advantageous, for example, as compared to a conventional test strip, which cannot be calibrated by the user.

Additionally, the similarity of the sensing membranes used for the continuous glucose sensor and the single point glucose sensor provides an internal control that creates increased reliability by nature of consistency and decreased error potential that can otherwise be increased due to combining dissimilar measurement techniques. Additionally, the disclosed membrane system is known to provide longevity, repeatability, and cost effectiveness, for example as compared to single use strips, or the like.

During the data processing, prompts or messages can be displayed on the user interface 16 to guide the user through the calibration and sample measurement procedures. In addition, prompts can be displayed to inform the user about necessary maintenance procedures, such as "Replace Sensor" or "Replace Battery." An on/off button 90 preferably initiates the operation and calibration sequences.

Methods and devices that can be suitable for use in conjunction with aspects of the above-described preferred embodiments are disclosed in copending applications including U.S. Pat. No. 4,994,167 and U.S. Pat. No. 4,757,022. The integrated receiver electronics and its integration with the continuous glucose sensor are described in more detail below with reference to FIGS. 8 to 10.

Figure 5A:
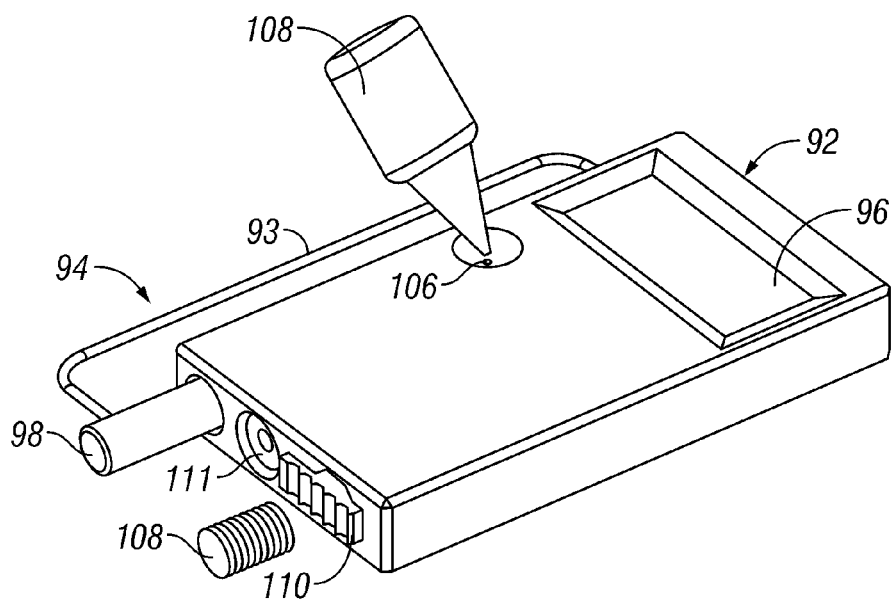
FIG. 5A is a perspective view of an integrated receiver housing in another embodiment, showing a single point glucose monitor including a stylus movably mounted to the integrated receiver, wherein the stylus is shown in a storage position.
Figure 5B:
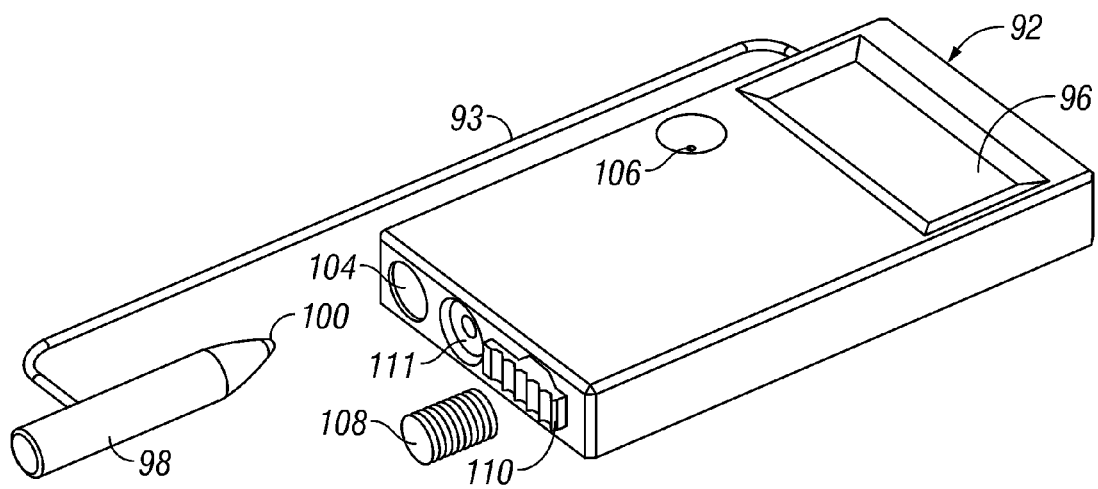
FIG. 5B is a perspective view of the integrated housing of FIG. 5A, showing the stylus in a testing position.
Figure 5C:
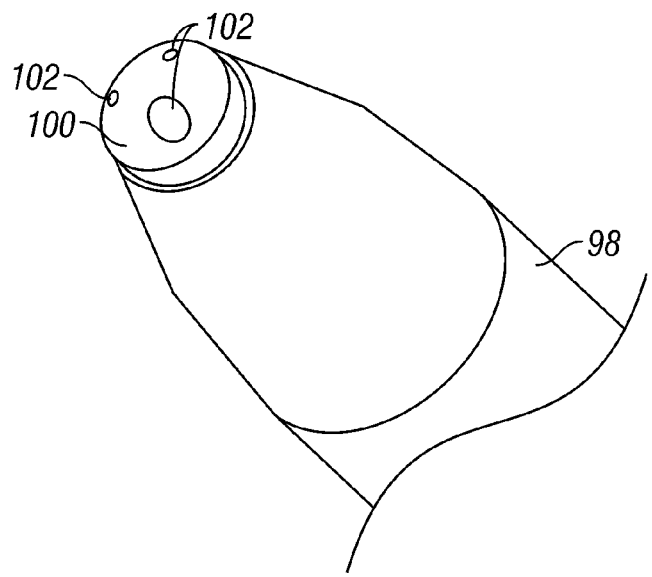
FIG. 5C is a perspective view of a portion of the stylus of FIG. 5A, showing the sensing region.
Figure 5D:
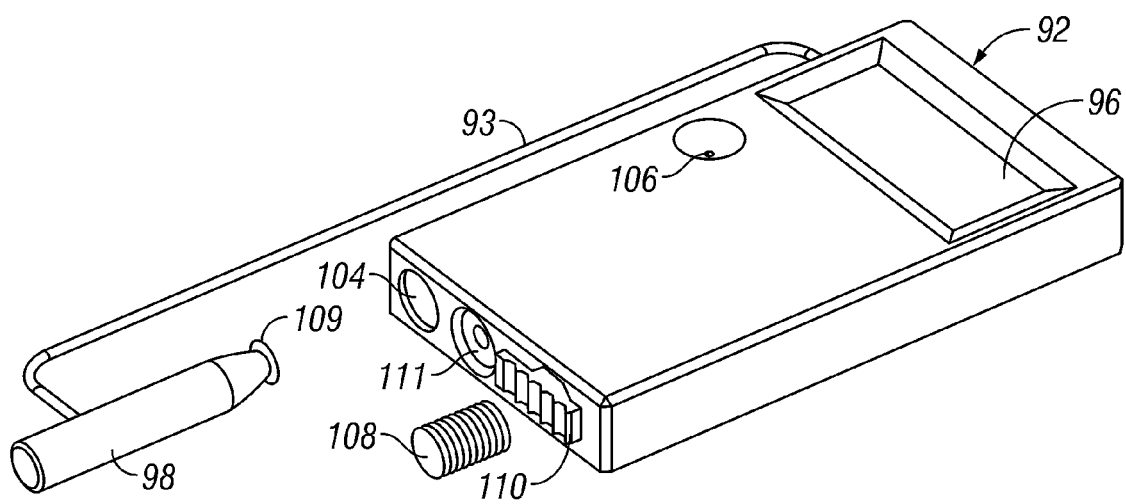
FIG. 5D is a perspective view of the integrated receiver housing of FIG. 5A, showing the stylus loaded with a disposable film, and in its testing position.
Figure 5E:
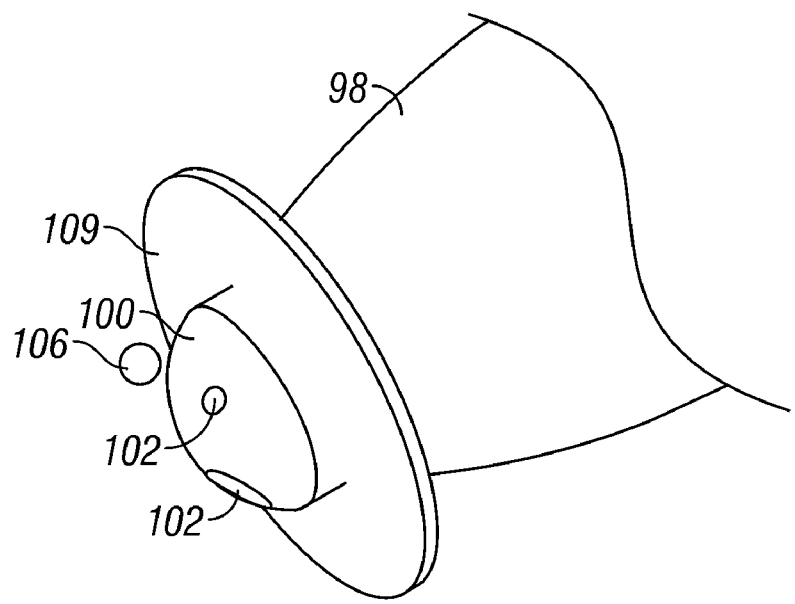
FIG. 5E is a perspective view of a portion of the stylus of FIG. 5A, showing the sensing region with a disposable film stretched and/or disposed thereon for receiving a biological sample.

FIGS. 5A to 5E illustrate another embodiment of an integrated receiver, wherein the single point glucose monitor includes a stylus movably mounted to the integrated receiver for measurement of glucose in a biological sample. FIG. 5A is a perspective view of the integrated receiver housing in another embodiment, showing a single point glucose monitor including a stylus movably mounted to the integrated receiver, wherein the stylus is shown in a storage position. FIG. 5B is a perspective view of the integrated housing of FIG. 5A, showing the stylus in a testing position. FIG. 5C is a perspective view of a portion of the stylus of FIG. 5A, showing the sensing region. FIG. 5D is a perspective view of the integrated receiver housing of FIG. 5A, showing the stylus loaded with a disposable film, and in its testing position. FIG. 5E is a perspective view of a portion of the stylus of FIG. 5A, showing the sensing region with a disposable film stretched and/or disposed thereon.

In this embodiment, the integrated receiver provides 92 a housing that integrates a single point glucose monitor 94 and electronics (see FIG. 8) useful to receive, process, and display data on the user interface 96. The single point glucose monitor 94 permits rapid and accurate measurement of the amount of a particular substance (for example, glucose) in a biological fluid. Generally, the integrated receiver electronics process single point glucose monitor data, receive and process continuous glucose sensor data, including calibration of the continuous sensor data using the single point monitor data for example, and output data via the user interface 96, such as is described below in more detail with reference to FIG. 8.

The single point glucose monitor 94 includes a stylus 98 that is movably mounted to the integrated receiver housing 92 via a connector 93. The connector 93 can be a cord, bar, hinge, or any such connection means that allows the stylus to move from a first (storage) position (FIG. 5A) to a second (testing) position (FIG. 5B) on the housing. The stylus is not constrained to the first and second positions; rather the stylus can be configured to swing at various angles, about various pivots, or in any manner allowed by the connector for convenience to the user. In some alternative embodiments, the stylus 98 is removably mounted on the integrated receiver housing 92 and an operable connection can be established using a wireless connection, or alternatively using electrical contacts that operably connect the stylus 98 that is removably mounted onto the integrated receiver housing 92.

The stylus 98 includes a sensing region 100 on one end that is operably connected to the integrated receiver's electronics (FIG. 8). As best illustrated in FIG. 5C, the sensing region 100 is provided with at least two, preferably three electrodes 102 and a sensing membrane (not shown) disposed over the electrodes 102 and/or the entire sensing region 100. The sensing region includes the electrodes 102 and the sensing membrane, which are configured to measure glucose in a manner such as described above with reference to the sensing region of FIGS. 2 and 4. In one embodiment, the sensing membrane is reusable and can be held on the sensing region 100 by a clip, such as described with reference to FIG. 2. In alternative embodiments, the sensing membrane is reusable can be disposed onto the sensing region using depositing or bonding techniques known in the art of polymers.

In order to maintain a preferred wetness of the sensing region 100, and particularly of the sensing membrane, the integrated receiver housing 92 includes a sterile solution chamber (not shown) located at the end of the receiving chamber 104 that receives the stylus for storage, such that when the stylus is in its storage position (FIG. 5A), the sensing membrane is maintained in the sterile solution. A sterile solution port 106 is in communication with the sterile solution chamber and allows for refilling of the sterile solution chamber using a sterile refill solution 108.

Typically, when a biological sample 106 (FIG. 5E) is placed on a surface, such as the surface of the sensing membrane and/or sensing region 100, there is a concern about contamination of the surface after use of the biological sample 106. Therefore, a single-use disposable bioprotective film 109 can be placed over the sensing region 100 to provide protection from contamination. The disposable film 109 can be any film with that allows the passage of glucose, but blocks the passage of undesired species in the blood that could damage or contaminate the sensing membrane and/or cause inaccurate measurements (for example, a thin film of very low molecular weight cutoff to prevent the transport of proteins, viruses, etc).

In some alternative embodiments, the bioprotective film 109 further comprises a sensing membrane formed as a part of the film (for example, laminated to the film), instead of (or in addition to) a sensing membrane disposed on the sensing region. This alternative embodiment is particularly advantageous in that it provides a disposable sensing membrane that requires no cleaning step, for example.

Because the stylus 98 can be put into direct contact with the biological sample 106 (for example, on a finger or arm), no transfer mechanism is required, and therefore the sample size can be smaller than conventionally required. Additionally, sensing region 100 does not require a separate cleaning step, because the disposable film 109 fully protects the sensing region 100 from contamination, and should be disposed of after use.

The integrated receiver 92 housing further allows for storage and dispensing of the disposable films 109. A shuttle mechanism 110 is provided that preferably feeds the films 109 into a spring-loaded storage chamber (not shown) beneath the shuttle mechanism 110, or the like. The shuttle mechanism 110 can be used to load the disposable films 109, one at a time, into a dispensing chamber 111 for dispensing onto the sensing region. In alternative embodiments, other storage and dispensing mechanisms can be configured as a part of the integrated receiver housing 12 or separate therefrom.

In practice, the stylus 98 is held in its storage position within the receiving chamber 104 where it is protected and maintained with a preferred wetness (FIG. 5A). A user then withdrawals the stylus 98 from the receiving chamber 104 (FIG. 5B) and loads a disposable film 109 by sliding the shuttle mechanism 110 toward the dispensing chamber 111. When the sensing region 100 of the stylus 98 presses on the disposable film 109 within the dispensing chamber, the film will be stretched over and/or otherwise stick to the moist sensing membrane on the surface of the sensing region 100 (FIG. 5D). At this point, the stylus 98 is ready for a biological sample (for example, blood sample) 106. The stylus 98 can be brought into contact with the finger or arm of the user to directly receive the biological sample from the user without the need for a transfer mechanism (FIG. 5E). After the test, the disposable film is removed from the sensing region and the stylus 98 is replaced into the receiving chamber 104 of the integrated receiver 92.

In this embodiment, the sensing region measures the glucose concentration of the biological sample in a manner such as described with reference to FIGS. 2 and 4, above. The integrated receiver's electronics, including data processing and calibration, are described in more detail below with reference to FIG. 8.

Figure 6A:
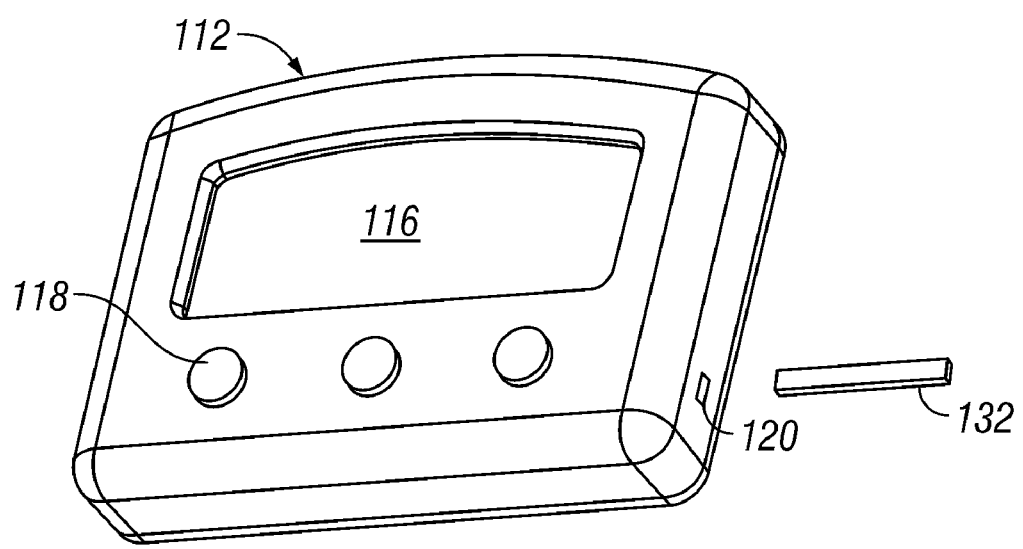
FIG. 6A is a perspective view of an integrated receiver in yet another embodiment, including a single point glucose monitor and a disposable capillary tube for transferring a biological sample to a sensing region on the monitor.
Figure 6B:
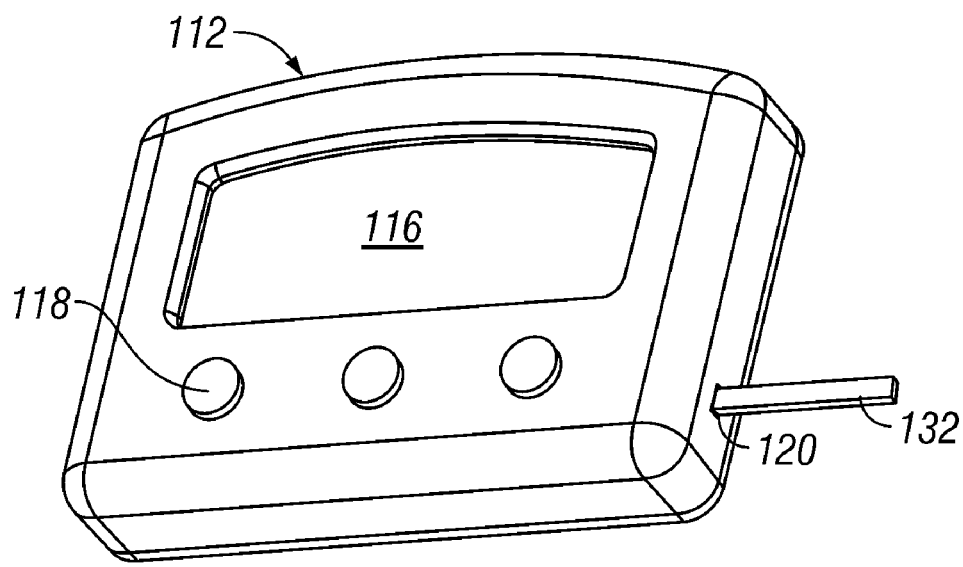
FIG. 6B is a perspective view of the integrated receiver of FIG. 6A, showing the disposable capillary tube inserted into the single point glucose monitor to transfer the biological sample to a sensing region on the single point glucose monitor.
Figure 6C:
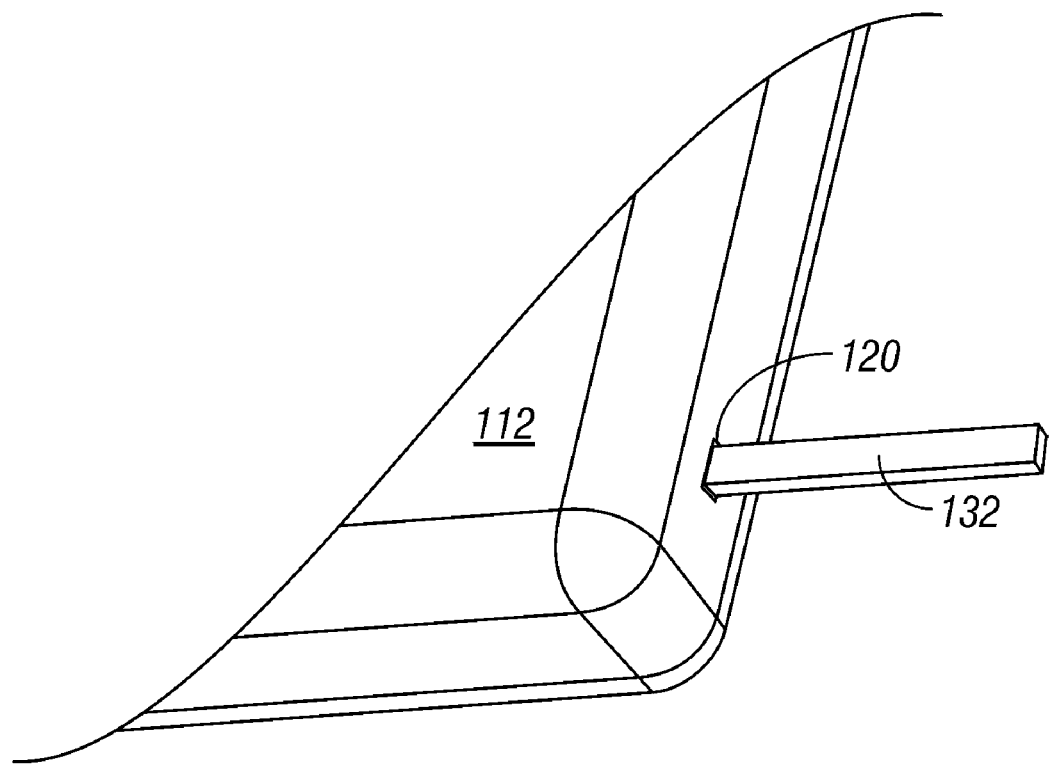
FIG. 6C is an expanded perspective view of a portion of the integrated receiver of FIG. 6A, showing the capillary tube inserted into the single point glucose monitor.
Figure 6D:
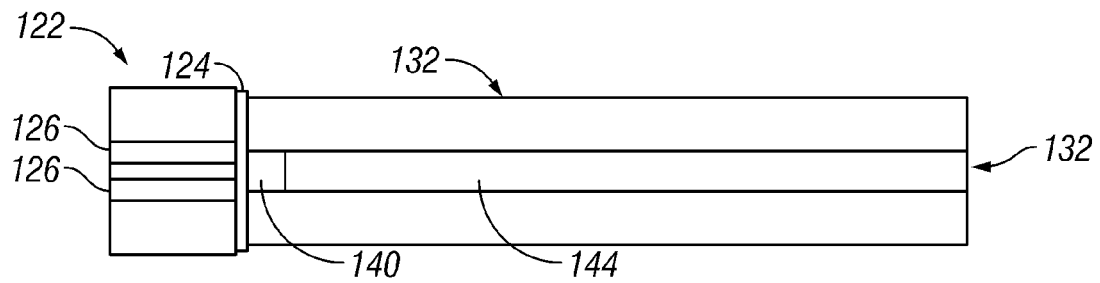
FIG. 6D is a schematic cross-sectional view of a capillary tube and a portion of the integrated receiver of FIG. 6A, illustrating the capillary tube in contact with the sensing membrane such that glucose from the biological sample can be measured by electrodes on the sensing region.
Figure 6E:
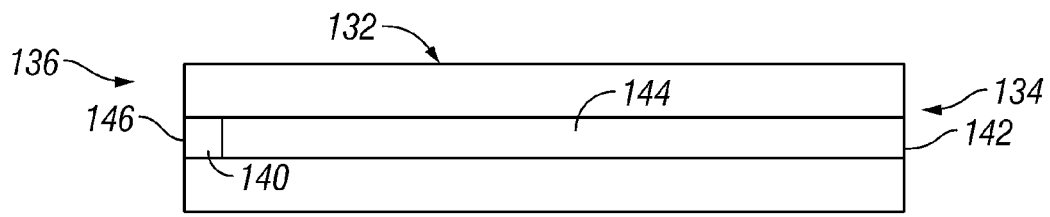
FIG. 6E is a schematic cross-sectional view of the capillary tube of FIG. 6A, illustrating an embodiment wherein a filter is located on one end.
Figure 6F:
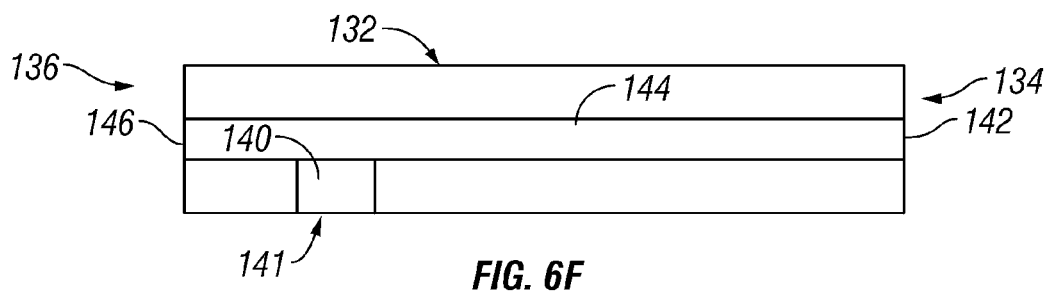
FIG. 6F is a schematic cross-sectional view of the capillary tube of FIG. 6A, illustrating an embodiment wherein a filter is disposed within a wall of the capillary tube.
Figure 6G:
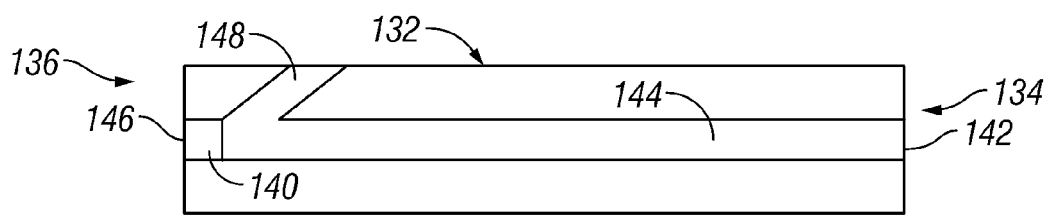
FIG. 6G is a schematic cross-sectional view of the capillary tube of FIG. 6A, illustrating an embodiment wherein a vent extends from the capillary tube.
Figure 6H:
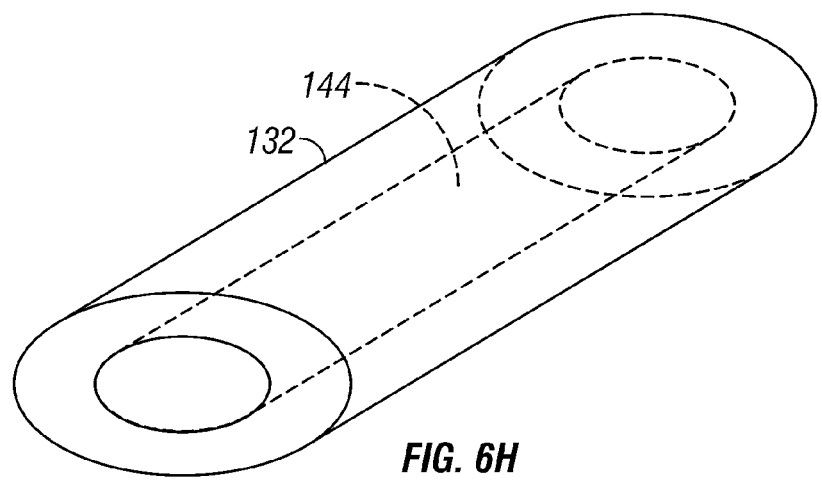
FIG. 6H is a schematic illustration of one embodiment, wherein the capillary tube is round in shape with an inner capillary tube that is also round in shape.
Figure 6I:
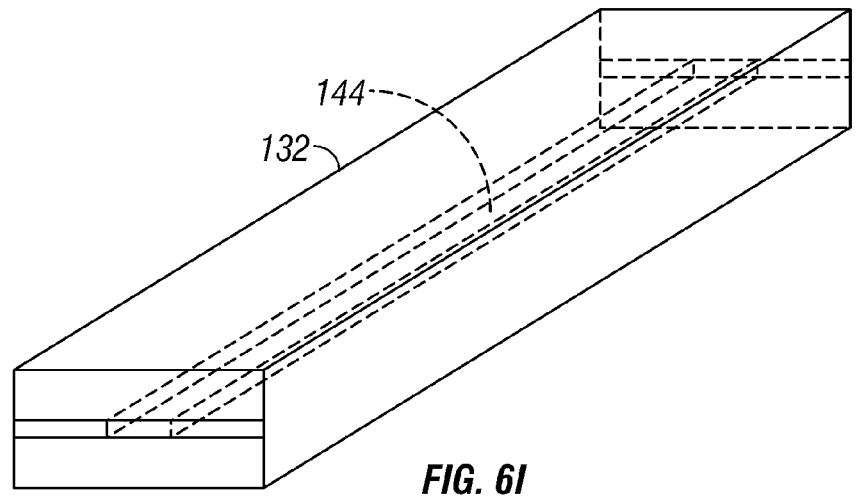
FIG. 6I is a schematic illustration of one embodiment, wherein the capillary tube is rectangular in shape with an inner capillary tube that is formed therein.
Figure 6J:
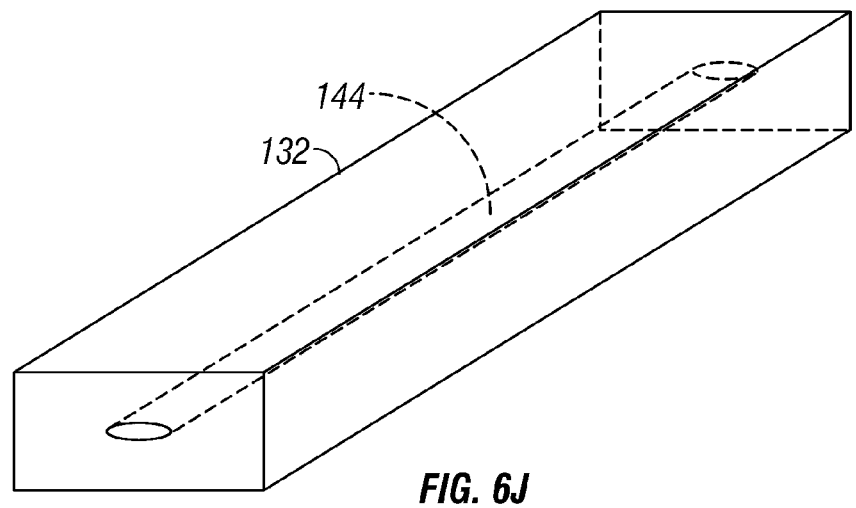
FIG. 6J is a schematic illustration of one embodiment, wherein the capillary tube is rectangular in shape an inner capillary tube has a rounded structure.

FIGS. 6A to 6J illustrate yet another embodiment of an integrated receiver, including a single point glucose monitor, electronics, and a disposable filtering capillary tube. FIG. 6A is a perspective view of the integrated receiver in yet another embodiment, including a single point glucose monitor and a disposable capillary tube for transferring a biological sample to a sensing region on the monitor. FIG. 6B is a perspective view of the integrated receiver of FIG. 6A, showing the disposable capillary tube inserted into the single point glucose monitor to transfer the biological sample to a sensing region on the single point glucose monitor. FIG. 6C is an expanded perspective view of a portion of the integrated receiver of FIG. 6A, showing the capillary tube inserted into the single point glucose monitor. FIG. 6D is a schematic cross-sectional view of a portion of the integrated receiver of FIG. 6A, illustrating the capillary tube in contact with a sensing membrane such that glucose from the biological sample can be measured by electrodes on the sensing region. FIG. 6E is a schematic cross-sectional view of the capillary tube of FIG. 6A, illustrating an embodiment wherein a filter is located on one end. FIG. 6F is a schematic cross-sectional view of the capillary tube of FIG. 6A, illustrating an embodiment wherein a filter is disposed between two ends. FIG. 6G is a schematic cross-sectional view of the capillary tube of FIG. 6A, illustrating an embodiment wherein a vent extends from the capillary tube. FIG. 6H is a schematic illustration of one embodiment, wherein the capillary tube 132 is round in shape with an inner capillary tube that is also round in shape. FIG. 6I is a schematic illustration of one embodiment, wherein the capillary tube 132 is rectangular in shape with an inner capillary tube 144 that is formed therein. FIG. 6J is a schematic illustration of one embodiment, wherein the capillary tube 132 is rectangular in shape an inner capillary tube 144 has a rounded structure.

In this embodiment, the integrated receiver provides a housing 112 that integrates a single point glucose monitor 114 and electronics (see FIG. 8) useful to receive, process, and display data on a user interface 116. The single point glucose monitor 114 permits rapid and accurate measurement of the amount of a particular substance (for example, glucose) in a biological sample. Generally, the electronics that process single point glucose monitor data, receive and process continuous glucose sensor data, including calibration of the continuous sensor data using the single point monitor data for example, and output data via the user interface 116, are described below in more detail with reference to FIG. 8. Buttons 118 can be provided on this or any of the preferred integrated receiver embodiments in order to facilitate user interaction with the integrated receiver.

The single point glucose monitor 114 includes a sensor port 120 configured to receive a biological fluid and measure its glucose concentration therefrom. As best illustrated in FIG. 6D, a sensing region 122, which includes a sensing membrane 124 (such as described in more detail elsewhere herein), is located within the sensor port 120. The sensing region includes electrodes 126, the top ends of which are in contact with an electrolyte phase (not shown), which is a free-flowing fluid phase disposed between the sensing membrane 124 and the electrodes 126. The sensing region 122 measures glucose in the biological sample in a manner such as described in more detail above, with reference to the sensing regions of FIGS. 2, 4, and 5. In some embodiments, the sensor port 120 includes a cover (not shown) configured to cover the sensing membrane 124 when the single glucose monitor is not in use in order to maintain a preferred wetness of the sensing region 122, and particularly of the sensing membrane.

Typically, when a biological sample is placed in on a surface (e.g., the sensing membrane 124), there is a concern about contamination of the surface from the biological sample. Therefore, a single-use disposable capillary tube 132 can be provided to transport and filter the biological sample, for example from a blood sample of a finger or arm, to the sensing region 122. The disposable capillary tube 132 uses capillary action to draw the biological sample from a first end 134 to a second end 136 of the capillary tube 132. A filter 140 is provided within the capillary tube 132, which is designed to allow the passage of glucose, but filter or block the passage of undesired species in the biological sample that could damage or contaminate the sensing membrane and/or cause inaccurate measurements (for example, the filter can be formed from a membrane of very low molecular weight cutoff to prevent the transport of proteins, viruses, etc). Because the filter 140 protects the sensing region 122 from contamination, the sensing region does not require a separate cleaning step, and the filter should be disposed of after use.

Referring now to FIGS. 6E to 6G, various embodiments of the filter within the capillary tube are illustrated. Each capillary tube 132 has a capillary inlet 142 at a first end 134, an inner capillary tube 144, a filter 140, and an outlet 146 on the second end 136. The capillary tube 132 enables the transport of blood or other aqueous solutions from the capillary inlet 142 to the capillary outlet 146. The fluid transport is facilitated by capillary action and preferably enabled by a hydrophilic surface of the inner capillary tube 144. In some embodiments, some portions of the inner capillary tube 144 can be made hydrophobic to control fluid flow. In some embodiments, the inner capillary tube 144 has a volume between about 2 and 3 microliters; however a larger or smaller volume is possible.

FIG. 6E is a schematic cross-sectional view of the capillary tube in one embodiment, wherein a filter 140 is disposed at the second end 136 within the inner capillary tube 144. This embodiment of the capillary tube is designed to filter the biological sample prior to its exit out of the capillary tube outlet 146.

FIG. 6F is a schematic cross-sectional view of the capillary tube in another embodiment, wherein the filter 140 within the wall capillary tube 132 rather than within the inner capillary tube 144. In this embodiment, the open inner capillary tube is designed to ensure accurate and repeatable fluid flow through the capillary tube by allowing displaced air to escape from the capillary tube outlet 146. As the fluid passes through the inner capillary tube 144, at least a portion of the bodily fluid flows down through the filter 140 and exits the capillary tube 132 through a side exit 141. In some embodiments, the surface of the inner capillary tube 144 near the second end of the capillary can be altered to be hydrophobic thereby preventing blood from escaping the second end.

FIG. 6G is a schematic cross-sectional view of the capillary tube in yet another embodiment, wherein the capillary tube further comprises a vent 148. This embodiment of the capillary tube is designed to ensure accurate and repeatable fluid flow through the capillary tube, by allowing displaced air and other gases to escape from the vent 148, which is located on a side of the capillary tube at a position the allows air to escape prior to filtering of the biological fluid through the filter 140.

Referring now to FIGS. 6H to 6J, various embodiments of the capillary tube structure are illustrated. The schematic views are intended to be exemplary and do not represent scale or proportion of the capillary tubes.

FIG. 6H is a schematic illustration of one embodiment, wherein the capillary tube 132 is round in shape with an inner capillary tube that is also round in shape. This is an embodiment similar to that shown in FIG. 6A to 6D, and optionally includes a tab, wings, or other structure to aid in handling and/or mechanical alignment of the tube 132.

FIG. 6I is a schematic illustration of one embodiment, wherein the capillary tube 132 is rectangular in shape with an inner capillary tube 144 that is formed therein. In one embodiment, the inner capillary tube 144 can be formed by methods, for example as known in the art of manufacturing test strips used for self-monitoring blood glucose meters.

FIG. 6J is a schematic illustration of one embodiment; wherein the capillary tube 132 is rectangular in shape an inner capillary tube 144 has a rounded structure. Shape, dimensions, proportions, or the like do not limit the capillary tube of the preferred embodiments, provided that the capillary tube is capable of performing capillary action.

The capillary tubes 132 can be manufactured using materials such as plastic, glass, silicon, or the like. In one embodiment, the preferred manufacturing material is plastic because of its low cost and the availability of numerous manufacturing processes. The inner capillary tube 144 can be molded or embossed to form the capillary structure. In some alternative embodiments, such as shown FIG. 6I, the inner capillary tube 144 can be formed by multi-layers including a top-capping layer that forms the capillary structure. Adhesive, ultrasonic bonding, solvents or other methods can be used to bond the layers. Holding tabs are not employed in certain embodiments of the capillary tube depending on their structure, for example the capillary tubes shown in FIGS. 6H to 6J.

In some embodiments, it can be advantageous to place a means of detecting a proper fill of the capillary. This can be accomplished for example by electrical means, optical means, or the like. In some embodiments (not shown), the integrated receiver housing 112 can be designed with a means for storing and dispensing capillary tubes 132. In alternative embodiments, other storage and/or dispensing means can be configured separate from the integrated receiver housing 112.

In practice, a user obtains a biological sample from a source, such as a finger or forearm (in some alternative embodiments, the single point glucose monitor can by designed to measure biological fluids other than blood, such as urine, sweat, or the like). The user then grasps a disposable capillary tube 132 (e.g., tab or outer surface) and contacts the source with the capillary inlet 142. Because of the design of the inner capillary tube 144, capillary action causes the biological sample to be drawn towards the capillary outlet 146. The biological sample is filtered as it passes through the filter 140, which is permeable to glucose but impermeable to large molecules and species in the blood that can clog, damage, or contaminate the sensing membrane 124, and/or cause inaccurate measurements. Therefore, the biological sample permeates the filter 140 and into the sensing membrane 124 (for example, fluid contact between the capillary tube and sensing membrane enables the transfer of the filtered biological sample), where it enyzmatically reacts with the catalyst (e.g., glucose oxidase) and produces hydrogen peroxide. Hydrogen peroxide is detected by the electrochemical sensor, wherein the electrical signal is converted into glucose value, such as described in more detail elsewhere herein.

The sensing membrane 124 is a reusable component of the single point glucose monitor, which advantageously provides a low cost associated with each glucose measurement as compared to conventional glucose measuring test strips. Additionally, the disposable capillary tube 132 simplifies the cleanup of the device, as compared to conventional single point glucose monitors that utilize similar enzyme membrane technology. Furthermore, because the blood remains within the capillary tube 144, which can be disposed of without contaminating the integrated receiver housing 112 or the sensing membrane 124, the risk of human contact with blood is reduced.

Figure 7A:
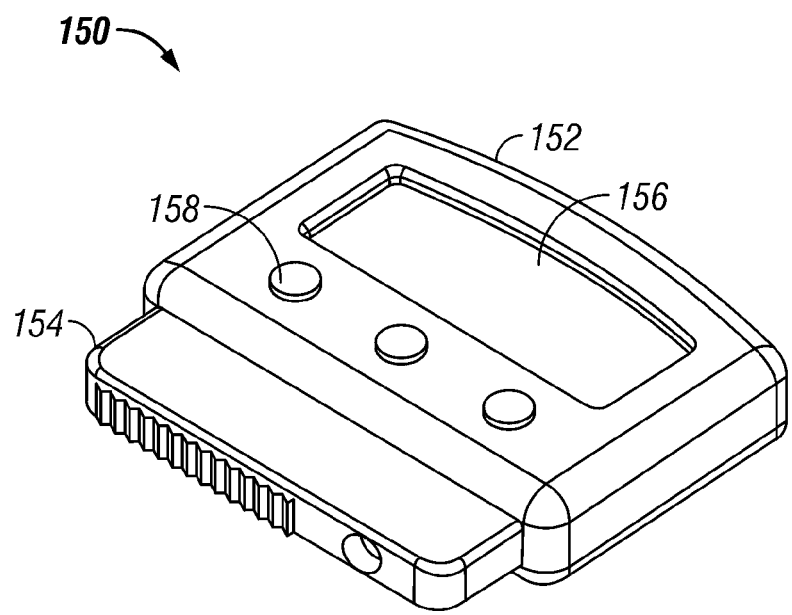
FIG. 7A is a perspective view of an integrated receiver in yet another embodiment, wherein the single point glucose monitor is detachably connected to the receiver to form a modular configuration, shown in its attached state.
Figure 7B:
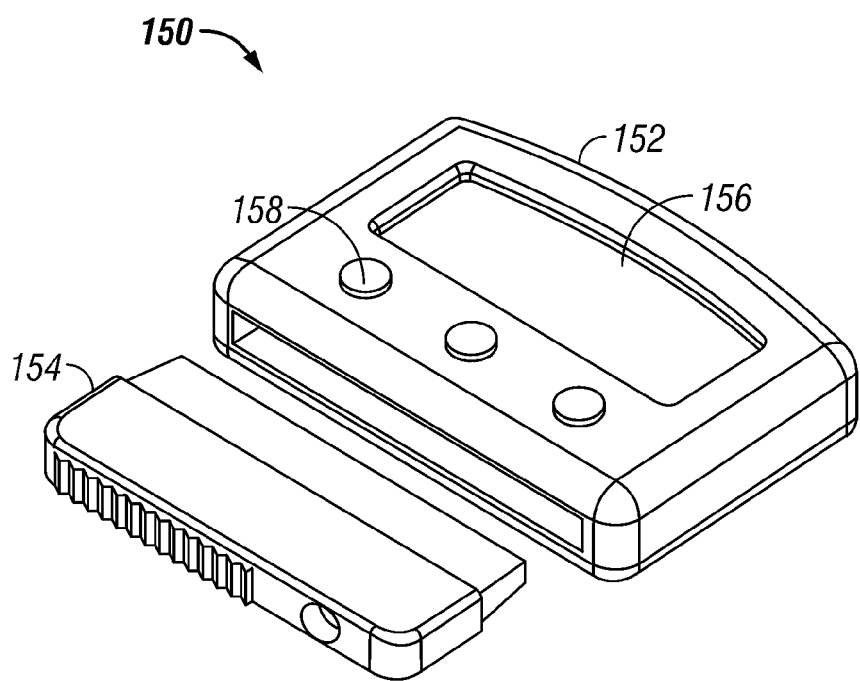
FIG. 7B is a perspective view of the integrated receiver of FIG. 7A, shown in its detached state.

FIGS. 7A and 7B are perspective views of yet another embodiment of an integrated receiver, wherein the single point glucose monitor is detachably connected to the receiver housing to provide a modular configuration. FIG. 7A is a perspective view of the integrated receiver in this embodiment, wherein the single point glucose monitor is detachably connected to the receiver to form a modular configuration, shown in its connected state. FIG. 7B is a perspective view of the integrated receiver of FIG. 7A, shown in its detached state.

In this embodiment, the integrated receiver 150 provides a receiver housing 152 and a single point glucose monitor 154, which are detachably connectable to each other. The receiver housing 152 includes electronics (hardware and software) useful to receive, process, and display data from the continuous glucose sensor and/or the single point glucose sensor on a user interface 156, such as described in more detail with reference to FIG. 8. In some embodiments, some part of the electronics (for example, the electronics specific to the single point glucose monitor 154) can be housed within the single point glucose monitor 154. The single point glucose monitor 154 can be configured as described with reference to FIG. 6, for example, to permit rapid and accurate measurements of the amount of a particular substance (for example, glucose) in a biological sample. In alternative embodiments, the single point glucose monitor of this modular embodiment can be configured as described with reference to any of the single point glucose monitors of the preferred embodiments. In yet alternative embodiments, the single point glucose monitor can be configured using other known glucose meter configurations.

In general, this embodiment provides for a modular configuration between a receiver housing 152 and a single point glucose monitor 154, wherein the single point glucose monitor can be detached when a user prefers to carry a smaller, simpler, or lighter device (for example, during exercise). However, when a user is ready to perform a single point glucose test, the glucose monitor 154 can be easily attached to the receiver 152 to form an integrated receiver 150 with its numerous associated advantages. In one embodiment, electrical contacts (not shown) on the receiver housing 152 and the single point glucose monitor 154 allow an electrical connection to be established in its attached position. In another embodiment, a wireless connection between the receiver housing 152 and the single point glucose monitor 154 can be provided, wherein the integration is advantageous for its convenient one-piece system (for example, fewer loose parts), its similar measurement technologies (for example, enzyme membrane-based electrochemical measurement), and its added versatility to function even when the modular device is detached.

While not required, it is preferred in this embodiment that the single point glucose monitor 154 be dependent upon the integrated receiver 152 for at least a portion of its operation. For example, at least some of the electronics and/or user interface for the single point glucose monitor 154 are located within the receiver 152. Numerous advantages associated with the integrated receiver 150, such as ensuring accurate time stamping of the single point glucose test at the receiver and other advantages described herein, can be provided by an integrated continuous glucose receiver and single point glucose monitor, such as described herein.

Additionally, the integrated receiver housing configurations of the preferred embodiments are advantageous in that they can be calibrated by the user and can be designed with a measurement technique consistent with that of the continuous glucose sensor. These and other advantages can be seen in alternative embodiments of the device of the preferred embodiments, which are described in more detail elsewhere herein.

In one alternative embodiment, the single point glucose monitor comprises an integrated lancing and measurement device such as described in U.S. Pat. No. 6,607,658 to Heller et al. In another alternative embodiment, the single point glucose monitor comprises a near infrared device such as described in U.S. Pat. No. 5,068,536 to Rosenthal et al. In another alternative embodiment, the single point glucose monitor comprises an integrated lancer, blood-monitoring device, and medication delivery pen, such as described in U.S. Pat. No. 6,192,891 to Gravel et al. In another alternative embodiment, the single point glucose monitor comprises a reflectance reading apparatus such as described in U.S. Pat. No. 5,426,032 to Phillips et al. In another alternative embodiment, the single point glucose monitor comprises a spectroscopic transflectance device such as described in U.S. Pat. No. 6,309,884 to Cooper et al. Other integrations that can be combined with the integrated receiver are described in co-pending U.S. patent application Ser. No. 10/789,359, filed Feb. 26, 2004. All of the above patents and patent applications are incorporated in their entirety herein by reference.

FIG. 8 is a block diagram that illustrates integrated receiver electronics in one embodiment. The described electronics are applicable to the preferred embodiments, including the integrated receiver 12 of FIGS. 1, 4A, and 4B, the integrated receiver 92 of FIGS. 5A to 5E, the integrated receiver 112 of FIGS. 6A to 6D, and the integrated receiver 150 of FIGS. 7A and 7B.

A quartz crystal 160 is operably connected to an RF transceiver 162, which together function to receive and synchronize data streams 164 via an antenna 166 (for example, transmission 46 from the RF transceiver 44 shown in FIG. 3). Once received, a microprocessor 168 processes the signals, such as described below.

The microprocessor 168 is the central control unit that provides the processing, such as storing data, analyzing continuous glucose sensor data stream, analyzing single point glucose values, accuracy checking, checking clinical acceptability, calibrating sensor data, downloading data, and controlling the user interface by providing prompts, messages, warnings and alarms, or the like. The EEPROM 170 is operably connected to the microprocessor 168 and provides semi-permanent storage of data, storing data such as receiver ID and programming to process data streams (for example, programming for performing calibration and other algorithms described elsewhere herein). SRAM 172 is used for the system's cache memory and is helpful in data processing. For example, the SRAM stores information from the continuous glucose sensor and the single point glucose monitor for later recall by the user or a doctor; a user or doctor can transcribe the stored information at a later time to determine compliance with the medical regimen or a comparison of glucose concentration to medication administration (for example, this can be accomplished by downloading the information through the pc corn port 174). In addition, the SRAM 172 can also store updated program instructions and/or patient specific information. FIGS. 9 and 10 describe more detail about programming that is preferably processed by the microprocessor 168. In some alternative embodiments, memory storage components comparable to EEPROM and SRAM can be used instead of or in addition to the preferred hardware, such as dynamic RAM, non-static RAM, rewritable ROMs, flash memory, or the like.

A battery 176 is operably connected to the microprocessor 168 and provides power for the receiver. In one embodiment, the battery is a standard AAA alkaline battery, however any appropriately sized and powered battery can be used. In some embodiments, a plurality of batteries can be used to power the system. In some embodiments, a power port (not shown) is provided permit recharging of rechargeable batteries. A quartz crystal 178 is operably connected to the microprocessor 168 and maintains system time for the computer system as a whole.

A PC communication (com) port 174 can be provided to enable communication with systems, for example, a serial communications port, allows for communicating with another computer system (for example, PC, PDA, server, or the like). In one exemplary embodiment, the receiver is able to download historical data to a physician's PC for retrospective analysis by the physician. The PC communication port 174 can also be used to interface with other medical devices, for example pacemakers, implanted analyte sensor patches, infusion devices, telemetry devices, or the like.

Electronics associated with the single point glucose monitor 180 are operably connected to the microprocessor 168 and include a potentiostat 181 in one embodiment that measures a current flow produced at the working electrode when a biological sample is placed on the sensing membrane, such as described with reference to FIGS. 4 to 7, for example. The current is then converted into an analog signal by a current to voltage converter, which can be inverted, level-shifted, and sent to the A/D converter 182. The microprocessor can set the analog gain via its control port (not shown). The A/D converter is preferably activated at one-second intervals. The microprocessor looks at the converter output with any number of pattern recognition algorithms known to those skilled in the art until a glucose peak is identified. A timer is then preferably activated for about 30 seconds at the end of which time the difference between the first and last electrode current values is calculated. This difference is then divided by the value stored in the memory during instrument calibration and is then multiplied by the calibration glucose concentration. The glucose value in milligram per deciliter, millimoles per liter, or the like, is then stored in the microprocessor, displayed on the user interface, used to calibrate of the glucose sensor data stream, downloaded, etc.

A user interface 184 comprises a keyboard 186, speaker 188, vibrator 190, backlight 192, liquid crystal display (LCD) 194, and one or more buttons 196. The components that comprise the user interface 184 provide controls to interact with the user. The keyboard 186 can allow, for example, input of user information about an individual, such as mealtime, exercise, insulin administration, and reference glucose values. The speaker 188 can provide, for example, audible signals or alerts for conditions such as present and/or predicted hyper- and hypoglycemic conditions. The vibrator 190 can provide, for example, tactile signals or alerts for reasons such as described with reference to the speaker, above. The backlight 192 can be provided, for example, to aid the user in reading the LCD in low light conditions. The LCD 194 can be provided, for example, to provide the user with visual data output. In some embodiments, the LCD is a touch-activated screen. The buttons 196 can provide for toggle, menu selection, option selection, mode selection, and reset, for example. In some alternative embodiments, a microphone can be provided to allow for voice-activated control.

The user interface 184, which is operably connected to the microprocessor 168 serves to provide data input and output for both the continuous glucose sensor (for example, FIGS. 2 and 3) and for the integrated receiver including the single point glucose monitor (for example, FIGS. 4 to 7).

In some embodiments, prompts or messages can be displayed on the user interface to guide the user through the initial calibration and sample measurement procedures for the single point glucose monitor. Additionally, prompts can be displayed to inform the user about necessary maintenance procedures, such as "Replace Sensing Membrane" or "Replace Battery." Even more, the glucose concentration value measured from the single point glucose monitor can be individually displayed.

In some embodiments, prompts or messages can be displayed on the user interface to convey information to the user, such as malfunction, outlier values, missed data transmissions, or the like, for the continuous glucose sensor. Additionally, prompts can be displayed to guide the user through calibration of the continuous glucose sensor. Even more, calibrated sensor glucose data, which is described in more detail with reference to FIGS. 9 and 10, can be displayed in numerical or graphical representations, or the like.

Reference is now made to FIG. 9, which is a flow chart that illustrates the process of initial calibration and data output of the glucose sensor 10 in one embodiment. Calibration of the glucose sensor 10 generally includes data processing that converts a sensor data stream into estimated glucose values that are meaningful to a user. Accordingly, a reference glucose value can be used to calibrate the data stream from the glucose sensor 10. The calibration can be performed on a real-time basis and/or backwards recalibrated (for example, retrospectively).

At block 200, a sensor data receiving module, also referred to as the sensor data module, receives sensor data (for example, a data stream), including one or more time-spaced sensor data points, hereinafter referred to as "sensor data" or "sensor glucose data." The integrated receiver receives the sensor data from a continuous glucose sensor, which can be in wired or wireless communication with the integrated receiver. Some or all of the sensor data point(s) can be smoothed or replaced by estimated signal values such as described with reference to co-pending U.S. patent application entitled, "SYSTEMS AND METHODS FOR REPLACING SIGNAL ARTIFACTS IN A GLUCOSE SENSOR DATA STREAM," filed Aug. 22, 2003. During the initialization of the sensor, prior to initial calibration, the integrated receiver (for example, FIGS. 4 to 7) receives and stores the sensor data, however it does not necessarily display any data to the user until initial calibration and optionally stabilization of the sensor 10 has been determined.

At block 202 a single point glucose module, also referred to as the reference input module, receives glucose data from the integrated single point glucose monitor, including one or more reference glucose data points, hereinafter referred as "reference data" or "reference glucose data." Namely, the single point glucose monitor, such as described in more detail with reference to FIGS. 4 to 7, which is integral with the receiver, provides a reference glucose concentration value, such as described above with respect to the single point glucose monitors of the preferred embodiments. The reference glucose concentration value from the single point glucose monitor is calibrated such as described above in more detail with reference to FIG. 8.

In some embodiments, the microprocessor 168 monitors the continuous glucose sensor data stream to determine a preferable time for capturing glucose concentration values using the single point glucose monitor electronics 180 for calibration of the continuous sensor data stream. For example, when sensor glucose data (for example, observed from the data stream) changes too rapidly, a single point glucose monitor reading may not be sufficiently reliable for calibration during unstable glucose changes in the host; in contrast, when sensor glucose data are relatively stable (for example, relatively low rate of change), a single point glucose monitor reading can be taken for a reliable calibration. In some additional embodiments, the microprocessor can prompt the user via the user interface to obtain a single point glucose value for calibration at predetermined intervals. In some additional embodiments, the user interface can prompt the user to obtain a single point glucose monitor value for calibration based upon certain events, such as meals, exercise, large excursions in glucose levels, faulty or interrupted data readings, or the like. In some embodiments, certain acceptability parameters can be set for reference values received from the single point glucose monitor. For example, in one embodiment, the receiver only accepts reference glucose data between about 40 and about 400 mg/dL.

At block 204, a data matching module, matches reference data (for example, one or more reference glucose data points) with substantially time corresponding sensor data (for example, one or more sensor data points) to provide one or more matched data pairs. In one embodiment, one reference data point is matched to one time corresponding sensor data point to form a matched data pair. In another embodiment, a plurality of reference data points are averaged (for example, equally or non-equally weighted average, mean-value, median, or the like) and matched to one time corresponding sensor data point to form a matched data pair. In another embodiment, one reference data point is matched to a plurality of time corresponding sensor data points averaged to form a matched data pair. In yet another embodiment, a plurality of reference data points are averaged and matched to a plurality of time corresponding sensor data points averaged to form a matched data pair.

In one embodiment, time corresponding sensor data comprises one or more sensor data points that occur, for example, 15±5 min after the reference glucose data timestamp (for example, the time that the reference glucose data is obtained). In this embodiment, the 15 minute time delay has been chosen to account for an approximately 10 minute delay introduced by the filter used in data smoothing and an approximately 5 minute physiological time-lag (for example, the time necessary for the glucose to diffusion through a membrane(s) of a glucose sensor). In alternative embodiments, the time corresponding sensor value can be more or less than in the above-described embodiment, for example ±60 minutes. Variability in time correspondence of sensor and reference data can be attributed to, for example, a longer or shorter time delay introduced during signal estimation, or if the configuration of the glucose sensor 10 incurs a greater or lesser physiological time lag.

One advantage of integrated receiver of the preferred embodiments can be seen in the time stamp of the reference glucose data. Namely, typical implementations of the continuous glucose sensor 10, wherein the single point glucose monitor is not integral with the receiver, the reference glucose data can be obtained at a time that is different from the time that the data is input into the receiver 30. Thus, the user may not accurately input the "time stamp" of the reference glucose (for example, the time at which the reference glucose value was actually obtained) at the time of reference data input into the receiver. Therefore, the accuracy of the calibration is subject to human error (for example, due to inconsistencies in entering the actual time of the single point glucose test). In contrast, the preferred embodiments of the integrated receiver advantageously do no suffer from this potential inaccuracy in that the time stamp is automatically and accurately obtained at the time of single point glucose test. Additionally, the process of obtaining reference data is simplified and made convenient using the integrated receiver because of fewer loose parts (for example, cables, test strips, or the like) and less required data entry (for example, time of testing).

In some embodiments, tests are used to evaluate the best-matched pair using a reference data point against individual sensor values over a predetermined time period (for example, about 30 minutes). In one such embodiment, the reference data point is matched with sensor data points at 5-minute intervals and each matched pair is evaluated. The matched pair with the best correlation can be selected as the matched pair for data processing. In some alternative embodiments, matching a reference data point with an average of a plurality of sensor data points over a predetermined time period can be used to form a matched pair.

At block 206, a calibration set module, forms an initial calibration set from a set of one or more matched data pairs, which are used to determine the relationship between the reference glucose data and the sensor glucose data, such as described in more detail with reference to block 208, below.

The matched data pairs, which make up the initial calibration set, can be selected according to predetermined criteria. In some embodiments, the number (n) of data pair(s) selected for the initial calibration set is one. In other embodiments, n data pairs are selected for the initial calibration set wherein n is a function of the frequency of the received reference glucose data points. In one exemplary embodiment, six data pairs make up the initial calibration set. In another embodiment, the calibration set includes only one data pair.

In some embodiments, the data pairs are selected only within a certain glucose value threshold, for example wherein the reference glucose value is between about 40 and about 400 mg/dL. In some embodiments, the data pairs that form the initial calibration set are selected according to their time stamp.

At block 208, a conversion function module creates a conversion function using the calibration set. The conversion function substantially defines the relationship between the reference glucose data and the sensor glucose data. A variety of known methods can be used with the preferred embodiments to create the conversion function from the calibration set. In one embodiment, wherein a plurality of matched data points form the initial calibration set, a linear least squares regression is performed on the initial calibration set such as described in more detail with reference to FIG. 10.

At block 210, a sensor data transformation module uses the conversion function to transform sensor data into substantially real-time glucose value estimates, also referred to as calibrated data, as sensor data is continuously (or intermittently) received from the sensor. In other words, the offset value at any given point in time can be subtracted from the raw value (for example, in counts) and divided by the slope to obtain the estimated glucose value:

$$mg/dL = \frac{(rawvalue - \text{offset})}{\text{slope}}$$

In some alternative embodiments, the sensor and/or reference glucose data are stored in a database for retrospective analysis.

At block 212, an output module provides output to the user via the user interface. The output is representative of the estimated glucose value, which is determined by converting the sensor data into a meaningful glucose value such as described in more detail with reference to block 210, above. User output can be in the form of a numeric estimated glucose value, an indication of directional trend of glucose concentration, and/or a graphical representation of the estimated glucose data over a period of time, for example. Other representations of the estimated glucose values are also possible, for example audio and tactile.

In one embodiment, the estimated glucose value is represented by a numeric value. In other exemplary embodiments, the user interface graphically represents the estimated glucose data trend over a predetermined time period (for example, one, three, and nine hours, respectively). In alternative embodiments, other time periods can be represented. In alternative embodiments, pictures, animation, charts, graphs, and numeric data can be selectively displayed.

Accordingly, after initial calibration of the sensor, real-time continuous glucose information can be displayed on the user interface so that the user can regularly and proactively care for his/her diabetic condition within the bounds set by his/her physician. Both the calibrated reference glucose data from the single point glucose monitor and the sensor glucose data from the continuous glucose sensor can be displayed to the user. In an embodiment wherein the continuous glucose sensor functions as an adjunctive device to the single point glucose monitor, the user interface can display numeric reference glucose data, while showing the sensor glucose data only in a graphical representation so that the user can see the historical and present sensor trend information as well as the most recent reference glucose data value. In an embodiment wherein the continuous glucose sensor functions as a non-adjunctive device to the single point glucose monitor, the user interface can display the reference glucose data and/or the sensor glucose data. The user can toggle through menus and screens using the buttons in order to view alternate data and/or screen formats, for example.

In alternative embodiments, the conversion function is used to predict glucose values at future points in time. These predicted values can be used to alert the user of upcoming hypoglycemic or hyperglycemic events. Additionally, predicted values can be used to compensate for the time lag (for example, 15 minute time lag such as described elsewhere herein), so that an estimated glucose value displayed to the user represents the instant time, rather than a time delayed estimated value.

In some embodiments, the substantially real-time estimated glucose value, a predicted future estimated glucose value, a rate of change, and/or a directional trend of the glucose concentration is used to control the administration of a constituent to the user, including an appropriate amount and time, in order to control an aspect of the user's biological system. One such example is a closed loop glucose sensor and insulin pump, wherein the glucose data (for example, estimated glucose value, rate of change, and/or directional trend) from the glucose sensor is used to determine the amount of insulin, and time of administration, that can be given to a diabetic user to evade hyper- and hypoglycemic conditions.

FIG. 10 is a graph that illustrates one embodiment of a regression performed on a calibration set to create a conversion function such as described with reference to FIG. 9, block 208, above. In this embodiment, a linear least squares regression is performed on the initial calibration set. The x-axis represents reference glucose data; the y-axis represents sensor data. The graph pictorially illustrates regression of matched pairs 214 in the calibration set. The regression calculates a slope 216 and an offset 218, for example, using the well-known slope-intercept equation ($y=mx+b$), which defines the conversion function.

In alternative embodiments, other algorithms could be used to determine the conversion function, for example forms of linear and non-linear regression, for example fuzzy logic, neural networks, piece-wise linear regression, polynomial fit, genetic algorithms, and other pattern recognition and signal estimation techniques.

In yet other alternative embodiments, the conversion function can comprise two or more different optimal conversions because an optimal conversion at any time is dependent on one or more parameters, such as time of day, calories consumed, exercise, or glucose concentration above or below a set threshold, for example. In one such exemplary embodiment, the conversion function is adapted for the estimated glucose concentration (for example, high vs. low). For example in an implantable glucose sensor it has been observed that the cells surrounding the implant will consume at least a small amount of glucose as it diffuses toward the glucose sensor. Assuming the cells consume substantially the same amount of glucose whether the glucose concentration is low or high, this phenomenon will have a greater effect on the concentration of glucose during low blood sugar episodes than the effect on the concentration of glucose during relatively higher blood sugar episodes. Accordingly, the conversion function can be adapted to compensate for the sensitivity differences in blood sugar level. In one implementation, the conversion function comprises two different regression lines, wherein a first regression line is applied when the estimated glucose concentration is at or below a certain threshold (for example, 150 mg/dL) and a second regression line is applied when the estimated glucose concentration is at or above a certain threshold (for example, 150 mg/dL). In one alternative implementation, a predetermined pivot of the regression line that forms the conversion function can be applied when the estimated blood is above or below a set threshold (for example, 150 mg/dL), wherein the pivot and threshold are determined from a retrospective analysis of the performance of a conversion function and its performance at a range of glucose concentrations. In another implementation, the regression line that forms the conversion function is pivoted about a point in order to comply with clinical acceptability standards (for example, Clarke Error Grid, Consensus Grid, mean absolute relative difference, or other clinical cost function) and/or physiological parameters. Although only a few example implementations are described, other embodiments include numerous implementations wherein the conversion function is adaptively applied based on one or more parameters that can affect the sensitivity of the sensor data over time.

The preferred embodiments described a continuous glucose sensor and integrated receiver with single point glucose calibration that is more cost effective than conventional reference glucose monitors (for example, more cost effective than test strips). Additionally, the consistency between the similar measurement technologies used both for the continuous sensor and the single point glucose monitor increases the consistency and decreases the cause for error between the two measurements devices, yielding a more reliable, accurate device.

In some alternative embodiments similarly advantageous results can be provided that by combined continuous glucose sensor and integrated receiver configurations wherein the measurement technologies are consistent between the continuous glucose sensor and single point glucose monitor. For example, an optical, non-invasive, "continuous or quasi-continuous" glucose measurement device such as described by U.S. Pat. No. 6,049,727, which is incorporated by reference herein in its entirety, can be implanted in the body. An integrated receiver can be provided that processes sensor data and includes an optical non-invasive single point glucose monitor such as described with reference to U.S. Pat. No. 6,309,884, which is incorporated by reference herein in its entirety. Accordingly, when optical-based technology is used both for the continuous sensor and the single point glucose monitor, increased consistency and decreased cause for error between the two measurements devices exist, yielding a more reliable, accurate device. Other embodiments can be provided that utilize consistent measurement technologies between a continuous analyte sensor and a single point analyte monitor useful for calibration such as described herein and are within the spirit of the preferred embodiments.

Methods and devices that are suitable for use in conjunction with aspects of the preferred embodiments are disclosed in co-pending U.S. patent application Ser. No. 10/885,476 filed Jul. 6, 2004, and entitled "SYSTEMS AND METHODS FOR MANUFACTURE OF AN ANALYTE-MEASURING DEVICE INCLUDING A MEMBRANE SYSTEM"; U.S. patent application Ser. No. 10/842,716, filed May 10, 2004, and entitled, "MEMBRANE SYSTEMS INCORPORATING BIOACTIVE AGENTS"; co-pending U.S. patent application Ser. No. 10/838,912 filed May 3, 2004, and entitled, "IMPLANTABLE ANALYTE SENSOR"; U.S. patent application Ser. No. 10/789,359 filed Feb. 26, 2004, and entitled, "INTEGRATED DELIVERY DEVICE FOR A CONTINUOUS GLUCOSE SENSOR"; U.S. application Ser. No. 10/685,636 filed Oct. 28, 2003, and entitled, "SILICONE COMPOSITION FOR MEMBRANE SYSTEM"; U.S. application Ser. No. 10/648,849 filed Aug. 22, 2003, and entitled, "SYSTEMS AND METHODS FOR REPLACING SIGNAL ARTIFACTS IN A GLUCOSE SENSOR DATA STREAM"; U.S. application Ser. No. 10/646,333 filed Aug. 22, 2003, entitled, "OPTIMIZED SENSOR GEOMETRY FOR AN IMPLANTABLE GLUCOSE SENSOR"; U.S. application Ser. No. 10/647,065 filed Aug. 22, 2003, entitled, "POROUS MEMBRANES FOR USE WITH IMPLANTABLE DEVICES"; U.S. application Ser. No. 10/633,367 filed Aug. 1, 2003, entitled, "SYSTEM AND METHODS FOR PROCESSING ANALYTE SENSOR DATE"; U.S. Pat. No. 6,702,857 entitled "MEMBRANE FOR USE WITH IMPLANTABLE DEVICES"; U.S. application Ser. No. 09/916,711 filed Jul. 27, 2001, and entitled "SENSOR HEAD FOR USE WITH IMPLANTABLE DEVICE"; U.S. application Ser. No. 09/447,227 filed Nov. 22, 1999, and entitled "DEVICE AND METHOD FOR DETERMINING ANALYTE LEVELS"; U.S. application Ser. No. 10/153,356 filed May 22, 2002, and entitled "TECHNIQUES TO IMPROVE POLYURETHANE MEMBRANES FOR IMPLANTABLE GLUCOSE SENSORS"; U.S. application Ser. No. 09/489,588 filed Jan. 21, 2000, and entitled "DEVICE AND METHOD FOR DETERMINING ANALYTE LEVELS"; U.S. application Ser. No. 09/636,369 filed Aug. 11, 2000, and entitled "SYSTEMS AND METHODS FOR REMOTE MONITORING AND MODULATION OF MEDICAL DEVICES"; and U.S. application Ser. No. 09/916,858 filed Jul. 27, 2001, and entitled "DEVICE AND METHOD FOR DETERMINING ANALYTE LEVELS," as well as issued patents including U.S. Pat. No. 6,001,067 issued Dec. 14, 1999, and entitled "DEVICE AND METHOD FOR DETERMINING ANALYTE LEVELS"; U.S. Pat. No. 4,994,167 issued Feb. 19, 1991, and entitled "BIOLOGICAL FLUID MEASURING DEVICE"; and U.S. Pat. No. 4,757,022 filed Jul. 12, 1988, and entitled "BIOLOGICAL FLUID MEASURING DEVICE"; U.S. Appl. No. 60/489,615 filed Jul. 23, 2003, and entitled "ROLLED ELECTRODE ARRAY AND ITS METHOD FOR MANUFACTURE"; U.S. Appl. No. 60/490,010 filed Jul. 25, 2003, and entitled "INCREASING BIAS FOR OXYGEN PRODUCTION IN AN ELECTRODE ASSEMBLY"; U.S. Appl. No. 60/490,009 filed Jul. 25, 2003, and entitled "OXYGEN ENHANCING ENZYME MEMBRANE FOR ELECTROCHEMICAL SENSORS"; U.S. application Ser. No. 10/896,312 filed Jul. 21, 2004, and entitled "OXYGEN-GENERATING ELECTRODE FOR USE IN ELECTROCHEMICAL SENSORS"; U.S. application Ser. No. 10/896,637 filed Jul. 21, 2004, and entitled "ROLLED ELECTRODE ARRAY AND ITS METHOD FOR MANUFACTURE"; U.S. application Ser. No. 10/896,772 filed Jul. 21, 2004, and entitled "INCREASING BIAS FOR OXYGEN PRODUCTION IN AN ELECTRODE ASSEMBLY"; U.S. application Ser. No. 10/896,639 filed Jul. 21, 2004, and entitled "OXYGEN ENHANCING ENZYME MEMBRANE FOR ELECTROCHEMICAL SENSORS"; U.S. application Ser. No. 10/897,377 filed Jul. 21, 2004, and entitled "ELECTROCHEMICAL SENSORS INCLUDING ELECTRODE SYSTEMS WITH INCREASED OXYGEN GENERATION". The foregoing patent applications and patents are incorporated herein by reference in their entireties.

All references cited herein are incorporated herein by reference in their entireties. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A system for monitoring a glucose concentration in a biological sample in a host, the system comprising:
a continuous glucose sensor configured to produce sensor data indicative of a glucose concentration in a host, wherein the glucose sensor comprises a sensing membrane comprising an enzyme domain; and
a receiver unit adapted to receive the sensor data from the continuous glucose sensor, wherein the receiver unit comprises a housing, and wherein the receiver unit comprises:
a single point glucose monitor physically connected to the housing, wherein the single point glucose monitor is configured to produce a glucose concentration measurement from a biological sample obtained from a host, wherein the glucose monitor comprises a sensing membrane comprising an enzyme domain, wherein the receiver unit is configured to calibrate the sensor data from the continuous glucose sensor using the glucose concentration measurement from the single point glucose monitor, and wherein the enzyme domain of the sensing membrane of the continuous glucose sensor and the enzyme domain of the sensing membrane of the single point glucose monitor are substantially the same.

2. The system of claim 1, wherein the enzyme domain of the sensing membrane of the continuous glucose sensor and the enzyme domain of the sensing membrane of the single point glucose monitor comprise the same materials.

3. The system of claim 1, wherein the single point glucose monitor comprises a single use test strip configured to be releasably received by a port on the single point glucose monitor, and wherein the single use test strip of the stele point glucose monitor comprises the sensing membrane.

4. The system of claim 1, wherein the receiver unit further comprises programming to control administration of a constituent to the host.

5. The system of claim 4, wherein the programming to control administration of a constituent to the host is configured to determine at least one of an amount of insulin and a time of insulin administration.

6. The system of claim 1, wherein the receiver unit further comprises programming to calculate a rate of change of the continuous glucose data or a directional trend of the continuous glucose data.

7. The system of claim 6, wherein the receiver unit further comprises programming to control administration of a constituent to the host based at least in part on the rate of change of the continuous glucose data or the directional trend of the continuous glucose data.

8. The system of claim 1, wherein both the continuous glucose sensor and the single point glucose monitor use the same measurement technology, and wherein the measurement technology is selected from the group consisting of enzymatic, chemical, physical, electrochemical, spectrophotometric, polarimetric, calorimetric, and radiometric.

9. The system of claim 1, wherein the sensing membrane of the single point glucose monitor comprises one or more membrane domains or layers that are the same as one or more membrane domains or layers of the continuous glucose sensor.

10. The system of claim 9, wherein the sensing membrane of the single point glucose monitor comprises two or more membrane domains or layers that are the same as two or more membrane domains or layers of the continuous glucose sensor.

11. The system of claim 10, wherein the sensing membrane of the single point glucose monitor comprises three or more membrane domains or layers that are the same as three or more membrane domains or layers of the continuous glucose sensor.

12. The system of claim 1, wherein the sensing membrane of the single point glucose monitor comprises one or more materials or layers that are the same as one or more materials or layers of the sensing membrane of the continuous glucose sensor.

13. The system of claim 12, wherein the sensing membrane of the single point glucose monitor comprises two or more materials or layers that are the same as two or more materials or layers of the sensing membrane of the continuous glucose sensor.

14. The system of claim 13, wherein the sensing membrane of the single point glucose monitor comprises three or more materials or layers that are the same as three or more materials or layers of the sensing membrane of the continuous glucose sensor.

* * * * *

UNITED STATES PATENT AND TRADEMARK OFFICE
CERTIFICATE OF CORRECTION

PATENT NO.       : 7,927,274 B2
APPLICATION NO.  : 12/182083
DATED            : April 19, 2011
INVENTOR(S)      : Rasdal et al.

It is certified that error appears in the above-identified patent and that said Letters Patent is hereby corrected as shown below:

| Issued Patent | | Description of Discrepancy |
|---|---|---|
| Column | Line | |
| (Item 56) Page 6 Col. 2 | 15 | Under Other Publications, change "-implntable," to -- -implantable,--. |
| (Item 56) Page 6 Col. 2 | 20 | Under Other Publications, change "reliablity" to --reliability--. |
| (Item 56) Page 6 Col. 2 | 34 | Under Other Publications, change "Enzymlology," to --Enzymology,--. |
| (Item 56) Page 6 Col. 2 | 42 | Under Other Publications, change "systme" to --system--. |
| (Item 56) Page 6 Col. 2 | 47 | Under Other Publications, change "artifical" to --artificial--. |
| (Item 56) Page 6 Col. 2 | 65 | Under Other Publications, change "your and your" to --you and your--. |
| (Item 56) Page 7 Col. 1 | 2 | Under Other Publications, change "glocuse" to --glucose--. |
| (Item 56) Page 7 Col. 1 | 3 | Under Other Publications, change "Diabetese" to --Diabetes--. |
| (Item 56) Page 7 Col. 1 | 16 | Under Other Publications, change "Hypoglycaemia" to --Hypoglycemia--. |

Signed and Sealed this
Eleventh Day of October, 2011

David J. Kappos
*Director of the United States Patent and Trademark Office*

| | | |
|---|---|---|
| (Item 56) Page 7 Col. 1 | 26 | Under Other Publications, change "Thechnol." to --Technol.--. |
| (Item 56) Page 7 Col. 1 | 31 | Under Other Publications, change "Diabetese" to --Diabetes--. |
| (Item 56) Page 7 Col. 1 | 47 | Under Other Publications, change "inactiviation" to --inactivation--. |
| (Item 56) Page 7 Col. 2 | 29 | Under Other Publications, change "Aniodic" to --Anodic--. |
| (Item 56) Page 8 Col. 1 | 11 | Under Other Publications, change "activitiy," to --activity,--. |
| (Item 56) Page 8 Col. 1 | 32 | Under Other Publications, change "Beioelectronics," to --Bioelectronics,--. |
| (Item 56) Page 8 Col. 1 | 33 | Under Other Publications, change "glocuse" to --glucose--. |
| (Item 56) Page 8 Col. 1 | 47 | Under Other Publications, change "valication" to --validation--. |
| (Item 56) Page 8 Col. 1 | 48 | Under Other Publications, change "iunsulin interaaction in tyhpe 1" to --insulin interaction in type 1--. |
| (Item 56) Page 8 Col. 1 | 61 | Under Other Publications, change "Electronanalysis" to --Electroanalysis--. |
| (Item 56) Page 8 Col. 2 | 18 | Under Other Publications, change "amperometeric" to --amperometric--. |
| (Item 56) Page 8 Col. 2 | 55 | Under Other Publications, change "termistor" to --thermistor--. |
| (Item 56) Page 8 Col. 2 | 56 | Under Other Publications, change "metobolites," to --metabolites,--. |
| (Item 56) Page 8 Col. 2 | 58 | Under Other Publications, before "and" change "cholesteral and cholesteral" to --cholesterol and cholesterol--. |

CERTIFICATE OF CORRECTION (continued)
U.S. Pat. No. 7,927,274 B2

| | | |
|---|---|---|
| (Item 56) Page 8 Col. 2 | 62 | Under Other Publications, change "Apllied" to --Applied--. |
| (Item 56) Page 9 Col. 1 | 67 | Under Other Publications, change "Subcutaenous" to --Subcutaneous--. |
| (Item 56) Page 9 Col. 2 | 55 | Under Other Publications, change "Thechnol." to --Technol.--. |
| (Item 56) Page 10 Col. 1 | 12 | Under Other Publications, change "Membrance" to --Membrane--. |
| (Item 56) Page 10 Col. 1 | 20 | Under Other Publications, change "cholesteral" to --cholesterol--. |
| (Item 56) Page 10 Col. 1 | 37 | Under Other Publications, change "Deabetes" to --Diabetes--. |
| (Item 56) Page 10 Col. 1 | 56 | Under Other Publications, change "Tranducers" to --Transducers--. |
| (Item 56) Page 11 Col. 1 | 15 | Under Other Publications, change "hypoglycaemic" to --hypoglycemic--. |
| (Item 56) Page 11 Col. 1 | 22 | Under Other Publications, change "Thechnol." to --Technol.--. |
| (Item 56) Page 11 Col. 1 | 24 | Under Other Publications, change "Senso" to --Sensor--. |
| (Item 56) Page 11 Col. 1 | 33 | Under Other Publications, change "basedon" to --based--. |
| (Item 56) Page 11 Col. 1 | 57 | Under Other Publications, change "patents" to --patients--. |
| (Item 56) Page 11 Col. 2 | 18 | Under Other Publications, change "Thechnol." to --Technol.--. |
| (Item 56) Page 11 Col. 2 | 49 | Under Other Publications, change "assitance" to --assistance--. |
| (Item 56) Page 11 Col. 2 | 50 | Under Other Publications, change "Thechnol." to --Technol.--. |

CERTIFICATE OF CORRECTION (continued)
U.S. Pat. No. 7,927,274 B2

| | | |
|---|---|---|
| 19 | 20 | Change "disposed of" to --disposed off--. |
| 22 | 29 | Change "can by" to --can be--. |
| 22 | 44 | Change "enyzmatically" to --enzymatically--. |
| 24 | 50 | Change "corn" to --com--. |
| 33 | 13 | In Claim 3, change "stele" to --single--. |